United States Patent
Zhong et al.

(10) Patent No.: US 8,940,938 B2
(45) Date of Patent: Jan. 27, 2015

(54) MICHAEL REACTION WITH RECOVERY OF THE CATALYST

(75) Inventors: Guofu Zhong, Singapore (SG); Bin Tan, Singapore (SG); Xuan Zhang, Singapore (SG); Pei Juan Chua, Singapore (SG)

(73) Assignee: Nanyang Technological University, Singapore (SG)

( * ) Notice: Subject to any disclaimer, the term of this patent is extended or adjusted under 35 U.S.C. 154(b) by 237 days.

(21) Appl. No.: 12/782,706

(22) Filed: May 18, 2010

(65) Prior Publication Data

US 2012/0004424 A1 Jan. 5, 2012

Related U.S. Application Data

(60) Provisional application No. 61/179,563, filed on May 19, 2009, provisional application No. 61/263,185, filed on Nov. 20, 2009.

(51) Int. Cl.
C07C 205/03 (2006.01)
C07D 333/22 (2006.01)
C07C 201/12 (2006.01)
C07D 307/46 (2006.01)
C07D 401/06 (2006.01)

(52) U.S. Cl.
CPC ............ C07D 333/22 (2013.01); C07C 201/12 (2013.01); C07D 307/46 (2013.01); C07D 401/06 (2013.01)
USPC ....................................................... 568/306

(58) Field of Classification Search
CPC ................................................... C07D 401/04
USPC ..................................... 549/77, 496; 568/306
See application file for complete search history.

(56) References Cited

PUBLICATIONS

Carey, F.A., et al. "Advanced Organic Chemistry." 3rd edition. 1990. p. 39-46.*
Li, X., Cun, L., et al. "Highly enantioselective Michael addition of malononitrile to α, β-unsaturated ketones." Org. Biomol. Chem. 2008. vol. 6. pp. 349-353.*
Connon, SJ. "Asymmetric catalysis with bifunctional cinchona alkaloid-based urea and thiourea organocatalysts." Chem. Commun. 2008. pp. 2499-2510.*
Smith. "Michael addition." Http://orgchem.chem.uconn.edu/namereact/michael.html.*
Feringa, BL., De Vries, A. "C—C Bonds by Catalytic Enantioselective 1,4-Addition." pp. 183-185.*
Kemball, C., Dowden, D.A. "Michael Addition Reactions." Catalysis. vol. 2. 1978.*
Cordell, GA. "Asymmetric Michael-Addition." The Alkaloids: Chemistry and Biology. 2000.*
Smith. "Michael addition." © Jul. 2007. Http://orgchem.chem.uconn.edu/namereact/michael.html.*
Feringa, BL., De Vries, A. "C—C Bonds by Catalytic Enantioselective 1,4-Addition." © 1995. pp. 183-185.*
Dioumaev, V.K.,& Bullock, R.M., Nature (2003) 424, 530.
Ishihara, K., et al., Synlett (2002) 1299.
Luo, S., et al., Angew. Chem., Int. Ed. (2006) 45, 3093.
Chowdari, N.S., et al., Synlett (2003) 1906.
Font, D., et al., Org. Lett. (2006) 8, 4653.
Font, D., et al., Org. Lett. (2007) 9, 1943).
Dalicsek, Z., et al., Org. Lett. (2005) 7, 3243.
Zu, L., et al., Org. Lett. (2006) 8, 3077.
Huang, K., et al., Org. Chem. (2006) 71, 8320.
Cole, A., et al., J. Am. Chem. Soc. (2002) 124, 5962.
Yao, Q., & Zhang, Y., J. Am. Chem. Soc. (2004) 126, 74.
Lu X., & Deng L., Angew. Chem., Int. Ed. (2008) 47, 7710.
T. Okino, et al., J. Am. Chem. Soc. (2003) 125, 12672.
T. Okino, et al., J. Am. Chem. Soc. (2005) 127, 119.

* cited by examiner

Primary Examiner — Andrew D Kosar
Assistant Examiner — John S Kenyon
(74) Attorney, Agent, or Firm — Sam K. Tahmassebi; TechLaw LLP

(57) ABSTRACT

Disclosed is a process of carrying out a Michael reaction with recovery of the catalyst, where a compound of formula (1):

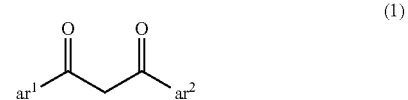

(1)

is reacted with a compound of formula (2):

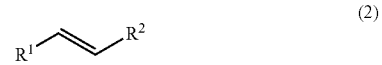

(2)

in the presence of a catalyst of formula (4):

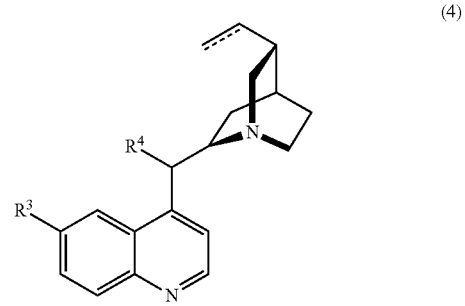

(4)

where the compounds of formulae (1) and (2) undergo a Michael reaction.

9 Claims, 65 Drawing Sheets

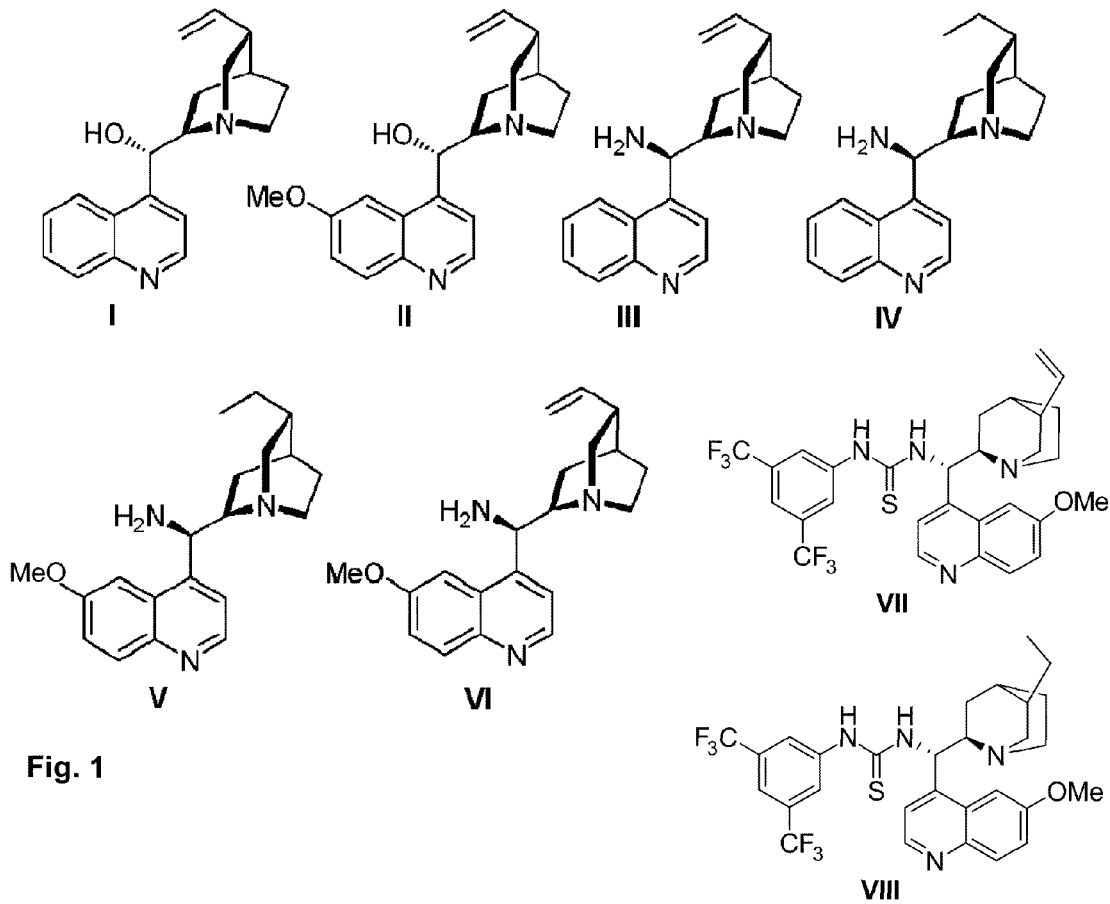
Fig. 1
Fig. 2
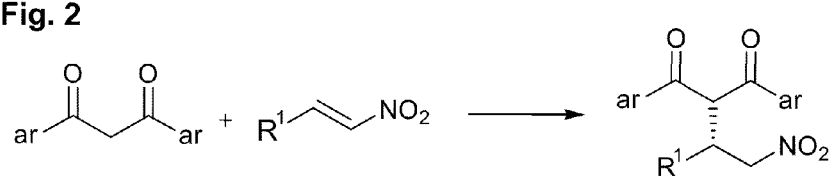
Fig. 3A
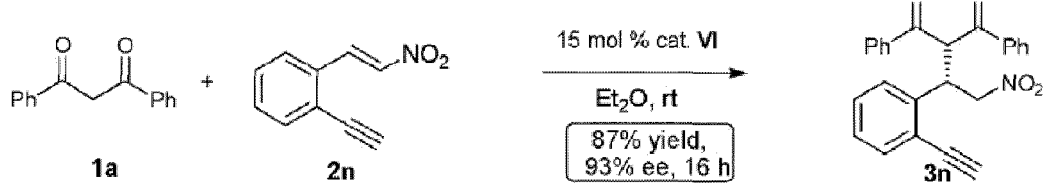

| Entry | Catalyst | Solvent | t/h | Yield (%)[b] | Ee (%)[c] |
|---|---|---|---|---|---|
| 1 | I | Et$_2$O | 8 | 95 | 21 |
| 2 | II | Et$_2$O | 8 | 95 | 2 |
| 3 | III | Et$_2$O | 8 | 97 | 3 |
| 4 | IV | Et$_2$O | 8 | 98 | 7 |
| 5 | V | Et$_2$O | 8 | 94 | 93 |
| 6 | VI | Et$_2$O | 8 | 96 | 98 |
| 7 | VI | MeOH | 8 | 93 | 65 |
| 8 | VI | THF | 15 | 82 | 98 |
| 9 | VI | Toluene | 8 | 97 | 95 |
| 10[d] | VI | Et$_2$O | 17 | 94 | 98 |
| 11[e] | VI | Et$_2$O | 12 | 85 | 98 |

| Entry | R[1] | Product | t/h | Yield (%)[b] | Ee (%)[c] |
|---|---|---|---|---|---|
| 1 | Ph | 3a | 8 | 96 | 98 |
| 2 | 4-OMe-Ph | 3b | 12 | 92 | 97 |
| 3 | 3-OMe-Ph | 3c | 16 | 91 | 93 |
| 4 | 2-OMe-Ph | 3d | 16 | 94 | 99 |
| 5 | 4-Me-Ph | 3e | 12 | 93 | 98 |
| 6 | 4-Br-Ph | 3f | 8 | 96 | > 99 |
| 7 | 4-Cl-Ph | 3g | 8 | 97 | > 99 |
| 8 | 2-Thienyl | 3h | 12 | 92 | 97 |
| 9 | 2-Furyl | 3i | 16 | 91 | 98 |
| 10 | 3-Furyl | 3j | 12 | 91 | 97 |
| 11 | 1-Naphthyl | 3k | 16 | 88 | 96 |
| 12 | 2-NO$_2$-Ph | 3l | 12 | 92 | 94 |
| 13 | 4-NO$_2$-Ph | 3m | 24 | 86 | 94 |

| cycle | R¹ = Ph (3a) | | | R¹ = 4-Cl-Ph (3g) | | |
|---|---|---|---|---|---|---|
| | t (h) | Yield | ee (%) | t (h) | Yield | ee (%) |
| 1 | 8 | 74 | 98 | 8 | 76 | >99 |
| 2 | 9 | 83 | 97 | 10 | 82 | 99 |
| 3 | 10 | 110 | 97 | 11 | 108 | 98 |
| 4 | 12 | 95 | 96 | 13 | 96 | 97 |
| 5 | 15 | 109 | 96 | 16 | 114 | 96 |
| 6 | 19 | 94 | 95 | 19 | 97 | 96 |
| 7 | 30 | 101 | 94 | 23 | 97 | 95 |

| cycle | R¹ = Ph (3a) | | | R¹ = 4-Br-Ph (3g) | | |
|---|---|---|---|---|---|---|
| | t (h)[b] | yield[c] | ee (%)[d] | t (h)[b] | yield[c] | ee (%)[d] |
| 1 | 3 | | 96 | 3 | | 94 |
| 2 | 3 | | 95 | 4 | | 94 |
| 3 | 5 | | 95 | 4 | | 94 |
| 4 | 7 | Average | 95 | 4 | Average | 94 |
| 5 | 7 | 97% | 95 | 4 | 95% | 94 |
| 6 | 8 | for 10 | 95 | 6 | for 10 | 94 |
| 7 | 10 | recycles | 94 | 7 | recycles | 97 |
| 8 | 10 | | 95 | 7 | | 92 |
| 9 | 12 | | 95 | 10 | | 94 |
| 10 | 15 | | 95 | 12 | | 98 |

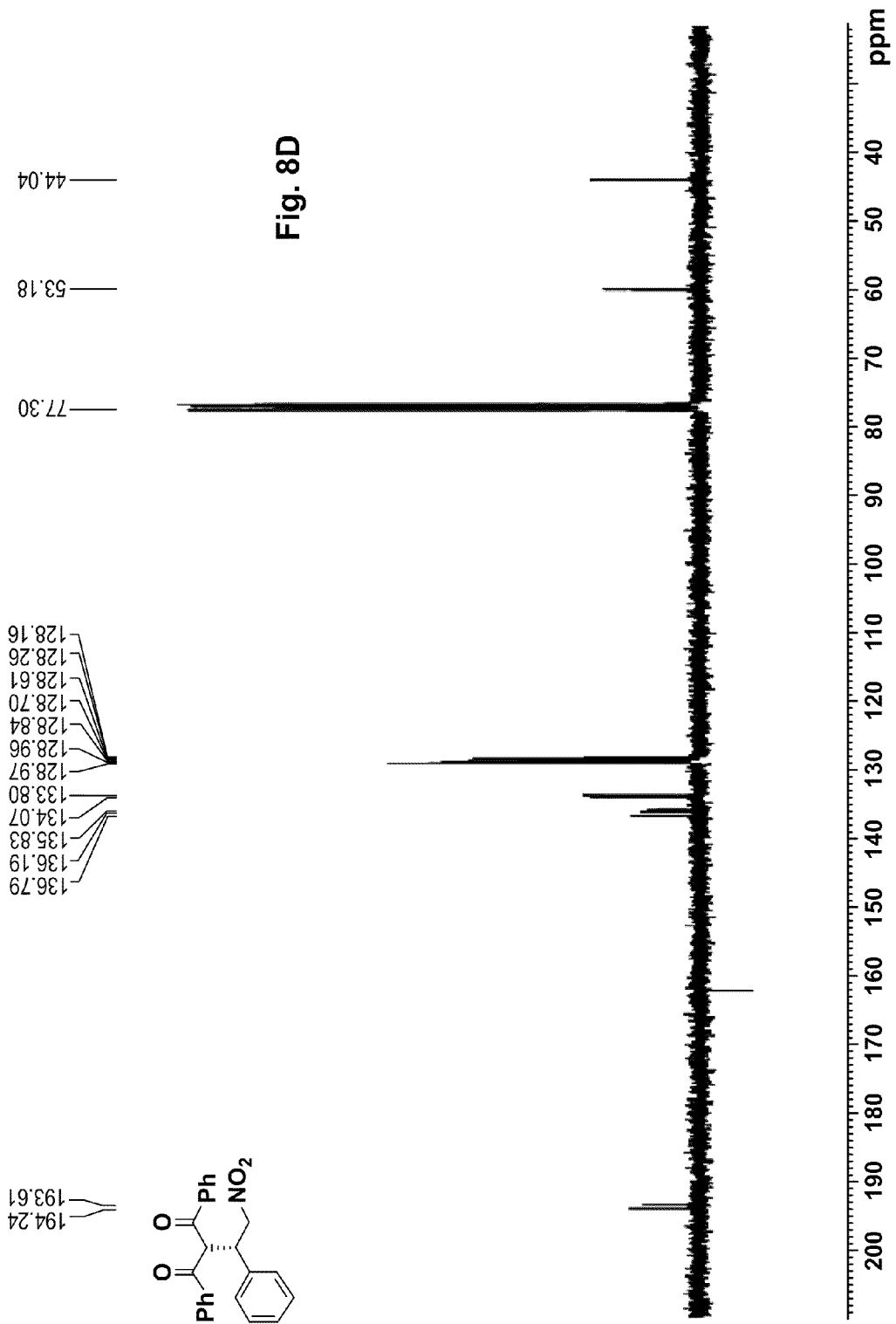

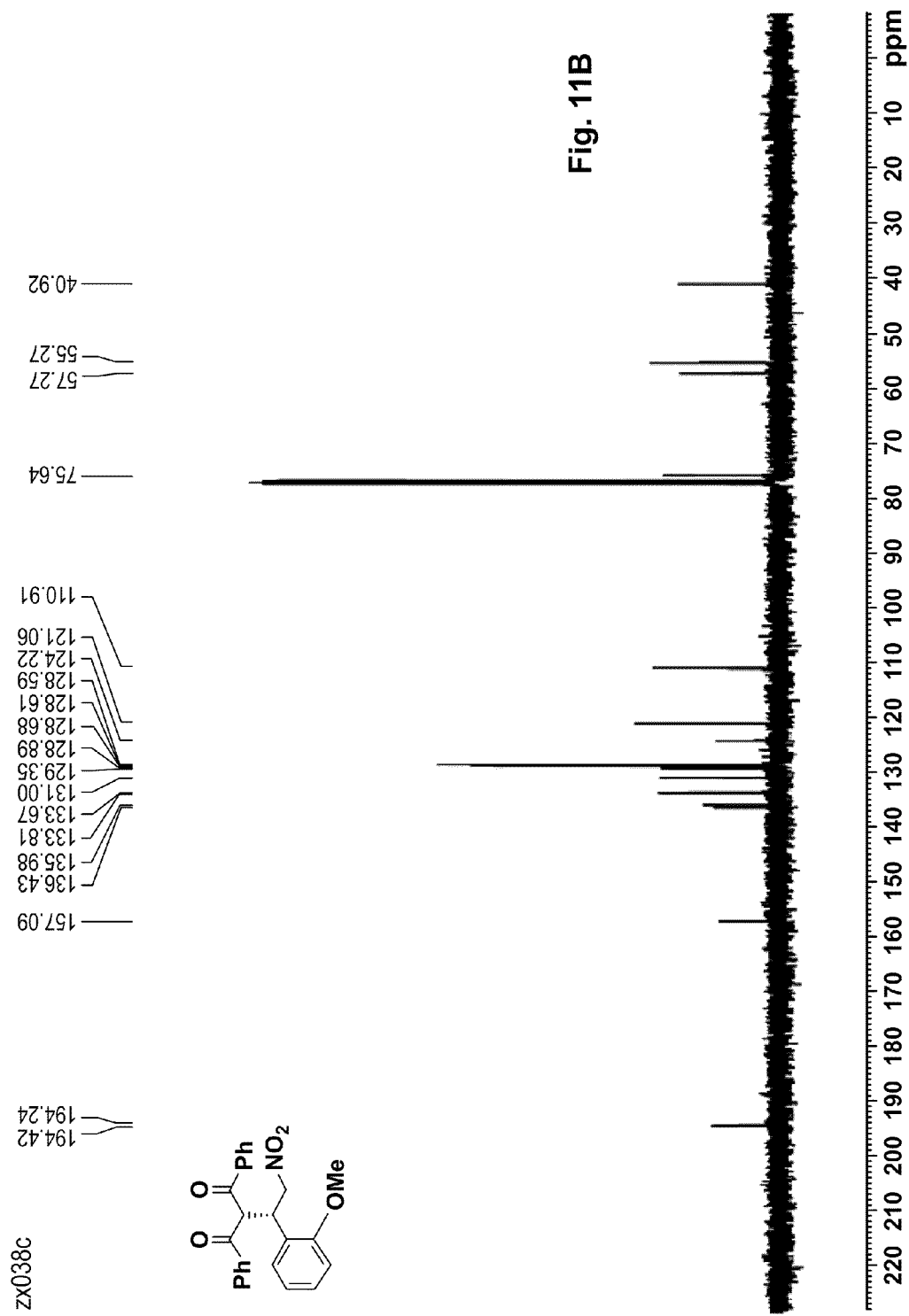

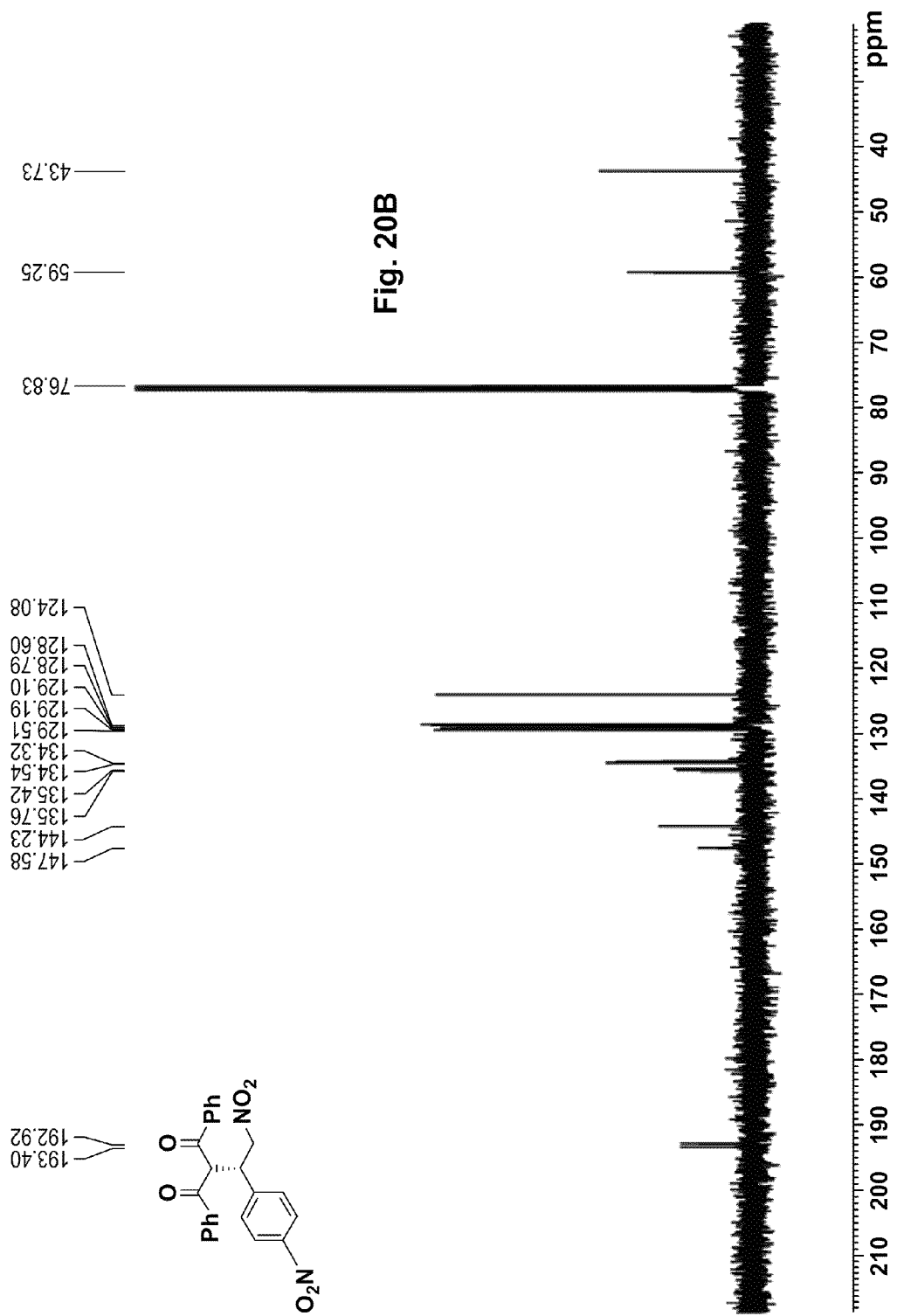

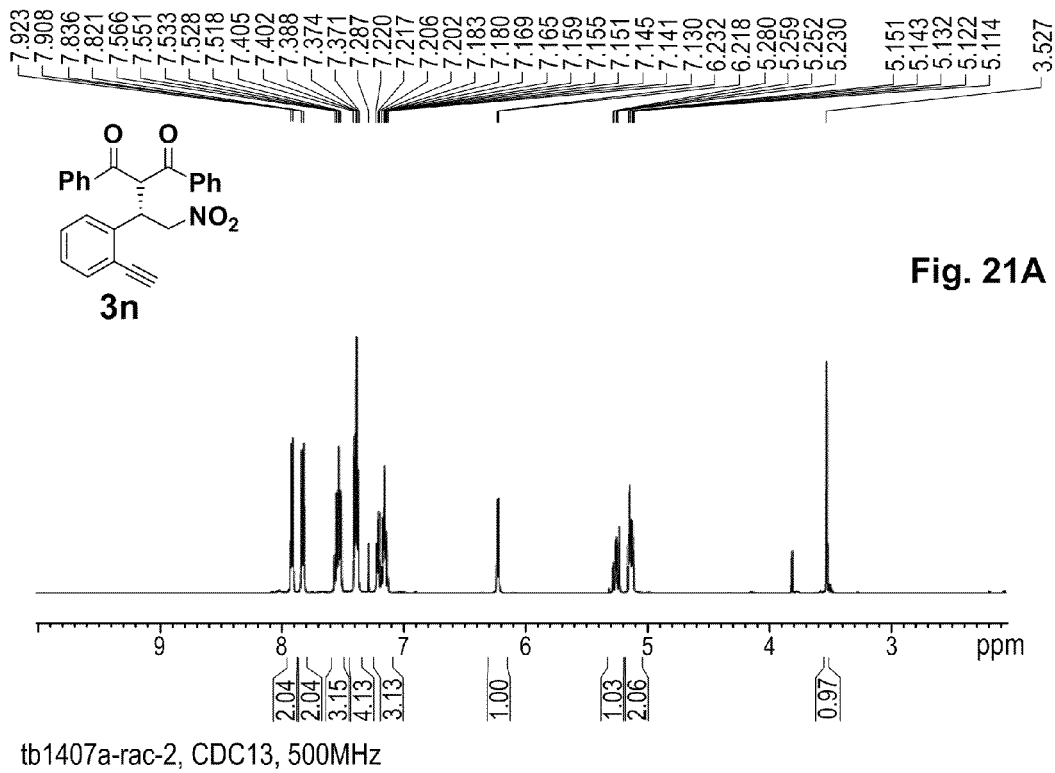
Fig. 21A
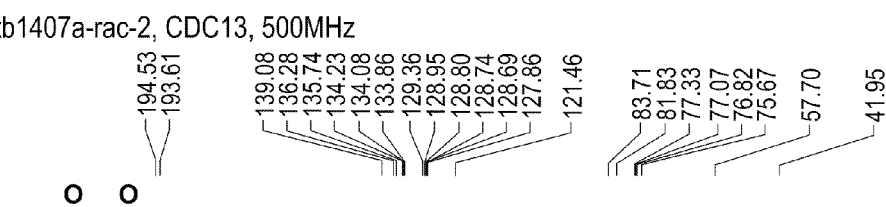
tb1407a-rac-2, CDC13, 500MHz
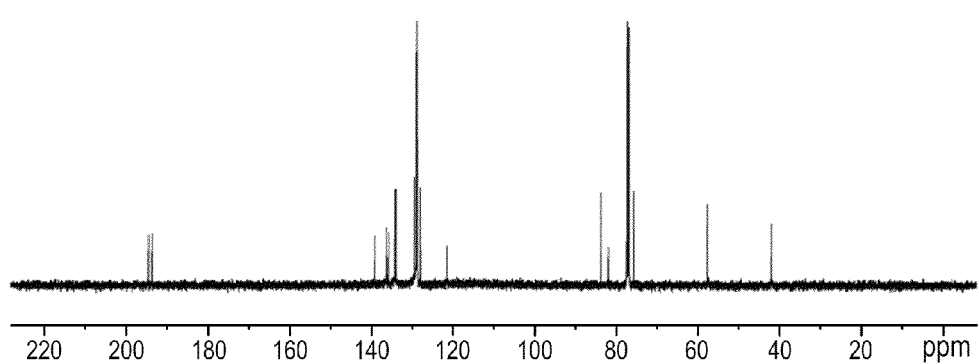
Fig. 21B

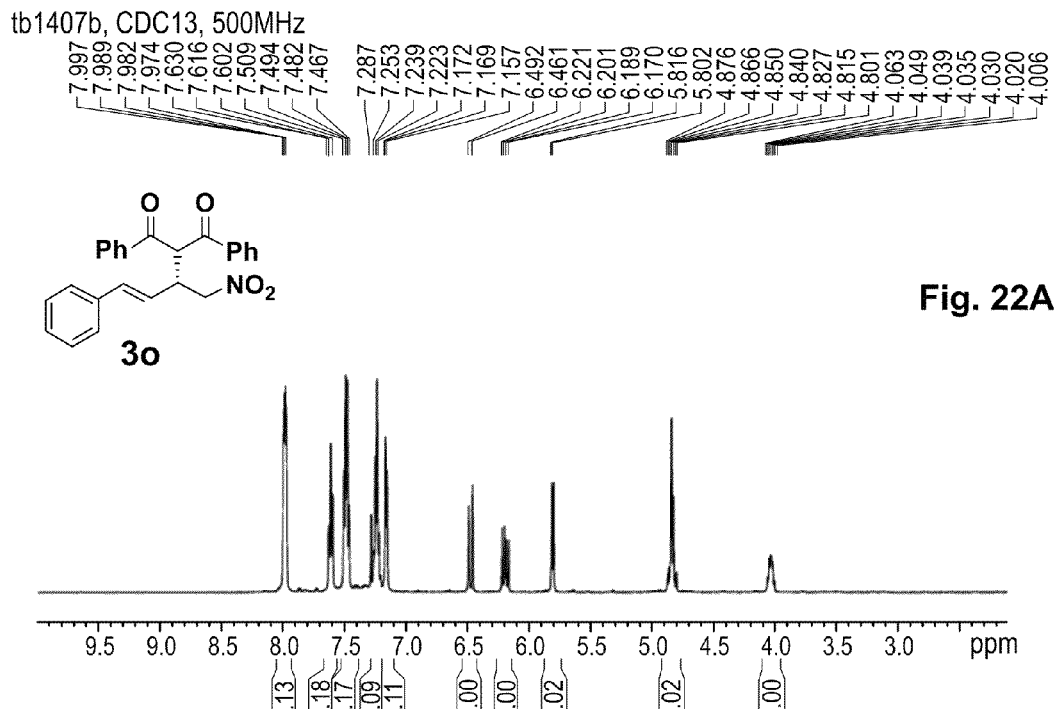
Fig. 22A
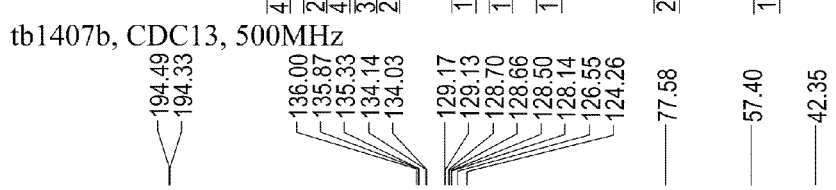
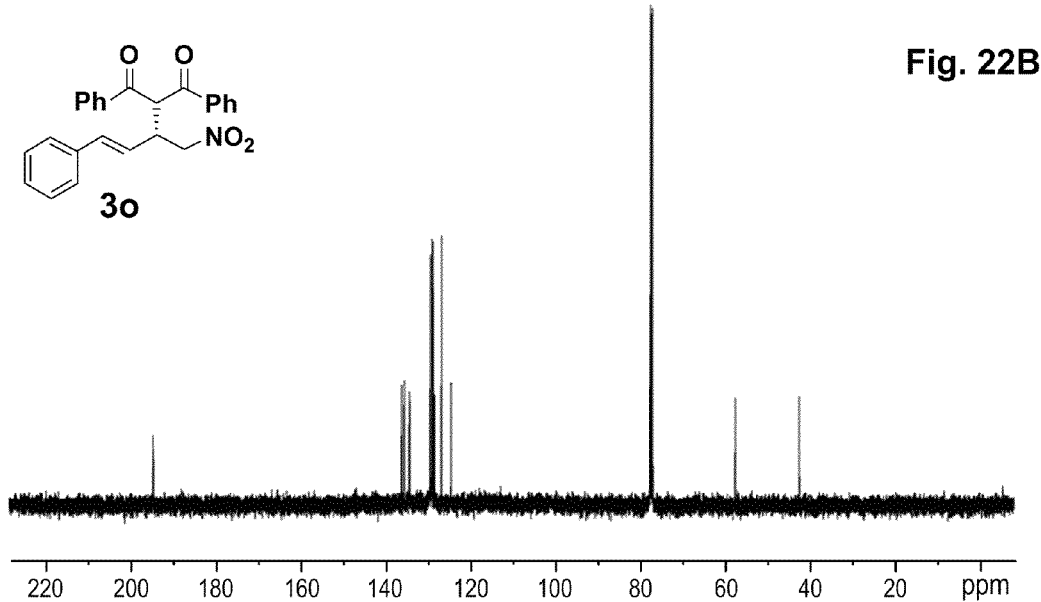
Fig. 22B

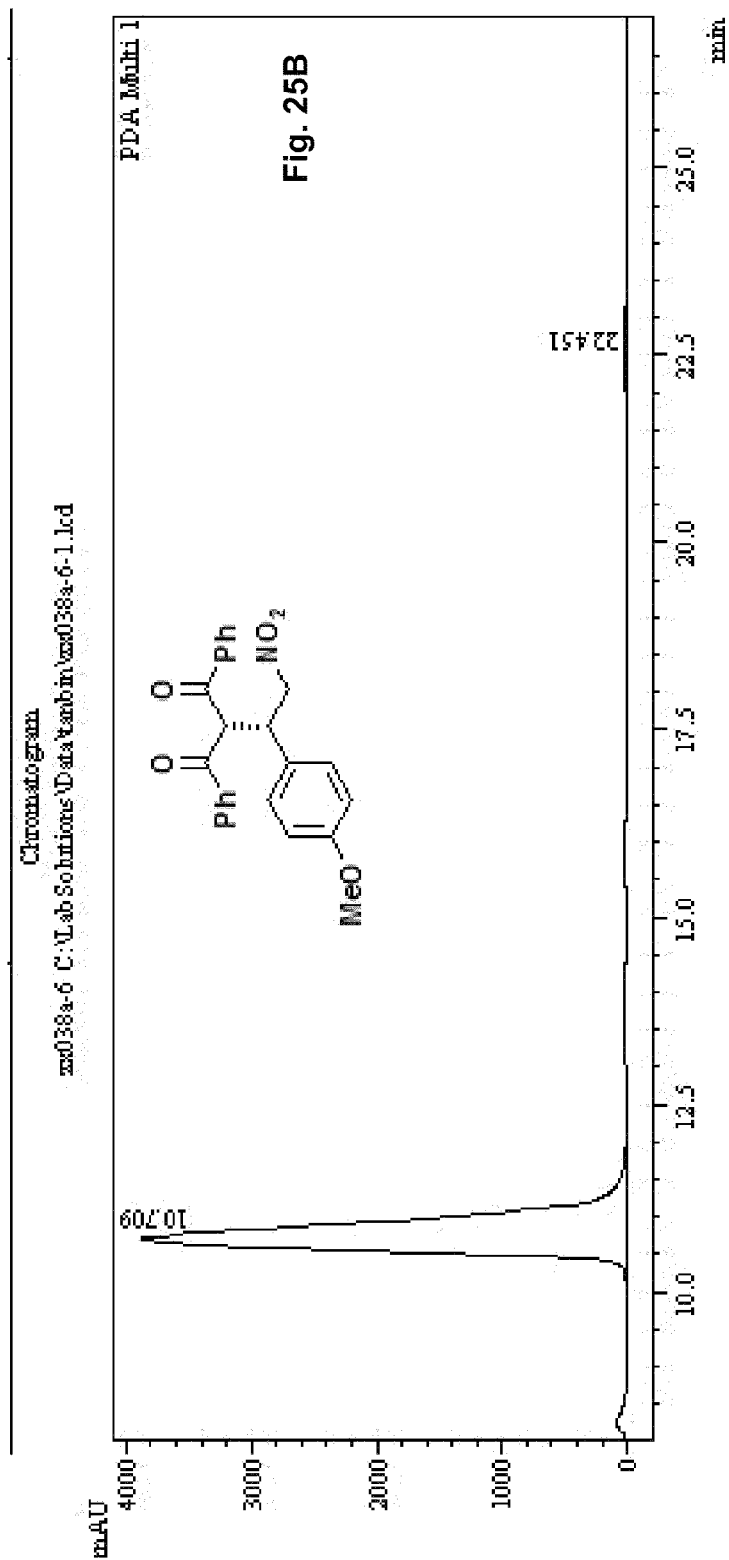

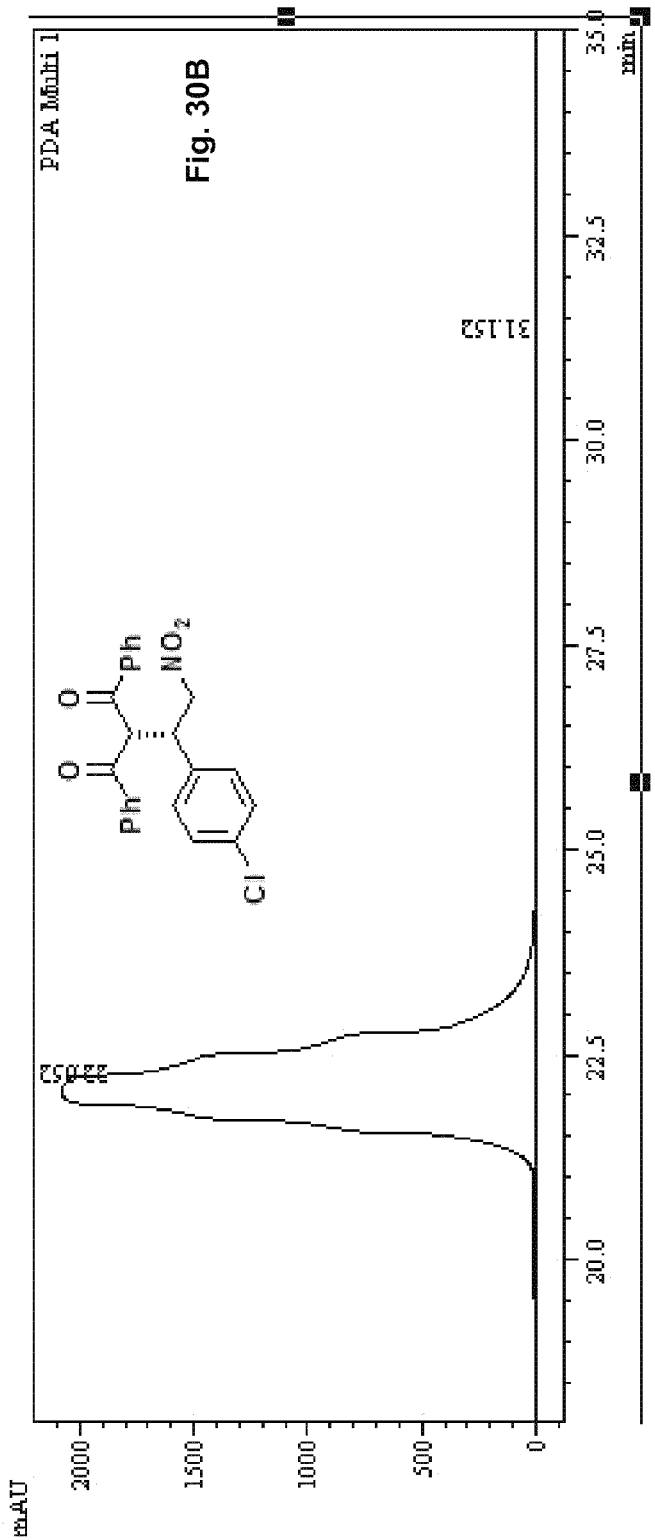

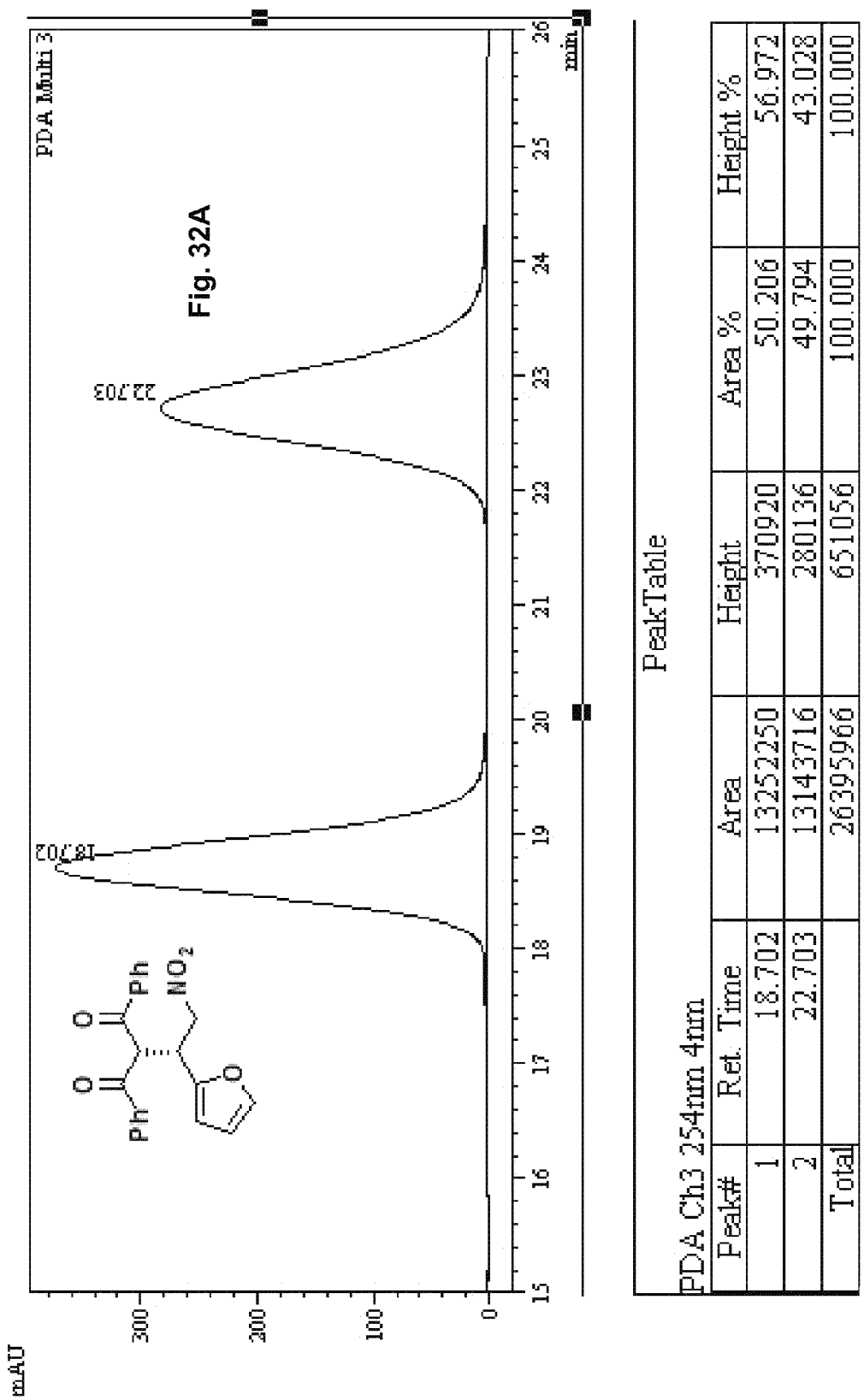

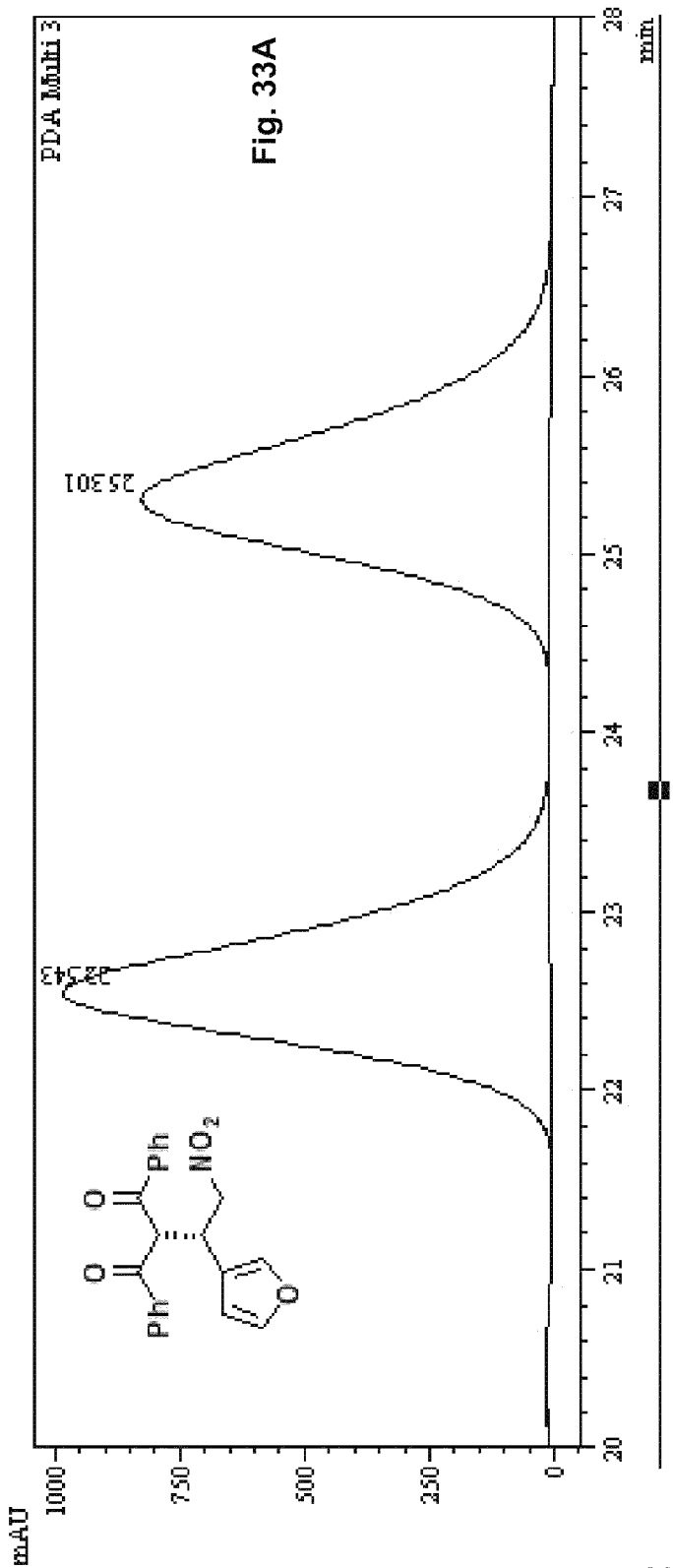

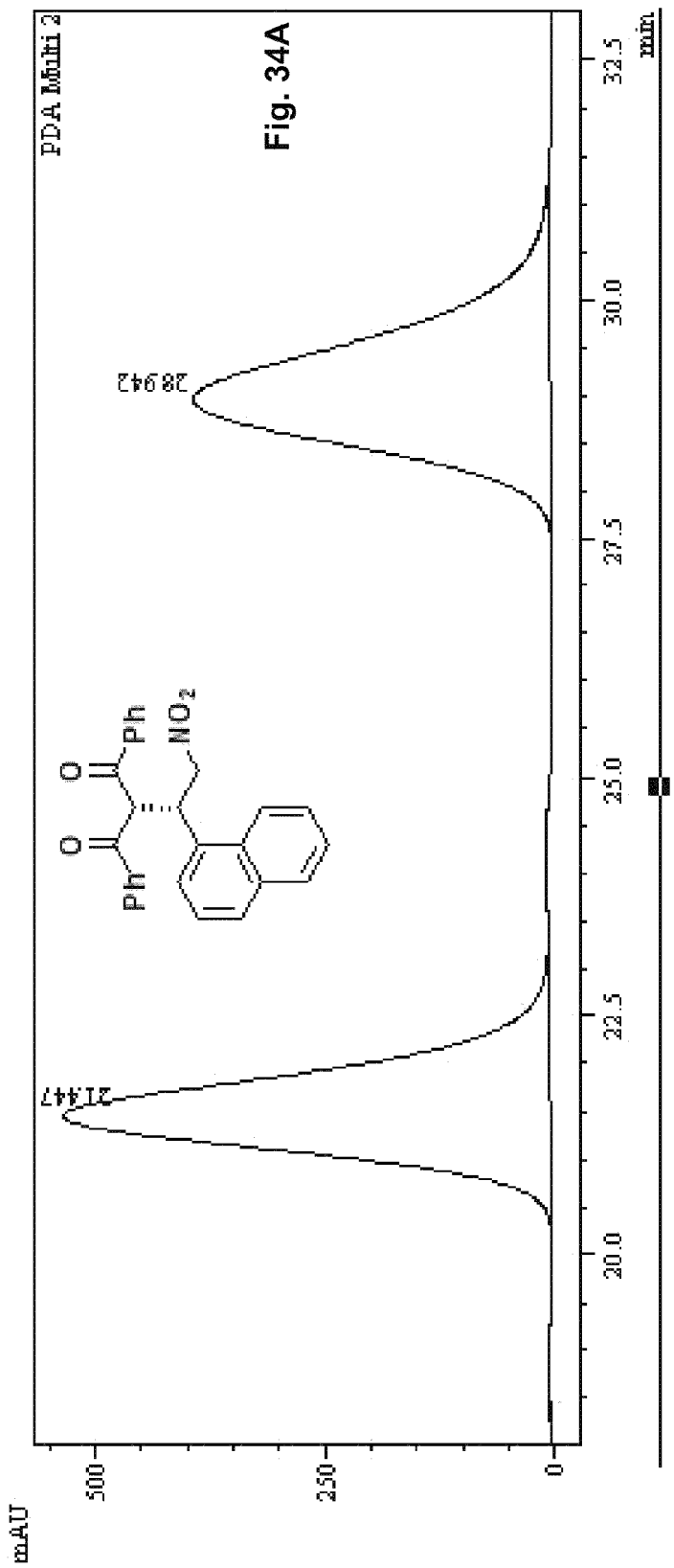

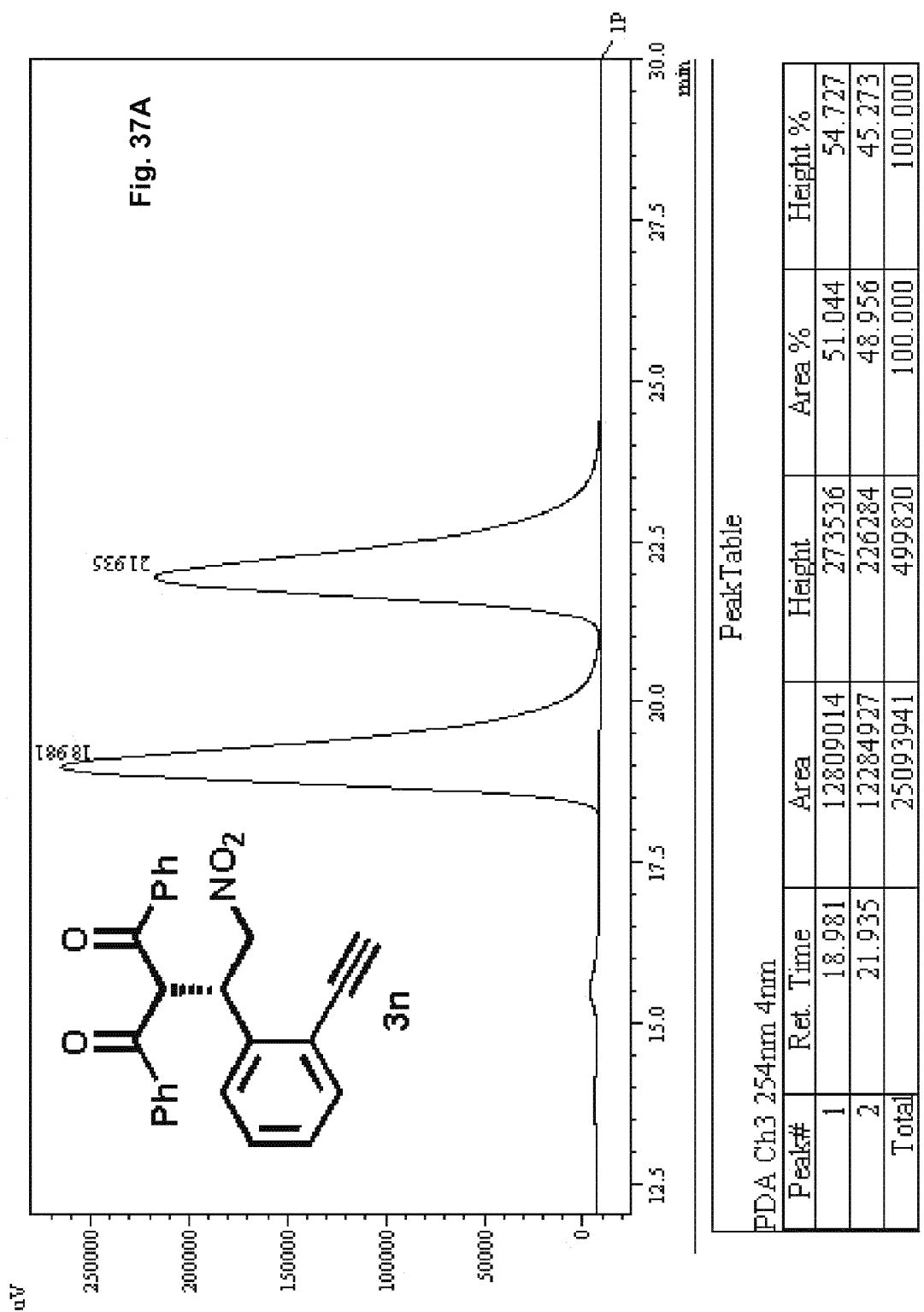

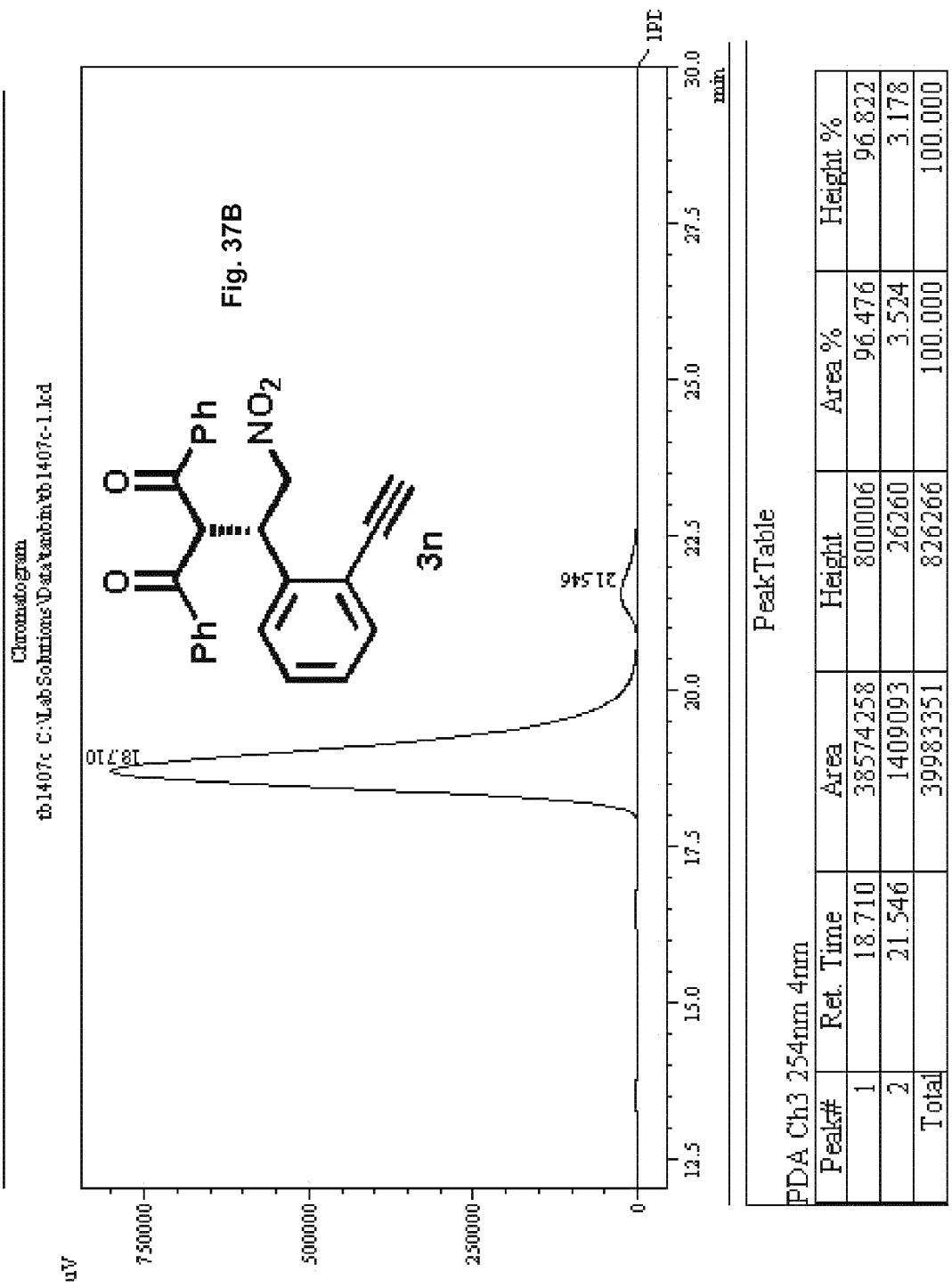

MICHAEL REACTION WITH RECOVERY OF THE CATALYST

CROSS-REFERENCE TO RELATED APPLICATIONS

This application makes reference to and claims the benefit of priority of an application for "Highly Recyclable Organocatalysis: Enantioselective Michael Addition of 1,3-Diaryl-1,3-propanedione to Nitroolefins" filed on May 19, 2009 with the United States Patent and Trademark Office, and there duly assigned Ser. No. 61/179,563. This application further makes reference to and claims the benefit of priority of an application for a "Michael Reaction With Recovery Of The Catalyst" filed on Nov. 20, 2009 with the United States Patent and Trademark Office, and there duly assigned Ser. No. 61/263,185. The contents of said applications filed on May 19, 2009 and on Nov. 20, 2009 are incorporated herein by reference for all purposes in their entirety.

FIELD OF THE INVENTION

The present invention provides a process of carrying out a Michael reaction with recovery of the catalyst. The Michael donor in the Michael reaction of the process is a 1,3-diketone.

BACKGROUND OF THE INVENTION

Recent years have witnessed a dramatic upsurge in awareness among chemists of the potential utility of asymmetric organocatalysis as a tool for the synthesis of enantiopure molecules under mild and environmentally benign conditions. The Michael addition of 1,3-dicarbonyl nucleophiles to nitroolefins 2 provides a particularly attractive target for organocatalyst design, largely due to the ready availability and high reactivity of nitroalkenes and the ability of the nitro functionality to accept hydrogen bonds from suitably designed catalyst systems, especially for the synthesis of important nitrogen containing bioactive agrochemical and pharmaceutical compounds. Thus, reactions of this nature have been reported to proceed in high yield and with good enantioselectivity by the use of various asymmetric catalysts. In contrast, organocatalytic conjugated additions using aromatic ketones as the Michael donor are rarely studied. 1,3-Diphenyl-1,3-propanedione (1a) is for instance known not to be a good Michael donor due to the steric hindrance of the two aryl groups and generally requires harsh reaction conditions and long reaction times.

The development of a highly enantioselective recyclable strategy (Dioumaev, V. K., & Bullock, R. M., *Nature* (2003) 424, 530; Ishihara, K., et al., *Synlett* (2002) 1299) for organocatalysis remains a challenging task. A few recyclable processes have been designed to this day, by attaching the catalyst to polymers (Font, D., et al., *Org. Lett.* (2006) 8, 4653; Font, D., et al., *Org. Lett.* (2007) 9, 1943), using recyclable fluorous catalysts (Huang, K., et al., *Org. Chem.* (2006) 71, 8320; Cole, A., et al., *J. Am. Chem. Soc.* (2002) 124, 5962; Luo, S., et al., *Angew. Chem., Int. Ed.* (2006) 45, 3093) and ionic liquids (Yao, Q., & Zhang, Y., *J. Am. Chem. Soc.* (2004) 126, 74; Dalicsek, Z., et al., *Org. Lett.* (2005) 7, 3243; Zu, L., et al., *Org. Lett.* (2006) 8, 307; Chowdari, N. S., et al., *Synlett* (2003) 1906). However, only moderate results have been achieved so far.

Accordingly, it is an object of the present invention to provide a process of carrying out a Michael reaction in which the catalyst can be recycled.

SUMMARY OF THE INVENTION

The invention relates to a process that involves a Michael addition reaction of an 1,3-diketone to a Michael acceptor in which a readily accessible organocatalyst is used and which involves a recyclable homogenous organocatalysis strategy. As the Michael acceptor in the Michael addition reaction even a nitroolefin readily undergoes the reaction. The Michael addition may also be an asymmetric Michael addition reaction.

Hence, the invention provides a process of carrying out a Michael reaction with recovery of the catalyst. The process includes providing in an aliphatic ether as the solvent a first compound of the general formula (1)

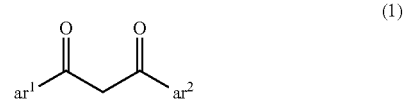

(1)

In formula (1) $ar^1$ and $ar^2$ are independently from one another an aromatic, including a heteroaromatic, moiety with a main chain of about 5 to about 30 carbon atoms and 0 to about 5 heteroatoms selected from the group N, O, S, Se and Si. The process includes providing in the same solvent a second compound of the general formula (2)

(2)

In formula (2) $R^1$ is one of an aliphatic, an alicyclic, an aromatic and an arylaliphatic moiety with a main chain of about 3 to about 30 carbon atoms and 0 to about 5 heteroatoms selected from the group N, O, S, Se and Si. $R^2$ is one of CN, CO—$R^5$, COOH, CHO, $NO_2$, and $SO_2$—$R^5$, wherein $R^5$ is one of an aliphatic, an alicyclic, an aromatic and arylaliphatic moiety with a main chain of about 1 to about 30 carbon atoms and 0 to about 5 heteroatoms selected from the group N, O, S, Se and Si. The first compound is typically provided in excess when compared to the second compound. The process also includes adding a catalyst of the general formula (4)

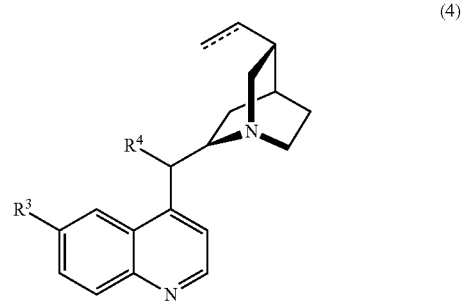

(4)

In formula (4) $R^3$ is one of H, OMe, OH, OTf, SH and $NH_2$. $R^4$ in formula (4) is one of OH and —N($R^8$)H. In this group $R^8$ is one of H, a carbamoyl group, and a thiocarbamoyl group. ---- represents one of a single and a double bond. By adding a catalyst of the general formula (4) a reaction mixture is formed. The process further includes allowing the first and the second compound to undergo a Michael reaction. Thereby the process includes allowing the formation of an adduct between the first compound and the catalyst of the general formula (4). Further, the process includes collecting the adduct between the first compound and the catalyst of the general formula (4).

BRIEF DESCRIPTION OF THE DRAWINGS

The invention will be better understood with reference to the detailed description when considered in conjunction with the non-limiting examples and the accompanying drawings.

FIG. 1 depicts structures of the Cinchona alkaloid catalysts that can be used in the process of the invention.

FIG. 2 illustrates an organocatalytic asymmetric Michael addition between a compound of the general formula (1) and an exemplary compound of the general formula (2).

FIGS. 3A-3C depict examples of pairs of Michael donors and acceptors.

FIG. 8C depicts a $^1$H NMR spectrum and FIG. 8D a $^{13}$C NMR spectrum of compound 3a.

FIG. 21A depicts a $^1$H NMR spectrum and FIG. 21B a $^{13}$C NMR spectrum of compound 3n.

FIG. 22A depicts a $^1$H NMR spectrum and FIG. 22B a $^{13}$C NMR spectrum of compound 3o.

FIG. 37 depicts an HPLC spectrum of a racemic mixture of compound 3n (A) in comparison the obtained product 3n (B).

DETAILED DESCRIPTION OF THE INVENTION

Figure 3B:
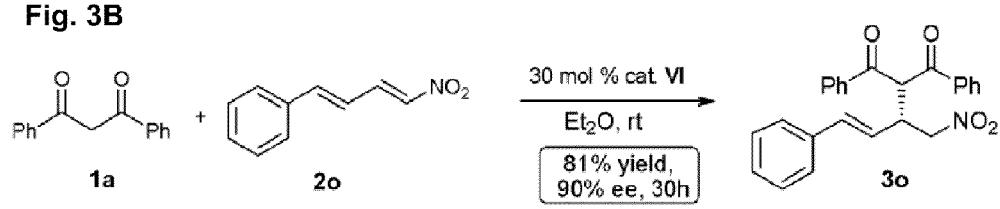

The invention relates to a process of carrying out a Michael reaction. In a Michael reaction a C—C bond is formed in a reaction between a Michael donor and a Michael acceptor. In the reaction that occurs in the process of the invention any Michael acceptor may be used. The Michael acceptor is an alkene substituted with a group $R^2$ that facilitates deprotonation of the —CH=C— group of the alkene. The Michael acceptor is thus of the general formula (2)

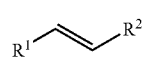

(2)

In formula (2) $R^1$ is one of an aliphatic, an alicyclic, an aromatic and an arylaliphatic moiety. The respective aliphatic, alicyclic, aromatic or arylaliphatic moiety of $R^1$ has a main chain of about 3 to about 30 carbon atoms, such as 4 to about 30 carbon atoms or 5 to about 30 carbon atoms, including about 3 to about 25 carbon atoms, about 3 to about 20 carbon atoms, about 4 to about 20 carbon atoms, about 3 to about 15 carbon atoms, about 4 to about 15 carbon atoms, about 3 to about 10 carbon atoms, about 4 to about 10 carbon atoms or about 5 to about 10 carbon atoms, such as 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety further has 0 to about 6, e.g. 0 to about 5 or 0 to about 4, such as 0, 1, 2, 3, 4, 5 or 6 heteroatoms. A respective heteroatom may be one of N, O, S, Se and Si. $R^2$ is an electron withdrawing group. $R^2$ may be one of CN, COOH, COOR$^5$, COOCOR$^5$

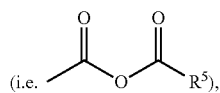

CHO, CO—R$^5$, CONR$^5$R$^6$, NO$_2$, and SO$_2$—R$^5$. R$^5$ is one of a silyl group, an aliphatic, an alicyclic, an aromatic and arylaliphatic moiety with a main chain of about 1 to about 30 carbon atoms, such as 2 to about 30 carbon atoms or 2 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. $R^6$ is, independently from $R^5$, one of H, a silyl group, an aliphatic, an alicyclic, an aromatic and arylaliphatic moiety with a main chain of about 1 to about 30 carbon atoms, such as 2 to about 30 carbon atoms or 2 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The respective aliphatic, alicyclic, aromatic or arylaliphatic moiety of $R^5$ and/or $R^6$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si.

A respective silyl group may be represented as

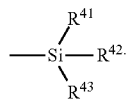

Each of $R^{41}$, $R^{42}$ and $R^{43}$ may be an independently selected aliphatic, alicyclic, aromatic, arylaliphatic or arylalicyclic group. A respective aliphatic, alicyclic, aromatic or arylaliphatic group may have a main chain of about 1 to about 30 carbon atoms, such as 2 to about 30 carbon atoms or 3 to about 30 carbon atoms, including about 1 to about 25 carbon atoms, about 1 to about 20 carbon atoms, about 2 to about 20 carbon atoms, about 1 to about 15 carbon atoms, about 2 to about 15 carbon atoms, about 3 to about 15 carbon atoms, about 1 to about 10 carbon atoms, about 2 to about 10 carbon atoms or about 3 to about 10 carbon atoms, such as 1, 2, 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety may further have 0 to about 6, e.g. 0 to about 5 or 0 to about 4, such as 0, 1, 2, 3, 4, 5 or 6 heteroatoms. A respective heteroatom may be one of N, O, S, Se and Si.

The term "aliphatic" means, unless otherwise stated, a straight or branched hydro-carbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moietie may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains, respectively, of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebis-benzene, 9-isopropylanthracene, 1,2,3-trimethylbenzene, 4-phenyl-2-buten-1-ol, 7-chloro-3-(1-methylethyl)-quinoline, 3-heptyl-furan, 6-[2-(2,5-diethyl-phenyl)ethyl]-4-ethyl-quinazoline or, 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzene-sulfonyl, nitrobenzenesulfonyl, and methanesulfonyl.

An aliphatic, alicyclic, aromatic or arylaliphatic moiety may carry further moieties such as side chains. Such further moieties may be an aliphatic, alicyclic, aromatic, arylaliphatic or arylalicyclic group that typically is of a main chain length of 1 to about 10, to about 15 or to about 20 carbon atoms. These further moieties may also carry functional groups (supra).

The Michael donor in a reaction that occurs in the process of the invention is a dicarbonyl compound of the general formula (5)

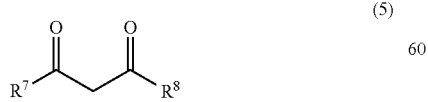

(5)

In formula (5) each of $R^7$ and $R^8$ are independently from one another one of hydrogen, a silyl group (see above in this regard), an aliphatic group, an alicyclic group, an aromatic group, an arylaliphatic group and an arylalicyclic group, including 0 to about 5, e.g. 1, 2, 3, 4 or 5 heteroatoms. The heteroatoms are independently selected from N, O, S, Se and Si. Each of the silyl group, aliphatic group, alicyclic group, aromatic group, arylaliphatic group and arylalicyclic group may have a main chain having 1 to about 40 carbon atoms, such as 1 to about 30 carbon atoms, 1 to about 20 carbon atoms or 1 to about 10 carbon atoms, e.g. 1, 2, 3, 4, 5, 6, 7, 8, 9, 10, 11, 12, 13, 14, 15, 16, 17, 18, 19, 20, 21, 22, 23, 24, 25 or 30 carbon atoms.

In some embodiments the Michael donor is a compound of the general formula (1)

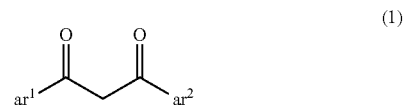

(1)

In formula (1) each of $ar^1$ and $ar^2$ are an independently selected aromatic moiety. Each respective aromatic moiety may have a main chain of about 5 to about 30 carbon atoms, such as 6 to about 30 carbon atoms or 5 to about 25 carbon atoms, including about 5 to about 20 carbon atoms, about 5 to about 20 carbon atoms, about 6 to about 20 carbon atoms, about 5 to about 15 carbon atoms, about 6 to about 15 carbon atoms, about 5 to about 10 carbon atoms, or about 6 to about 10 carbon atoms, such as 1, 2, 3, 4, 5, 6, 7, 8, 9, 10, 11, 12, 13, 14, 15, 16, 17, 18, 19 or 20 carbon atoms. The main chain of the respective aromatic moiety may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si.

The Michael donor is herein also referred to as the first compound and the Michael acceptor as the second compound. Typically the first compound is provided in excess to the second compound. The first compound may for example be provided in a molar amount of about 1.1-fold, about 1.2-fold, about 1.5-fold, about 2-fold, about 2.5-fold, about 3-fold, about 3.5-fold, about 4-fold, about 4.5-fold or about 5-fold in comparison to the molar amount of the second compound.

In the process of the invention a catalyst is used. The catalyst is generally a quinine-based or a quinidine-based compound. The catalyst is a compound of the general formula (4)

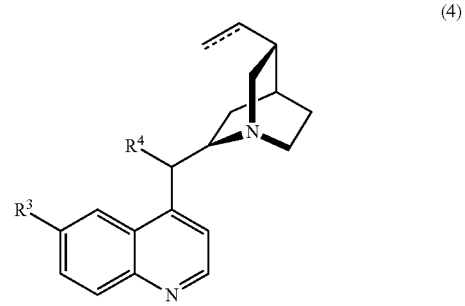

(4)

In formula (4) ⚌ represents one of a single and a double bond. Hence, in some embodiments ⚌ in the context of the structural formula represents —$CH_2$—$CH_3$, and in some embodiments —CH=$CH_2$. $R^3$ in formula (4) may in some embodiments be H. $R^3$ may also be one of OMe, $OR^5$, OH, OTf, SH, $SR^5$, NHR$^5$, and NH$_2$.R$^5$ is as defined above. NH$_2$.R$^4$ in formula (4) may be OH. R$^4$ may also be —N(R$^8$)H. The respective moiety R$^8$ may be H, a carbamoyl group or a thiocarbamoyl group. A respective carbamoyl group may be represented as —C(O)—N(R$^{11}$)—R$^{12}$ and a respective thiocarbamoyl group as —C(S)—N(R$^{11}$)—R$^{12}$. R$^{11}$ and R$^{12}$ in the carbamoyl group and the thiocarbamoyl group, respectively, are independent from one another H or one of an aliphatic, an alicyclic, an aromatic, an arylaliphatic, and an arylalicyclic group. A respective aliphatic, alicyclic, aromatic, arylaliphatic or arylcycloaliphatic group may have a main chain that typically includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aliphatic, alicyclic, aromatic, arylaliphatic or arylalicyclic group of R$^{11}$ and/or R$^{12}$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be selected from N, O, S, Se and Si.

The catalyst may also be used as a chiral catalyst. In such embodiments the catalyst employed in a process of the invention is a non-racemic chiral compound. Typically, the catalyst is in such embodiments of one of formulas (4A) and (4B)

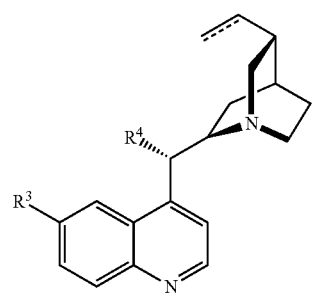

(4A)

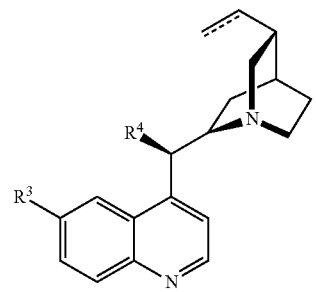

(4B)

In formulas (4A) and (4B) $\equiv$, R$^3$ and R$^4$ are as defined above.

A number of corresponding catalysts, such as cinchonidine, cinchonine, quinine or quinidine are commercially available. Modifications such as hydrations (e.g. dihydrocinchonidine) or conversions of functional groups can be carried out using standard procedures available in the art.

By adding the catalyst, i.e. typically the compound of the general formula (4), including of formulas (4A) or (4B), a reaction mixture is formed. In the reaction mixture the first and the second compound are allowed to undergo a Michael reaction. The Michael reaction may for example be described as

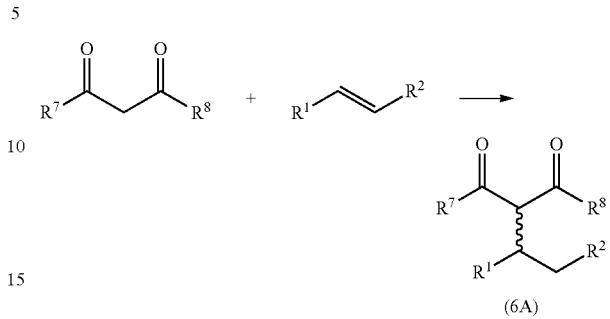

(6A)

In some embodiments the Michael reaction may for example be described as

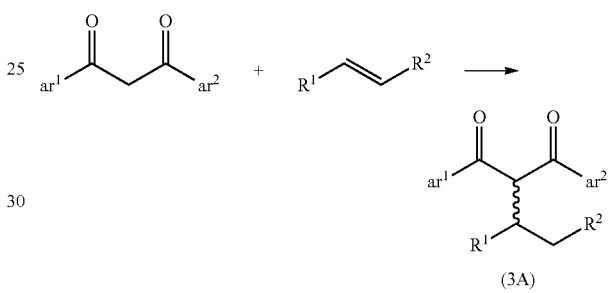

(3A)

In the reaction product (3A) and (6A) the symbol $\sim\!\!\sim$ indicates that the respective bond may have any configuration. Where a chiral catalyst is used, the Michael reaction may for example be described as

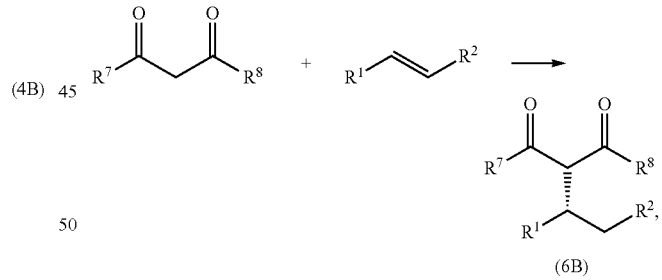

(6B)

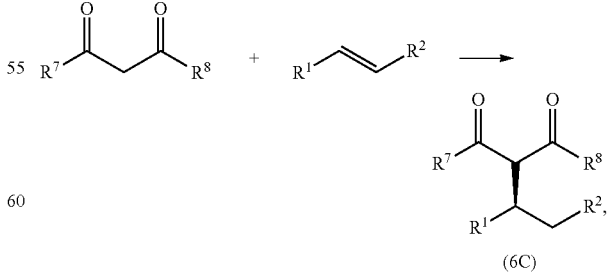

(6C)

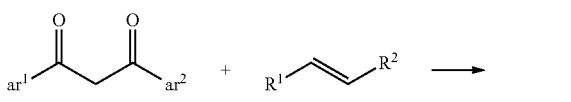

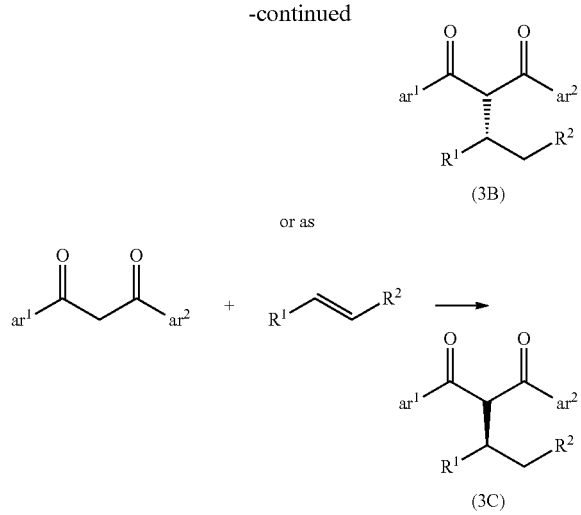

(3B)

or as (3C)

Typically the reactants and the catalyst are provided in a solvent that is an acyclic ether, such as an aliphatic ether. The solvent may therefore be taken to define a coordinating ether solvent. The ether solvent is typically represented by the general formula $R^9$—O—$R^{10}$. In this general formula $R^9$ and $R^{10}$ are independent from one another selected from an aliphatic, an alicyclic, an aromatic and an arylaliphatic moiety. The respective aliphatic, alicyclic, aromatic or arylaliphatic moiety of $R^1$ has a main chain of about 1 to about 25 carbon atoms, such as 1 to about 20 carbon atoms, e.g. 1 to about 15 carbon atoms, 1 to about 12 carbon atoms, 1 to about 10 carbon atoms, 1 to about 8 carbon atoms or 1 to about 6 carbon atoms, such as 1, 2, 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety may further include 0 to about 6, e.g. 0 to about 5 or 0 to about 4, such as 0, 1, 2, 3, 4, 5 or 6 heteroatoms. A respective heteroatom may be one of N, O, S, Se and Si. Typically the ether solvent is free of functional groups such as —OH, —SH, COOH, CHO or $NH_2$. Accordingly, $R^9$ and $R^{10}$ do typically not carry functional groups, albeit they may include one or more heteroatoms in a main chain or in a side chain, if present. The ether is acyclic in that $R^9$ and $R^{10}$ are not linked to define a bridge, but define two separate moieties. Each of $R^9$ and $R^{10}$ may nevertheless be a cyclic moiety. Illustrative examples of a suitable ether solvent include, but are not limited to, diethylether, dimethyl ether, methyl ethyl ether, methyl propyl ether, methyl isopropyl ether, methyl tert-butyl ether, ethyl tert-butyl ether, dimethoxyethane, di-n-propyl ether, diisopropyl ether, di-tert-butyl ether, di-sec-butyl ether, ethyleneglycol butyl ether, ethyleneglycol tert-butyl ether, di-tert-butyl ether, di-n-pentyl ether (amyl ether), ethyl-amyl-ether, n-pentyl-methyl ether, tert-amyl methyl ether, tert-amyl ethyl ether, di-allyl ether, methyl allyl ether, ethyl allyl ether, propyleneglycol allyl ether, ethyl phenyl ether, allyl phenyl ether, diphenyl ether, methyl-2-naphtyl ether or ethyl-2-naphtyl ether. Those skilled in the art will be aware of the boiling point of −23.6° C. of dimethyl ether, which may be useful in embodiments where the reaction is to be carried out at a low temperature and the solvent to be removed or replaced subsequently.

In addition the solvent may also include non-coordinating components such as an alkane or an alkene. The Michael reaction may be allowed to proceed at any desired temperature, such as a temperature in the range from −70° C. to about +70° C., depending on the boiling point of the solvent selected. The temperature may for instance be selected in the range from about −20° C. to about +40° C. or from about −20° C. to about +30° C. In one embodiment the reaction is carried out at room temperature, e.g. about +18° C.

In the course of the Michael reaction the formation of an adduct between the first compound and the catalyst of the general formula (4), including formula (4A) and (4B), occurs. This adduct tends to precipitate and can therefore be collected, for instance by filtration or by centrifugation, or a combination thereof. This adduct between the first compound and the catalyst is collected and can be reused. Using the method of the invention it s therefore not required to synthesize an immobilized catalyst in order to reduce costs by reusing the catalyst.

In order that the invention may be readily understood and put into practical effect, particular embodiments will now be described by way of the following non-limiting examples.

EXEMPLARY EMBODIMENTS OF THE INVENTION

Material

Figure 5:
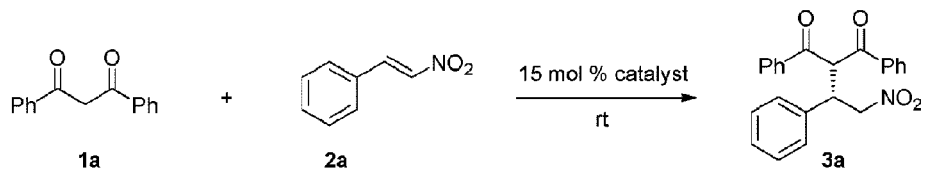
FIG. 5 shows examples and data of an organocatalytic asymmetric Michael addition of (1a) and trans-β-nitrostyrene. Unless otherwise specified, the reaction was carried out with dione 1a (3 eq.) and nitrostyrene 2a (0.1 mmol, 1 eq.) dissolved in solvent (0.3 mL) in the presence of 15 mol % of catalyst at room temperature. [b] Isolated yields. [c] Enantiomeric excess (ee) was determined by chiral HPLC analysis (Chiralpak AS-H). [d] Reaction at 4° C. [e] 10 mol % catalyst used.

In the initial studies, six Cinchona alkaloid catalysts (FIG. 1) were screened for their catalytic ability to promote the Michael addition reaction of 1a and trans-b-nitrostyrene (2a) (FIG. 5). A survey of solvents revealed that all the reactions proceeded smoothly and completed within 17 h at room temperature. Reactions conducted in THF, toluene and diethyl ether all offered good yields and enantioselectivities (up to 98% ee). Remarkably, the Michael adduct precipitated in solid form in diethyl ether gave the highest ee value. This suggested a route to develop a recyclable and practical methodology to reuse the catalyst and excess reactant.

As shown in (FIG. 5, reaction promoted by catalyst VI gave the highest enantioselectivity and catalyst V (with the double bond reduced) gave a slightly lower ee value. Lowering the reaction temperature to 4° C. or reducing the catalyst loading to 10 mol % prolonged the reaction time and decreased the yield, though the ee value remained the same. Examination of the structures of catalysts I-IV revealed that both the primary amine and the methoxy groups played significant roles in controlling enantioselectivity. The reactions promoted by quinine and cinchonidine which do not contain the primary amine group resulted in very low ee values. Almost racemic adducts were observed for the processes catalyzed by cinchonidine derivatives III and IV, both of which do not contain a methoxy group.

Figure 3C:
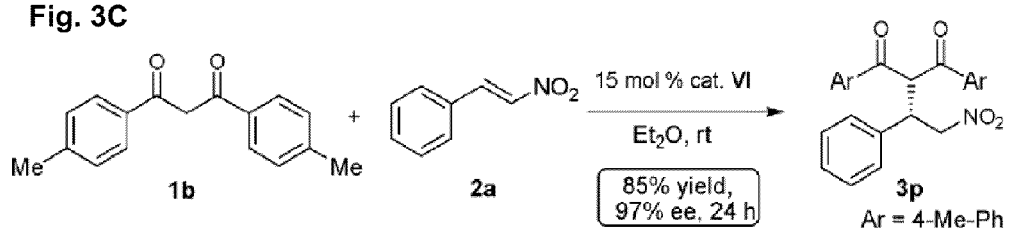
Figure 6:
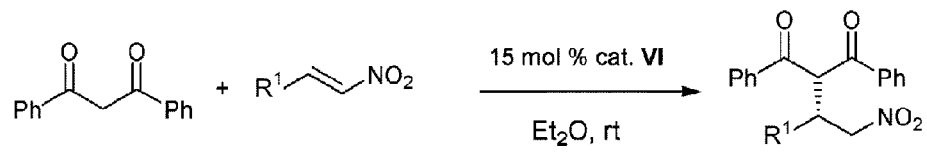
FIG. 6 shows examples and data of a Michael addition of 1a and trans-nitroolefins catalyzed by catalyst VIa.

Having established the optimum reaction conditions for the enantioselective Michael addition of 1a to nitroolefins, a series of analogues bearing various substituents on the aromatic ring (FIG. 6) was screened. All the reactions proceeded smoothly at room temperature (23° C.) in the presence of 15 mol % of catalyst VI and completed within 8-30 h regardless of the electronic properties. The desired adducts were obtained exclusively in yields of 86-97% and excellent enantioselectivity (up to >99%). The nitroolefins bearing either neutral (Entries 1, 11), electron-donating (Entries 2-5), electron withdrawing (Entries 6-7, 12-13) or heterocyclics (Entries 8-10) and containing a variety of substitution (para, meta and ortho) patterns all participated in this reaction efficiently. It is noteworthy that different functional groups on the benzene ring did not affect the results (FIG. 3A), and e.g. substrate 2o shows the great regioselectivity and enantioselectivity of this method (FIG. 3B). Further investigation of the diversity of the Michael donor revealed that different substituents in the 1,3-dione have limited influence on the reactivities and enantioselectivities (FIG. 3C).

Figure 7A:
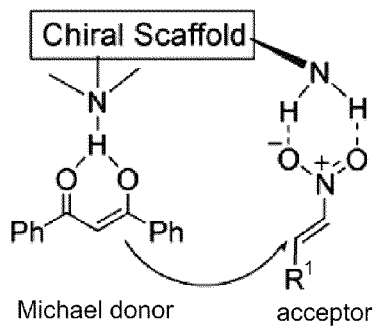
FIG. 7A depicts the proposed action of the catalyst.

According to the dual activation model (Okino et al., 2003, supra; Okino et al., 2005, supra) the two substrates involved in the reaction are activated simultaneously by the catalyst as shown in FIG. 7A. In this model, we predicted the configuration of 3g to be S. The absolute configuration of 3g, which was determined by X-ray analysis, (FIG. 7B, the X-ray crystallographic data deposition number: CCDC 658642) is in accordance with our prediction and the relative structure anticipated from the catalytic mechanism.

Figure 4:
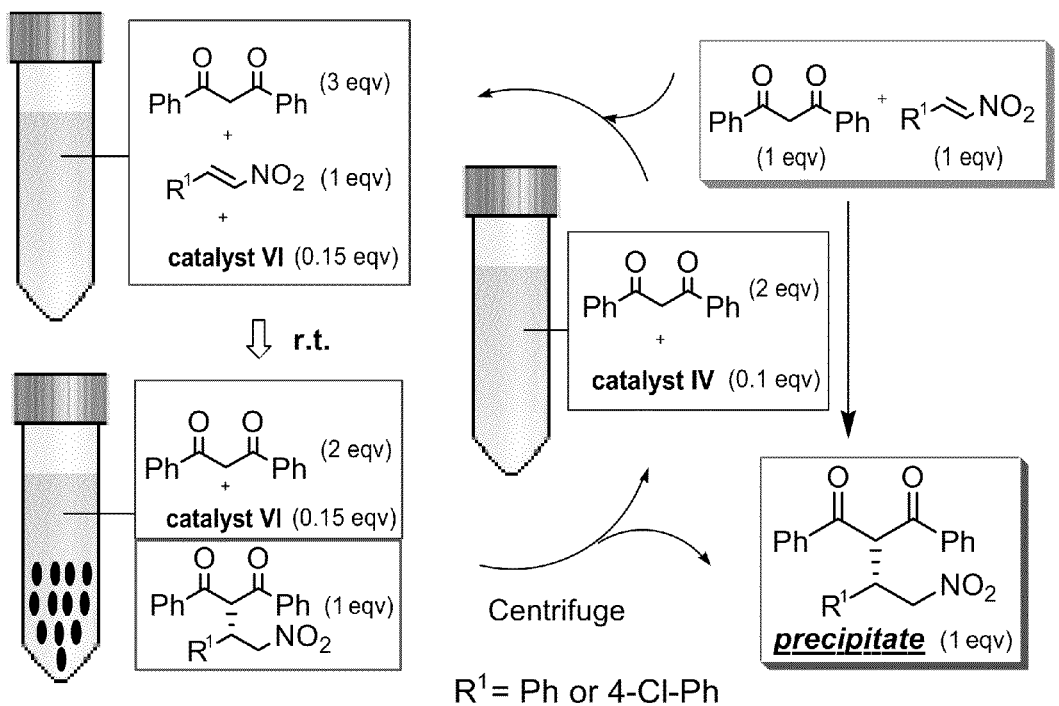
FIG. 4 illustrates an example of the recycling strategy for the organocatalytic Michael addition of the invention.

To examine the validity of recyclable homogenous organocatalysis, the reactions of 1a and nitroolefins (2a and 2g) in diethyl ether were further studied as typical examples using 15 mol % catalyst VI (FIG. 4). Interestingly, the Michael adducts' very poor solubility in diethyl ether could be used to separate organocatalyst VI from the product 3a or 3g by simple filtration since it was precipitated from the reaction solution. The recyclability of the catalyst was tested seven times and amazingly, the catalyst kept its high efficiency, giving almost quantitative yields (average 96%) and excellent enantioselectivities in each cycle (FIG. 8) (see also the examples below). Based on this operationally simple product (precipitate)-catalyst (soluble) separation, the pure product is isolated by filtration from the reaction mixture when the reaction is complete and the catalyst, which is kept in the filtrate, could be reused directly for the next cycle. Hence, the strategy for recyclable homogeneous organocatalysis was developed (FIG. 4).

In summary, the data presented here demonstrate the first example of a highly enantioselective Michael addition reaction with a simple organocatalyst VI. 9-Amino-9-deoxyepiquinine (VI) has been successfully employed as a catalyst in the Michael additions of 1,3-diaryl-1,3-propanedione to various nitroolefins, where the diketone is usually not a good donor. The reactions proceeded smoothly at room temperature, giving high to excellent yields (81-97%) and excellent enantioselectivities (90 to >99% ee). Exploiting the use of the insolubility of the adduct, product (precipitate)-catalyst (soluble) separation significantly simplified the separation and purification process, and allowed the reaction to be recyclable. Such reactions may be applicable to large scale industrial production and thus greatly reduce the cost of catalyst preparation.

EXAMPLES

General Information

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography was performed using Merck silica gel 60 with freshly distilled solvents. Columns were typically packed as slurry and equilibrated with the appropriate solvent system prior to use.

Proton nuclear magnetic resonance spectra ($^1$H NMR) were recorded on Bruker AMX 400 spectrophotometer (CDCl$_3$ as solvent). Chemical shifts for $^1$H NMR spectra are reported as δ in units of parts per million (ppm) downfield from SiMe$_4$ (δ 0.0) and relative to the signal of chloroform-d (δ 7.26, singlet). Multiplicities were given as: s (singlet), d (doublet), t (triplet), dd (doublets of doublet) or m (multiplets). Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.0, triplet).

Enantioselectivities were determined by High performance liquid chromatography (HPLC) analysis employing a Daicel Chirapak AD-H or AS-H column. Optical rotations were measured in CH$_2$Cl$_2$ on a Schmidt+Haensch polarimeter (Polartronic MH8) with a 10 cm cell (c given in g/100 mL). Absolute configuration of the products was determined by comparison with compounds previously published.

High resolution mass spectrometry (HRMS) was recorded on Finnigan MAT 95×P spectrometer.

Example 1

General experimental procedure for the Michael addition of 1,3-diphenyl-1,3-propanedione to nitroolefins To a solution of 1,3-diphenyl-1,3-propanedione (67.2 mg, 0.3 mmol, 3 eq) and nitroolefin (0.1 mmol, 1 eq) in diethyl ether (0.3 mL) was added catalyst VI (Q-NH$_2$) (0.015 mmol, 0.15 eq). The resulting mixture was stirred at room temperature (23° C.). After the reaction was complete (monitored by TLC), the products were isolated and purified either by filtration/washing with diethyl or by flash chromatography over silica gel (EtOAc:Hexane=1:10 to 1:3).

Reactions using catalyst VII (see FIG. 8B) were carried out according to the same procedure with a catalyst loading of 10 mol % (rather than 15 mol % as for catalyst VI.)

In the following exemplary data on the reaction of a series of nitroolefins with 1,3-diphenyl-1,3-propanedione are provided. Following the foregoing protocol products were obtained, isolated and characterized.

(S)-2-(2-Nitro-1-phenylethyl)-1,3-diphenylpropane-1,3-dione (3a)

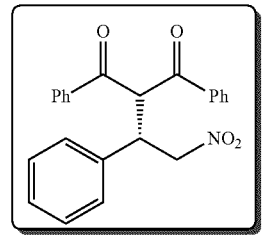

Prepared according to the general procedure to provide the title compound (96% yield).

$^1$H-NMR (400 MHz, CDCl$_3$) δ 7.89 (d, J=8.0 Hz, 2H), 7.81 (d, J=7.6 Hz, 2H), 7.59-7.51 (m, 2H), 7.43-7.37 (m, 3H), 7.27-7.19 (m, 6H), 5.85 (d, J=8.0 Hz, 1H), 5.03-5.01 (m, 2H), 4.64 (dd, J=7.2, 14.4 Hz, 1H).

$^{13}$C-NMR (100 MHz, CDCl$_3$) δ 194.2, 193.6, 136.8, 136.2, 135.8, 134.1, 133.8, 128.97, 128.96, 128.8, 128.8, 128.6, 128.3, 128.2, 77.3, 59.9, 44.0.

HPLC: Chiralpak AS-H (hexane/i-PrOH=85/15, flow rate 1 mL/min, λ=210 nm), t$_R$ (major)=20.4 min, t$_R$ (minor)=28.3 min; 98% ee.

[α]$_D^{25}$=21.3 (c=1.0, CH$_2$Cl$_2$).

MS (ESI, m/z): 374.3 (M+H).

(S)-2-(1-(4-Methoxyphenyl)-2-nitroethyl)-1,3-diphenylpropane-1,3-dione (3b)

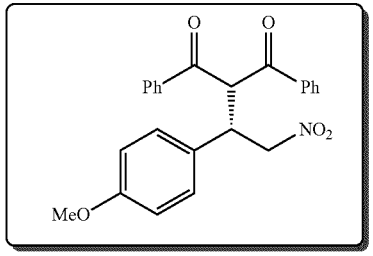

Prepared according to the general procedure to provide the title compound (92% yield).

$^1$H-NMR (400 MHz, CDCl$_3$) δ 7.91 (d, J=7.6 Hz, 2H), 7.81 (d, J=7.6 Hz, 2H), 7.57-7.51 (m, 2H), 7.44-7.36 (m, 4H), 7.17 (d, J=8.8 Hz, 2H), 6.74 (d, J=8.8 Hz, 2H), 5.84 (d, J=8.0 Hz, 1H), 5.00-4.96 (m, 2H), 4.61 (dd, J=7.2, 14.4 Hz, 1H), 3.72 (s, 3H).

$^{13}$C-NMR (100 MHz, CDCl$_3$) δ 194.3, 193.7, 159.3, 136.2, 135.9, 134.1, 133.8, 129.4, 129.0, 128.84, 128.81, 128.6, 128.5, 114.3, 77.7, 60.1, 55.2, 43.5.

HPLC: Chiralpak AD-H (hexane/i-PrOH=70/30, flow rate 1 mL/min, λ=230 nm), $t_R$ (major)=10.7 min, $t_R$ (minor)=22.5 min; 97% ee.

$[α]_D^{25}$=25.1 (c=1.0, CH$_2$Cl$_2$).

MS (ESI, m/z): 404.1 (M+H).

(S)-2-(1-(3-Methoxyphenyl)-2-nitroethyl)-1,3-diphenylpropane-1,3-dione (3c)

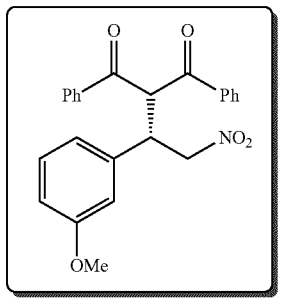

Prepared according to the general procedure to provide the title compound (91% yield).

$^1$H-NMR (400 MHz, CDCl$_3$) δ 7.89 (d, J=8.0 Hz, 2H), 7.82 (d, J=8.0 Hz, 2H), 7.59-7.52 (m, 2H), 7.44-7.37 (m, 4H), 7.16-7.12 (m, 1H), 6.85-6.71 (m, 3H), 5.85 (d, J=8.0 Hz, 1H), 5.02-4.99 (m, 2H), 4.64-4.58 (m, 1H), 3.70 (s, 3H).

$^{13}$C-NMR (100 MHz, CDCl$_3$) δ 194.3, 193.6, 159.8, 138.3, 136.2, 135.8, 134.1, 133.8, 130.0, 128.8, 128.8, 128.6, 128.1, 120.3, 114.3, 113.6, 77.2, 59.7, 55.2, 44.0.

HPLC: Chiralpak AD-H (hexane/i-PrOH=85/15, flow rate 1 mL/min, λ=220 nm), $t_R$ (major)=19.2 min, $t_R$ (minor)=32.5 min; 93% ee.

$[α]_D^{25}$=5.1 (c=1.1, CH$_2$Cl$_2$).

HRMS (EI) calcd for C$_{24}$H$_{21}$NO$_5$, m/z 403.1414. found 403.1412.

(S)-2-(1-(2-Methoxyphenyl)-2-nitroethyl)-1,3-diphenylpropane-1,3-dione (3d)

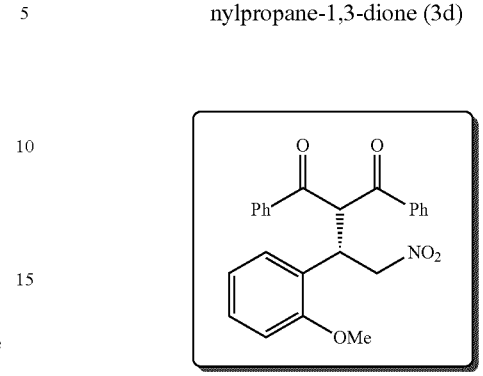

Prepared according to the general procedure to provide the title compound (94% yield).

$^1$H-NMR (400 MHz, CDCl$_3$) δ 7.91-7.87 (m, 4H), 7.55-7.51 (m, 2H), 7.43-7.37 (m, 4H), 7.20-7.13 (m, 2H), 6.81-6.76 (m, 2H), 6.09 (d, J=8.0 Hz, 1H), 5.25 (dd, J=9.6, 12.8 Hz, 1H), 4.94 (dd, J=4.0, 13.2 Hz, 1H), 4.86-4.80 (m, H), 3.87 (s, 3H).

$^{13}$C-NMR (100 MHz, CDCl$_3$) δ 194.4, 194.2, 157.1, 136.4, 136.0, 133.8, 133.7, 131.0, 129.4, 128.9, 128.7, 128.6, 128.6, 124.2, 121.1, 110.9, 75.8, 57.2, 55.3, 40.9.

HPLC: Chiralpak AD-H (hexane/i-PrOH=85/15, flow rate 1 mL/min, λ=210 nm), $t_R$ (major)=16.7 min, $t_R$ (minor)=23.5 min; 99% ee.

$[α]_D^{25}$=−17.4 (c=1.0, CH$_2$Cl$_2$).

HRMS (EI) calcd for C$_{24}$H$_{21}$NO$_5$, m/z 403.1414. found 403.1414.

(S)-2-(2-Nitro-1-p-tolylethyl)-1,3-diphenylpropane-1,3-dione (3e)

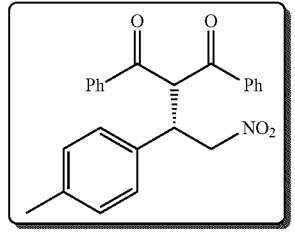

Prepared according to the general procedure to provide the title compound (93% yield).

$^1$H-NMR (400 MHz, CDCl$_3$) δ 7.90 (d, J=7.6 Hz, 2H), 7.81 (d, J=7.6 Hz, 2H), 7.57-7.52 (m, 2H), 7.44-7.37 (m, 4H), 7.14 (d, J=8.0 Hz, 2H), 7.03 (d, J=7.6 Hz, 2H), 5.85 (d, J=8.0 Hz, 1H), 5.00-4.98 (m, 2H), 4.62 (dd, J=5.2, 8.0 Hz, 1H), 2.25 (s, 3H).

$^{13}$C-NMR (100 MHz, CDCl$_3$) δ 194.3, 193.6, 137.9, 136.2, 135.9, 134.1, 133.8, 133.7, 129.6, 129.0, 128.83, 128.81, 128.7, 128.1, 77.5, 60.1, 43.7, 21.0.

HPLC: Chiralpak AS-H (hexane/i-PrOH=85/15, flow rate 1 mL/min, λ=210 nm), $t_R$ (major)=18.8 min, $t_R$ (minor)=25.5 min; 98% ee.

$[α]_D^{25}$=8.6 (c=1.0, CH$_2$Cl$_2$).

MS (ESI, m/z): 388.3 (M+H).

(S)-2-(1-(4-Bromophenyl)-2-nitroethyl)-1,3-diphenylpropane-1,3-dione (3f)

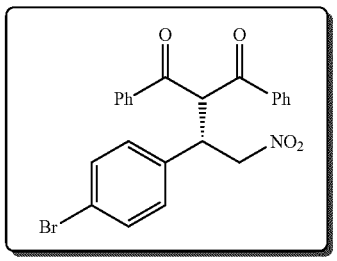

Prepared according to the general procedure to provide the title compound (93% yield).

$^1$H-NMR (400 MHz, CDCl$_3$) δ 7.87-7.85 (m, 2H), 7.77-7.74 (m, 2H), 7.59-7.52 (m, 2H), 7.54-7.47 (m, 2H), 7.41-7.29 (m, 6H), 7.11-7.08 (m, 2H), 5.78 (d, J=10.8 Hz, 1H), 4.93-4.90 (m, 2H), 4.57 (dd, J=7.2, 19.6 Hz, 1H).

$^{13}$C-NMR (100 MHz, CDCl$_3$) δ 194.0, 193.3, 136.0, 135.8, 135.7, 134.3, 134.0, 132.1, 130.0, 129.1, 129.0, 128.8, 128.6, 122.3, 77.2, 59.6, 43.6.

HPLC: Chiralpak AS-H (hexane/i-PrOH=85/15, flow rate 1 mL/min, λ=210 nm), t$_R$ (major)=23.8 min, t$_R$ (minor)=33.5 min; >99% ee.

[α]$_D^{25}$=17.8 (c=1.3, CH$_2$Cl$_2$).

MS (ESI, m/z): 453.3 (M+H).

(S)-2-(1-(4-Chlorophenyl)-2-nitroethyl)-1,3-diphenylpropane-1,3-dione (3g)

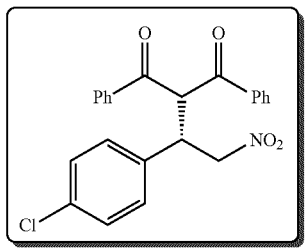

Prepared according to the general procedure to provide the title compound (97% yield).

$^1$H-NMR (400 MHz, CDCl$_3$) δ 7.88-7.85 (m, 2H), 7.77-7.74 (m, 2H), 7.54-7.48 (m, 2H), 7.41-7.32 (m, 4H), 7.15 (m, 4H), 5.78 (d, J=10.8 Hz, 1H), 4.93-4.91 (m, 2H), 4.57 (dd, J=7.2, 19.2 Hz, 1H).

$^{13}$C-NMR (100 MHz, CDCl$_3$) δ 194.0, 193.4, 136.0, 135.7, 135.3, 134.3, 134.1, 134.0, 129.7, 129.2, 129.1, 129.0, 128.8, 128.6, 77.3, 59.7, 43.5.

HPLC: Chiralpak AS-H (hexane/i-PrOH=85/15, flow rate 1 mL/min, λ=210 nm), t$_R$ (major)=22.1 min, t$_R$ (minor)=31.2 min; >99% ee.

[α]$_D^{25}$=18.9 (c=1.2, CH$_2$Cl$_2$).

HRMS (EI) calcd for C$_{23}$H$_{18}$ClNO$_4$, m/z 407.0919. found 407.0912.

(R)-2-(2-Nitro-1-(thiophen-2-yl)ethyl)-1,3-diphenylpropane-1,3-dione (3h)

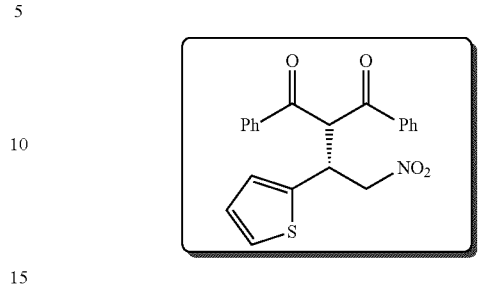

Prepared according to the general procedure to provide the title compound (92% yield).

$^1$H-NMR (400 MHz, CDCl$_3$) δ 7.91-7.87 (m, 4H), 7.60-7.56 (m, 2H), 7.45-7.41 (m, 4H), 7.15 (d, J=5.2 Hz, 1H), 6.90 (d, J=3.2 Hz, 1H), 6.82 (dd, J=3.6, 5.2 Hz, 1H), 5.98 (d, J=7.2 Hz, 1H), 5.03-5.00 (m, 2H), 4.92 (dd, J=6.8, 12.8 Hz, 1H).

$^{13}$C-NMR (100 MHz, CDCl$_3$) δ 194.0, 193.5, 139.3, 136.0, 135.6, 134.1, 134.0, 129.0, 128.96, 128.73, 128.68, 127.2, 127.1, 125.4, 78.0, 59.9, 39.5.

HPLC: Chiralpak AS-H (hexane/i-PrOH=85/15, flow rate 1 mL/min, λ=262 nm), t$_R$ (major)=23.4 min, t$_R$ (minor)=27.0 min; 97% ee.

[α]$_D^{25}$=−15.6 (c=1.4, CH$_2$Cl$_2$).

MS (ESI, m/z): 380.4 (M+H).

(R)-2-(1-(Furan-2-yl)-2-nitroethyl)-1,3-diphenylpropane-1,3-dione (3i)

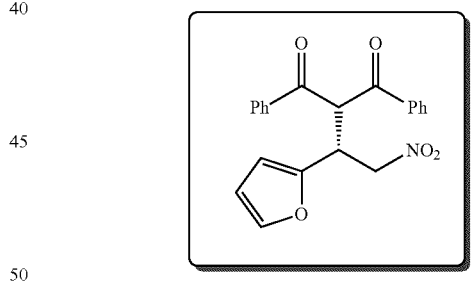

Prepared according to the general procedure to provide the title compound (91% yield).

$^1$H-NMR (400 MHz, CDCl$_3$) δ 7.89-7.85 (m, 4H), 7.58-7.55 (m, 2H), 7.45-7.39 (m, 4H), 7.23 (m, 1H), 6.13 (m, 2H), 6.04 (d, J=7.6 Hz, 1H), 5.01-4.90 (m, 2H), 4.77-4.72 (m, 1H).

$^{13}$C-NMR (100 MHz, CDCl$_3$) δ 193.7, 149.8, 142.5, 135.9, 135.4, 134.1, 133.9, 129.0, 128.9, 128.6, 110.7, 108.9, 75.6, 56.7, 37.8.

HPLC: Chiralpak AS-H (hexane/i-PrOH=85/15, flow rate 1 mL/min, λ=210 nm), t$_R$ (minor)=20.7 min, t$_R$ (major)=25.1 min; 98% ee.

[α]$_D^{25}$=38.5 (c=1.1, CH$_2$Cl$_2$).

MS (ESI, m/z): 364.5 (M+H).

(S)-2-(1-(Furan-3-yl)-2-nitroethyl)-1,3-diphenylpropane-1,3-dione (3j)

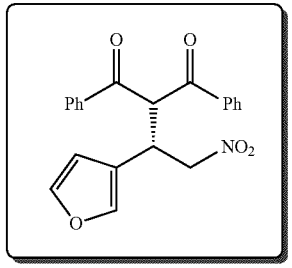

Prepared according to the general procedure to provide the title compound (91% yield).

$^1$H-NMR (400 MHz, CDCl$_3$) δ 7.94 (d, J=7.6 Hz, 2H), 7.88 (d, J=7.6 Hz, 2H), 7.60-7.57 (m, 2H), 7.46-7.42 (m, 4H), 7.28-7.21 (m, 2H), 6.32 (s, 1H), 5.88 (d, J=8.0 Hz, 1H), 4.92-4.86 (m, 2H), 4.61 (dd, J=6.8, 13.6 Hz, 1H).

$^{13}$C-NMR (100 MHz, CDCl$_3$) δ 194.2, 193.9, 143.6, 140.9, 136.0, 135.8, 134.1, 134.0, 129.0, 129.0, 128.7, 128.6, 121.0, 109.7, 77.5, 58.7, 35.3.

HPLC: Chiralpak AS-H (hexane/i-PrOH=85/15, flow rate 1 mL/min, λ=210 nm), $t_R$ (major)=24.5 min, $t_R$ (minor)=27.7 min; 96% ee.

$[α]_D^{25}$=74.6 (c=1.0, CH$_2$Cl$_2$).

MS (ESI, m/z): 364.4 (M+H).

(S)-2-(1-(Naphthalen-1-yl)-2-nitroethyl)-1,3-diphenylpropane-1,3-dione (3k)

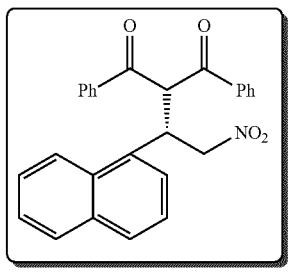

Prepared according to the general procedure to provide the title compound (88% yield).

$^1$H-NMR (400 MHz, CDCl$_3$) δ 8.20 (d, J=8.4 Hz, 2H), 7.86 (d, J=7.6 Hz, 2H), 7.75-7.60 (m, 6H), 7.56-7.40 (m, 3H), 7.33-7.28 (m, 5H), 7.22-7.18 (m, 1H), 6.02 (d, J=6.0 Hz, 1H), 5.66-5.61 (m, 1H), 5.31 (dd, J=4.0, 14.4 Hz, 1H), 4.61 (dd, J=9.2, 14.0 Hz, 1H).

$^{13}$C-NMR (100 MHz, CDCl$_3$) δ 195.0, 193.8, 136.2, 135.7, 134.2, 133.7, 132.8, 131.1, 129.3, 128.9, 128.8, 128.8, 128.5, 127.1, 126.1, 124.9, 122.4, 76.5, 58.5, 37.3.

HPLC: Chiralpak AS-H (hexane/i-PrOH=85/15, flow rate 1 mL/min, λ=210 nm), $t_R$ (major)=21.8 min, $t_R$ (minor)=29.6 min; 96% ee.

$[α]_D^{25}$=−155.4 (c=1.0, CH$_2$Cl$_2$).

HRMS (EI) calcd for C$_{27}$H$_{21}$NO$_4$, m/z 423.1465. found 423.1466.

(S)-2-(2-Nitro-1-(2-nitrophenyl)ethyl)-1,3-diphenylpropane-1,3-dione (3l)

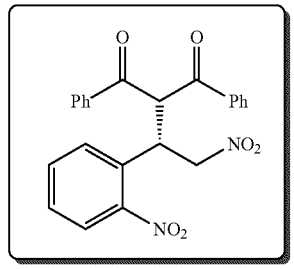

Prepared according to the general procedure to provide the title compound (92% yield).

$^1$H-NMR (400 MHz, CDCl$_3$) δ 7.89-7.84 (m, 5H), 7.60-7.52 (m, 2H), 7.43-7.36 (m, 7H), 6.28 (d, J=6.0 Hz, 1H), 5.28-5.26 (m, 1H), 5.12-5.09 (m, 2H).

$^{13}$C-NMR (100 MHz, CDCl$_3$) δ 194.4, 193.4, 150.0, 136.2, 135.6, 134.3, 133.2, 131.7, 130.1, 129.1, 129.1, 128.9, 128.9, 128.6, 128.6, 125.4, 75.1, 58.0, 439.0.

HPLC: Chiralpak AS-H (hexane/i-PrOH=85/15, flow rate 1 mL/min, λ=210 nm), $t_R$ (minor)=16.0 min, $t_R$ (major)=18.0 min; 94% ee.

$[α]_D^{25}$=−81.4 (c=1.1, CH$_2$Cl$_2$).

MS (ESI, m/z): 419.4 (M+H).

(S)-2-(2-Nitro-1-(4-nitrophenyl)ethyl)-1,3-diphenylpropane-1,3-dione (3m)

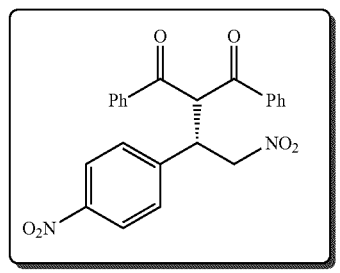

Prepared according to the general procedure to provide the title compound (86% yield).

$^1$H-NMR (400 MHz, CDCl$_3$) δ 8.09 (d, J=8.4 Hz, 2H), 7.93 (d, J=7.6 Hz, 2H), 7.82-7.80 (m, 2H), 7.61-7.54 (m, 2H), 7.49-7.39 (m, 6H), 5.87 (d, J=6.0 Hz, 1H), 5.02-5.00 (m, 2H), 4.78 (dd, J=7.6 Hz, 14.0 Hz, 1H).

$^{13}$C-NMR (100 MHz, CDCl$_3$) δ 193.5, 192.9, 147.6, 144.2, 135.8, 135.4, 134.5, 134.3, 129.5, 129.2, 129.1, 128.8, 128.6, 124.1, 76.8, 59.3, 43.7.

HPLC: Chiralpak AS-H (hexane/i-PrOH=85/15, flow rate 1 mL/min, λ=210 nm), $t_R$ (major)=20.5 min, $t_R$ (minor)=28.1 min; 94% ee.

$[α]_D^{25}$=36.8 (c=1.1, CH$_2$Cl$_2$).

MS (ESI, m/z): 419.4 (M+H).

2-((S)-1-(2-Ethynylphenyl)-2-nitroethyl)-1,3-diphenylpropane-1,3-dione (3n)

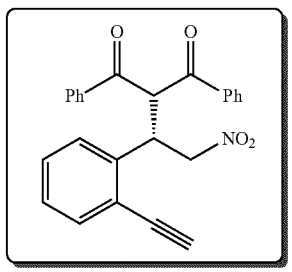

Prepared according to the general procedure to provide the title compound (87% yield).

$^1$H-NMR (400 MHz, CDCl$_3$) δ 7.91 (d, J=7.5 Hz, 2H), 7.83 (d, J=7.5, 2H), 7.57-7.52 (m, 3H), 7.40-7.37 (m, 4H), 7.18-7.13 (m, 3H), 6.23 (d, J=7.0 Hz, 1H), 5.26 (dd, J=10.5, 14.5 Hz, 1H), 5.15-5.11 (m, 2H), 3.5 (s, 1H).

$^{13}$C-NMR (100 MHz, CDCl$_3$) δ 194.5, 193.6, 139.1, 136.3, 135.7, 134.2, 134.1, 133.9, 129.4, 129.0, 128.8, 128.7, 128.7, 127.9, 121.5, 83.7, 81.8, 75.7, 57.7, 42.0.

HPLC: Chiralpak AD-H (hexane/i-PrOH=85/15, flow rate 1 mL/min, λ=254 nm), $t_R$ (major)=18.7 min, $t_R$ (minor)=21.5 min; 93% ee.

$[α]_D^{25}$=-45.6 (c=1.0, CH$_2$Cl$_2$).

HRMS (ESI) calcd for C$_{25}$H$_{19}$NO$_4$Na, m/z 420.1212. found 420.1209.

2-((R,E)-1-Nitro-4-phenylbut-3-en-2-yl)-1,3-diphenylpropane-1,3-dione (3o)

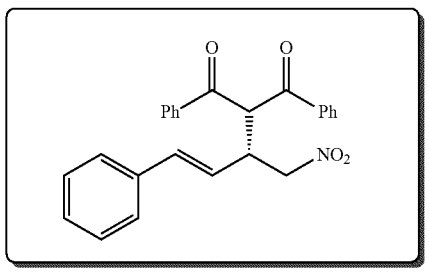

To a solution of 1,3-diphenyl-1,3-propanedione (67.2 mg, 0.3 mmol, 3 eq) and nitroolefin 2o (0.1 mmol, 1 eq) in diethyl ether (0.2 mL) was added catalyst VI (Q-NH$_2$) (0.03 mmol, 0.3 eq). The resulting mixture was stirred at room temperature (23° C.) for 30 hours. The products were isolated and purified with diethyl or by flash chromatography over silica gel (EtOAc:Hexane=1:10 to 1:5) to provide the title compound (81% yield).

$^1$H-NMR (400 MHz, CDCl$_3$) δ 8.00-7.97 (m, 4H), 7.62 (t, J=7.0 Hz, 2H), 7.51-7.47 (dd, J=7.5, 13.5 Hz, 4H), 7.29-7.16 (m, 5H), 6.48 (d, J=15.5 Hz, 1H), 6.20 (dd, J=9.5, 15.5 Hz, 1H), 5.81 (d, J=7.0 Hz, 1H), 4.88-4.80 (m, 2H), 4.06-4.01 (s, 1H).

$^{13}$C-NMR (100 MHz, CDCl$_3$) δ 194.5, 194.3, 136.0, 135.9, 135.3, 134.1, 134.0, 129.2, 129.1, 128.7, 128.5, 128.1, 126.6, 124.3, 77.6, 57.4, 42.4.

HPLC: Chiralpak AS-H (hexane/i-PrOH=85/15, flow rate 1 mL/min, λ=254 nm), $t_R$ (major)=16.4 min, $t_R$ (minor)=42.0 min; 90% ee.

$[α]_D^{25}$=141.1 (c=0.8, CH$_2$Cl$_2$).

HRMS (ESI) calcd for C$_{25}$H$_{21}$NO$_4$Na, m/z 422.1368. found 422.1363.

2-((S)-2-Nitro-1-phenylethyl)-1,3-dip-tolylpropane-1,3-dione (3p)

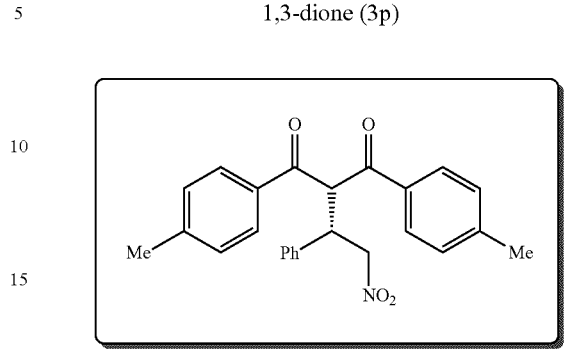

To a solution of dione 1b (0.1 mmol, 1 eq) and trans-β-nitrostyrene 2a (0.2 mmol, 2 eq) in diethyl ether (0.2 mL) was added catalyst VI (Q-NH$_2$) (0.015 mmol, 0.15 eq). The resulting mixture was stirred at room temperature (23° C.) for 24 hours. The product was purified by flash chromatography over silica gel (EtOAc:Hexane=1:10 to 1:5) to provide the title compound (85% yield).

$^1$H-NMR (400 MHz, CDCl$_3$) δ 7.80 (d, J=8.0 Hz, 2H), 7.73 (d, J=8.0 Hz, 2H), 7.28-7.16 (m, 9H), 5.80 (d, J=8.0 Hz, 1H), 5.01 (d, J=6.8 Hz, 2H), 4.64 (dd, J=7.6, 14.4 Hz, 1H), 2.39 (s. 3H), 2.37 (s, 3H).

$^{13}$C-NMR (100 MHz, CDCl$_3$) δ 193.8, 193.1, 145.2, 144.9, 137.0, 133.8, 133.3, 129.7, 129.5, 128.96, 128.93, 128.8, 128.3, 128.1, 59.7, 44.1, 21.7, 21.7.

HPLC: Chiralpak AD-H (hexane/i-PrOH=70/30, flow rate 1 mL/min, λ=254 nm), $t_R$ (major)=10.7 min, $t_R$ (minor)=28.0 min; 97% ee.

$[α]_D^{25}$=-2.6 (c=1.0, CH$_2$Cl$_2$).

HRMS (ESI) calcd for C$_{25}$H$_{21}$NO$_4$, m/z 402.1705. found 402.1692.

Example 2

The procedure for the recycling of the Michael addition of 1,3-diphenyl-1,3-propanedione to trans-β-nitrostyrene (1a) and 1-chloro-4-((E)-2-nitrovinyl)benzene (1g)

Figure 8A:
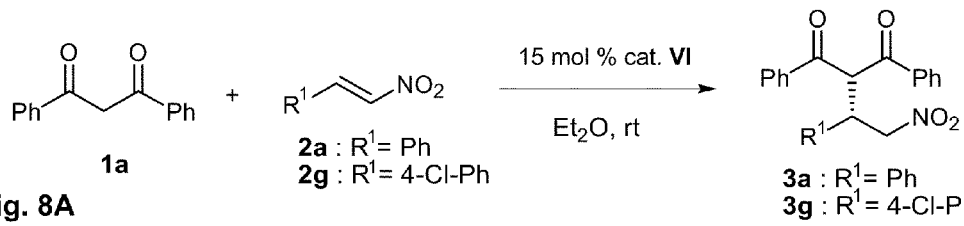
FIG. 8A illustrates the recycling in the organocatalytic Michael addition of 1,3-diphenyl-1,3-propanedione and trans-β-nitrostyrene (left half) or trans-vinyl-4-chloro-benzene (right half) with catalyst VIa. The reaction was carried out using 2a or 2g (0.1 mmol, 1 eq.) and dione 1a (0.3 mmol, 3 eq.) with 15 mol % of VI in cycle 1 and in cycles 2-7 only 2a or 2g (0.1 mmol) and 1 (0.1 mmol) were added. Of the indicated yields the average yield was 96%. Indicated enantiomeric excess (ee) was determined by chiral HPLC analysis.
Figure 8B:
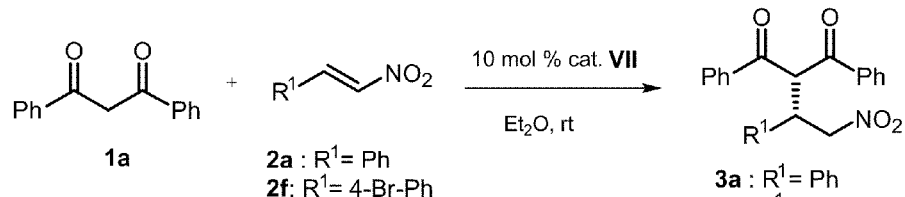
FIG. 8B shows the suitability of the method of the invention for repeated recycling, illustrated with the organocatalytic Michael addition of 1,3-diphenyl-1,3-propanedione and trans-β-nitrostyrene (left half) or trans-vinyl-4-bromo-benzene (right half) using catalyst VII. The reaction was carried out using 2a or 2f (0.1 mmol, 1 eq.) and dione 1a (0.3 mmol, 3 eq.) with 15 mol % of VI in cycle 1 and in cycles 2-10 only 2a or 2f (0.1 mmol) and 1 (0.1 mmol) were added. are given. Indicated enantiomeric excess (ee) was determined by chiral HPLC analysis.
Figure 8C:
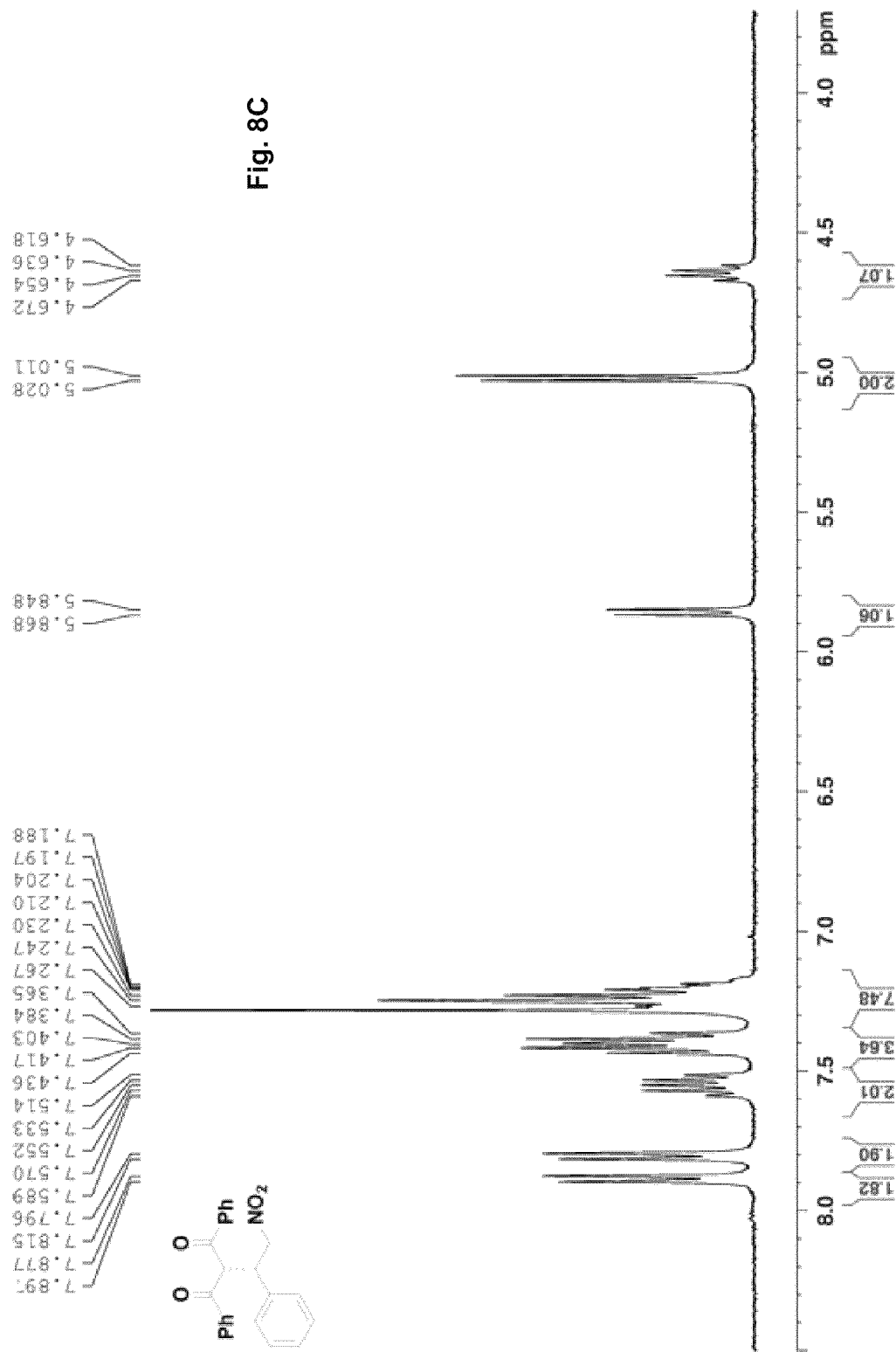
Figure 9A:
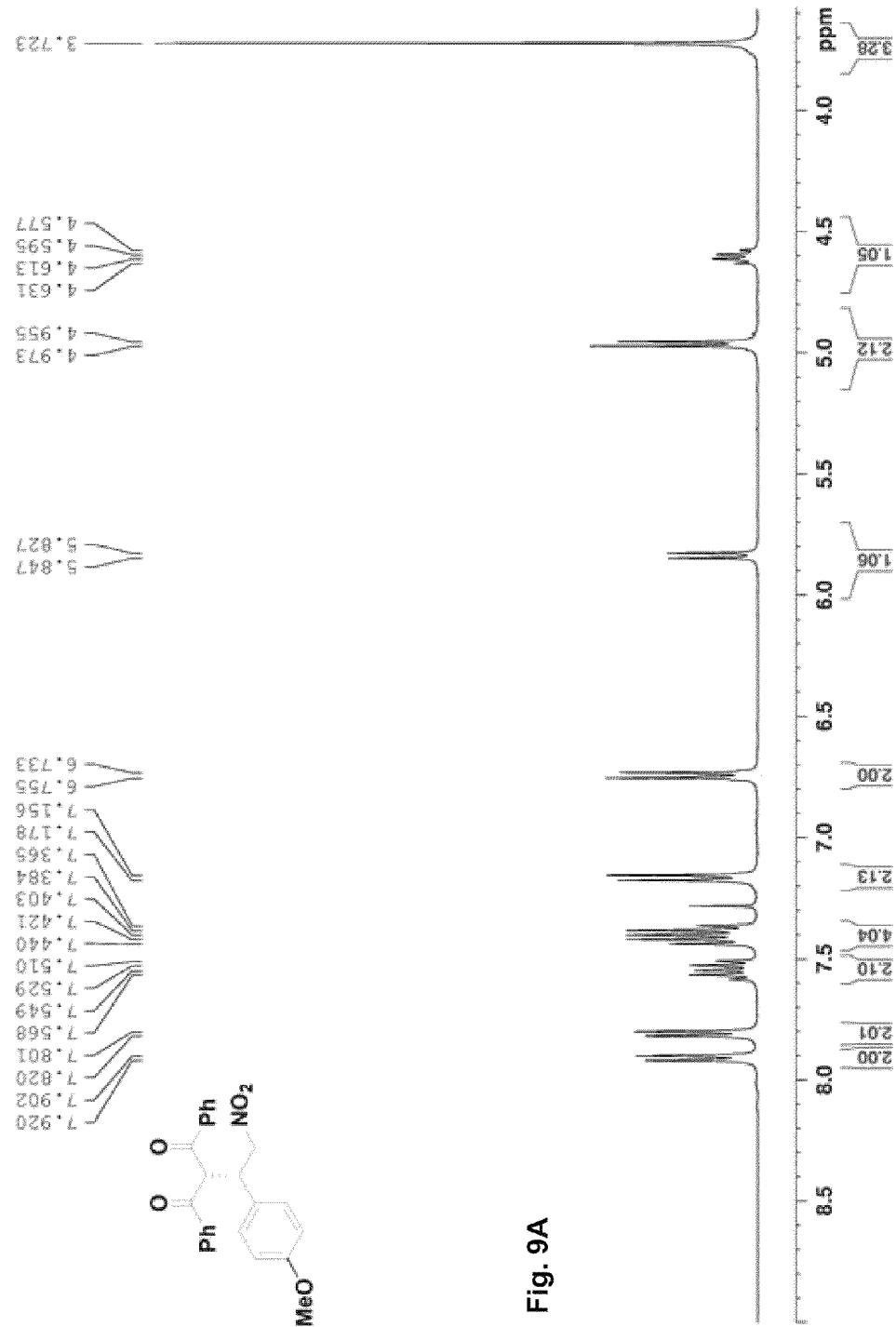
FIG. 9A depicts a $^1$H NMR spectrum and FIG. 9B a $^{13}$C NMR spectrum of compound 3b.
Figure 9B:
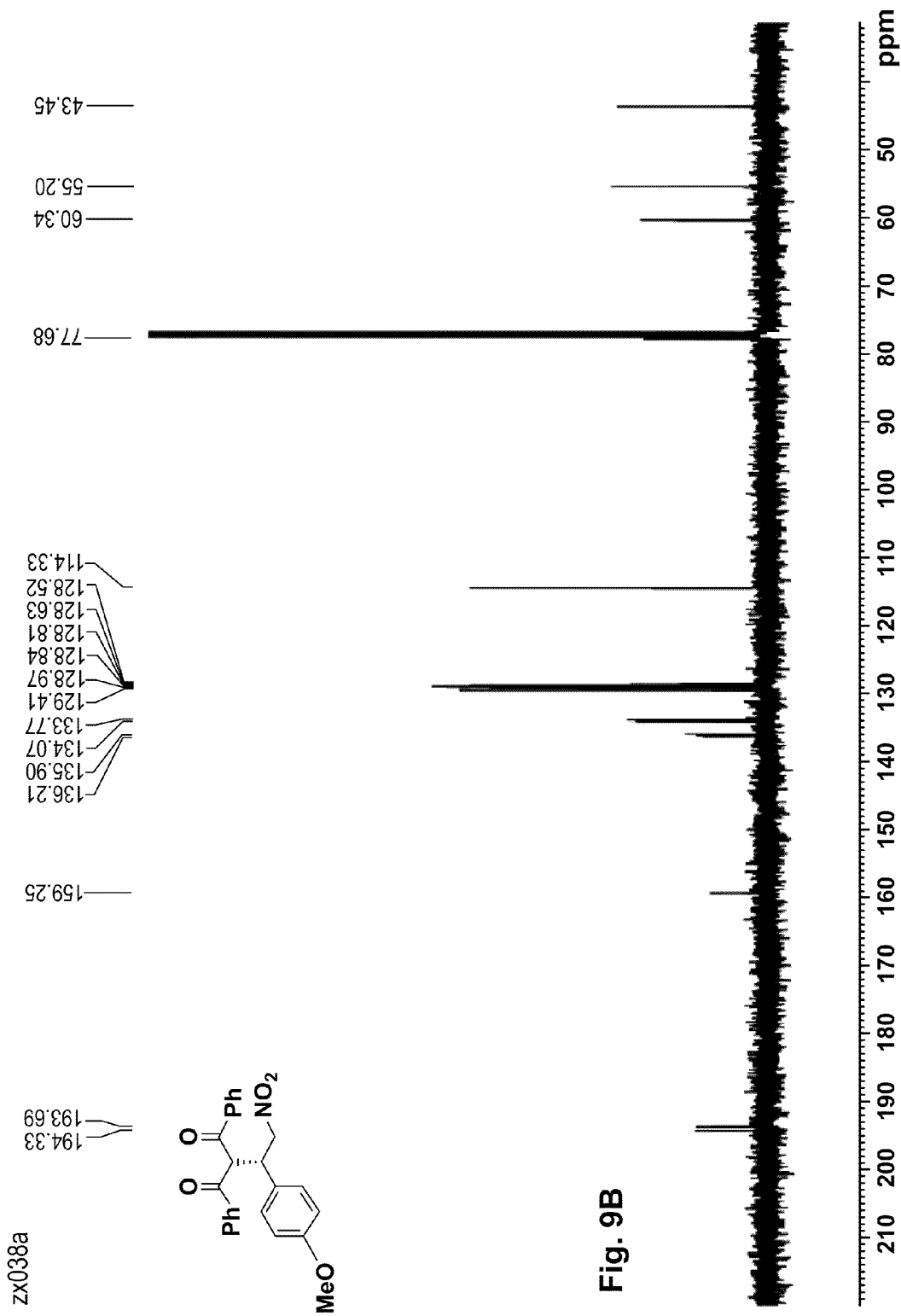
Figure 10A:
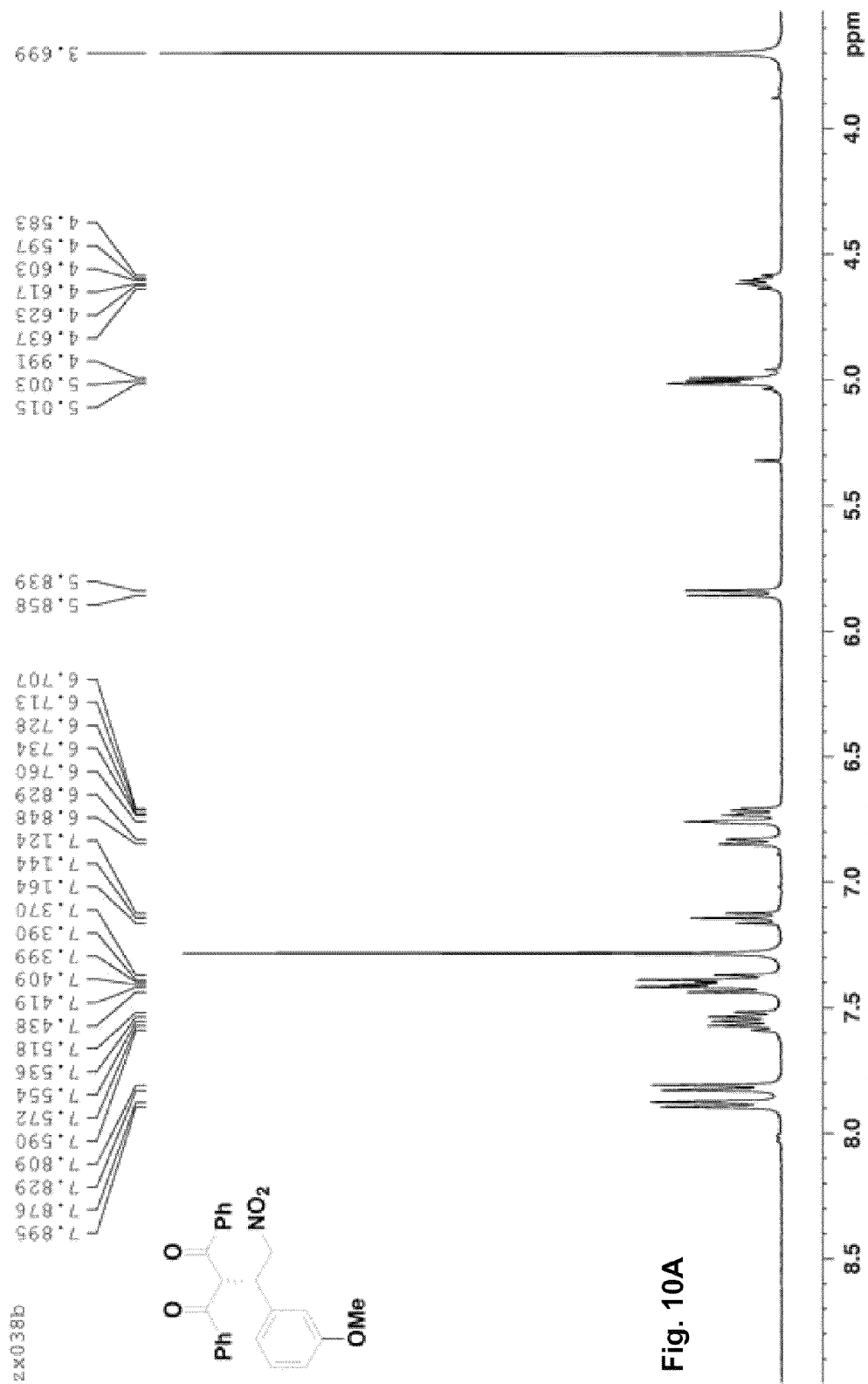
FIG. 10A depicts a $^1$H NMR spectrum and FIG. 10B a $^{13}$C NMR spectrum of compound 3c.
Figure 10B:
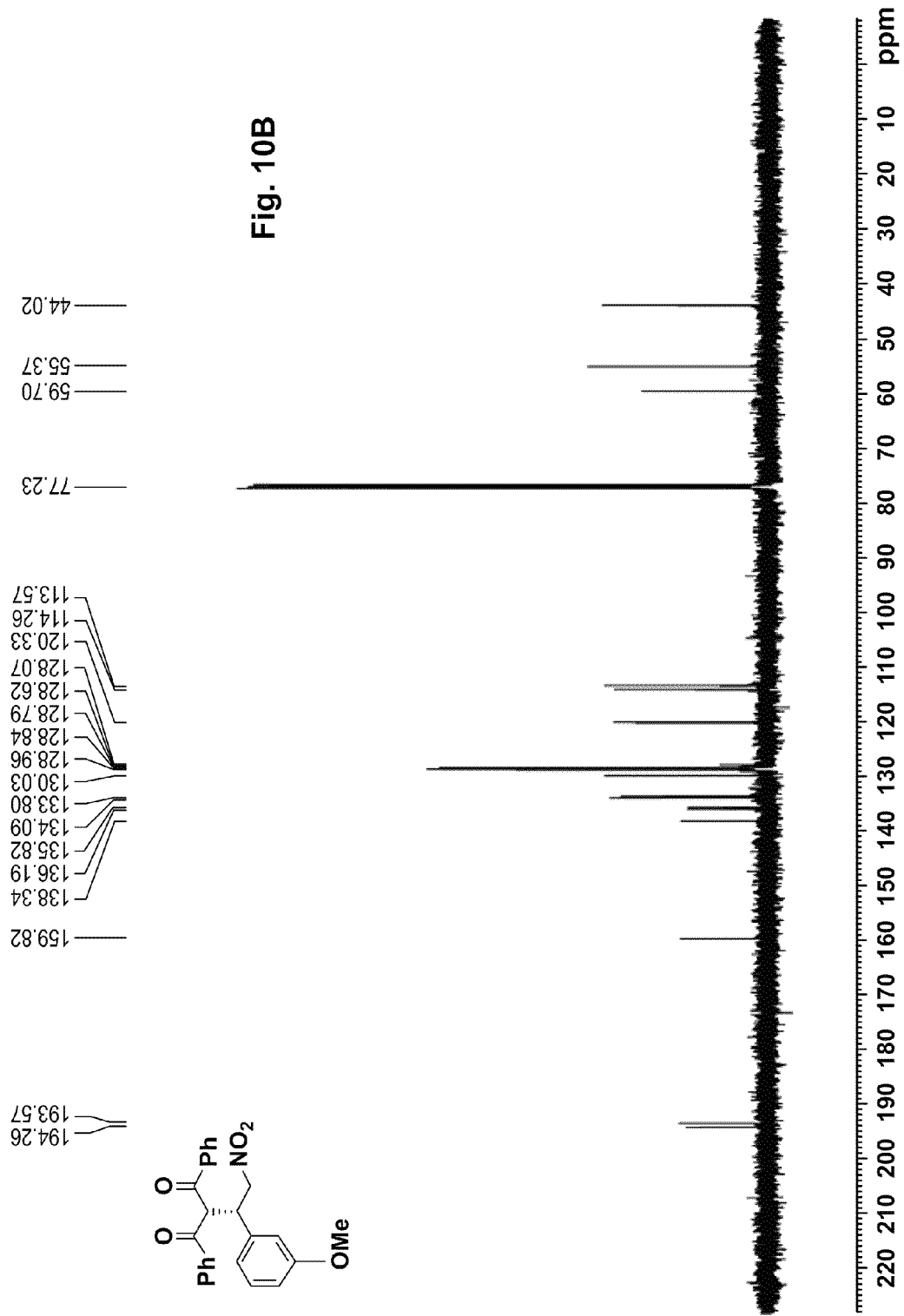
Figure 11A:
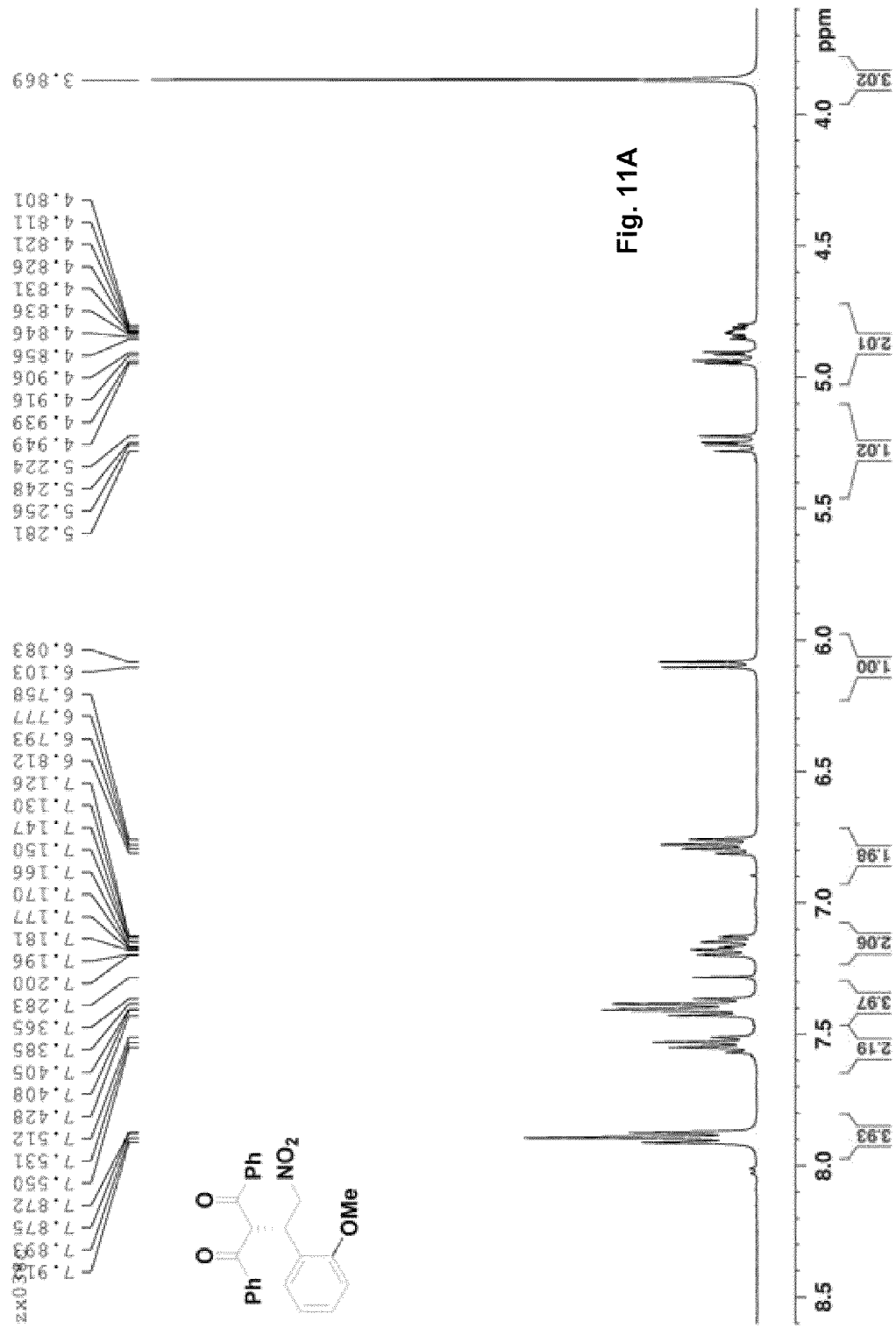
FIG. 11A depicts a $^1$H NMR spectrum and FIG. 11B a $^{13}$C NMR spectrum of compound 3d.
Figure 12A:
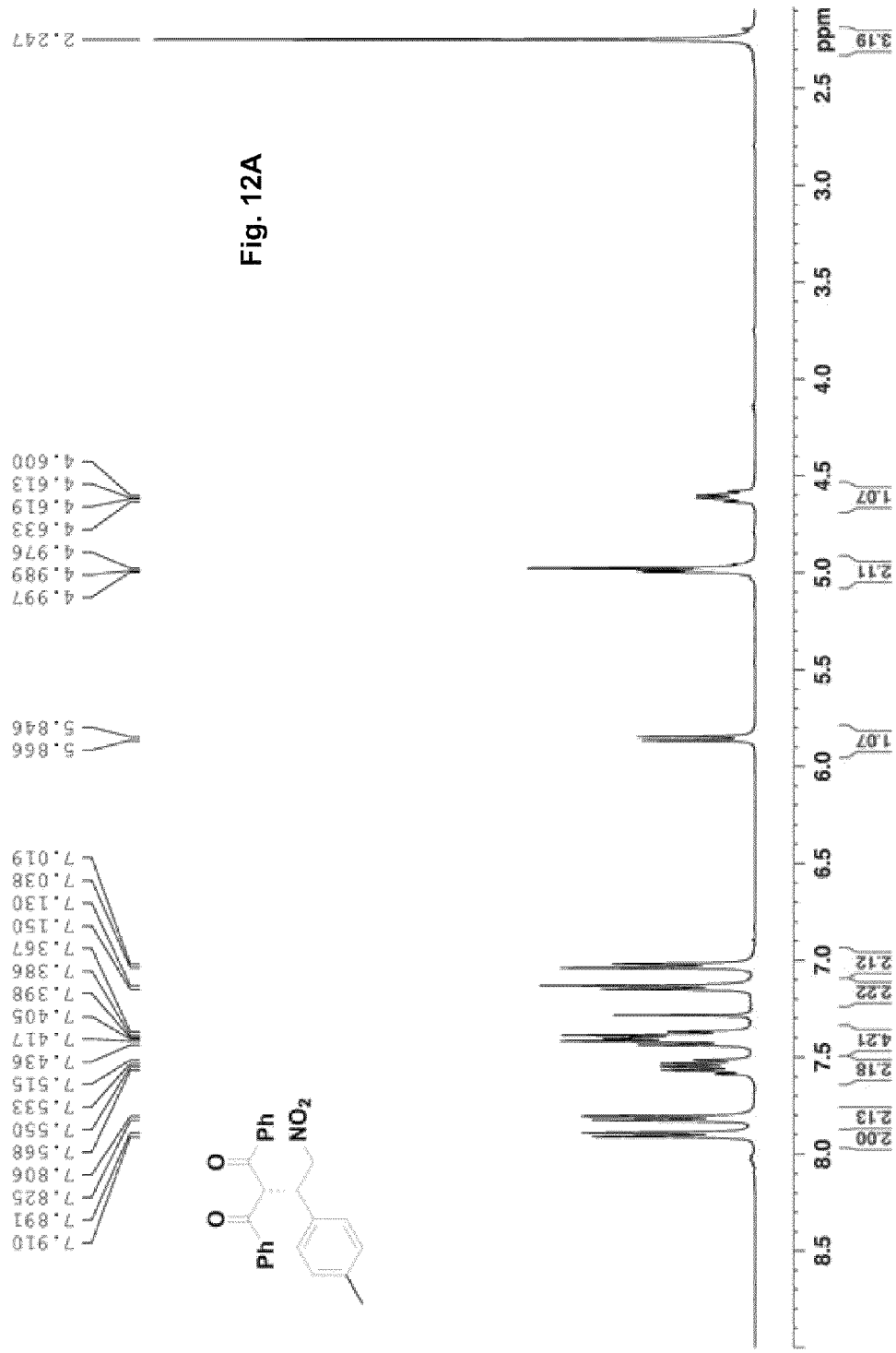
FIG. 12A depicts a $^1$H NMR spectrum and FIG. 12B a $^{13}$C NMR spectrum of compound 3e.
Figure 12B:
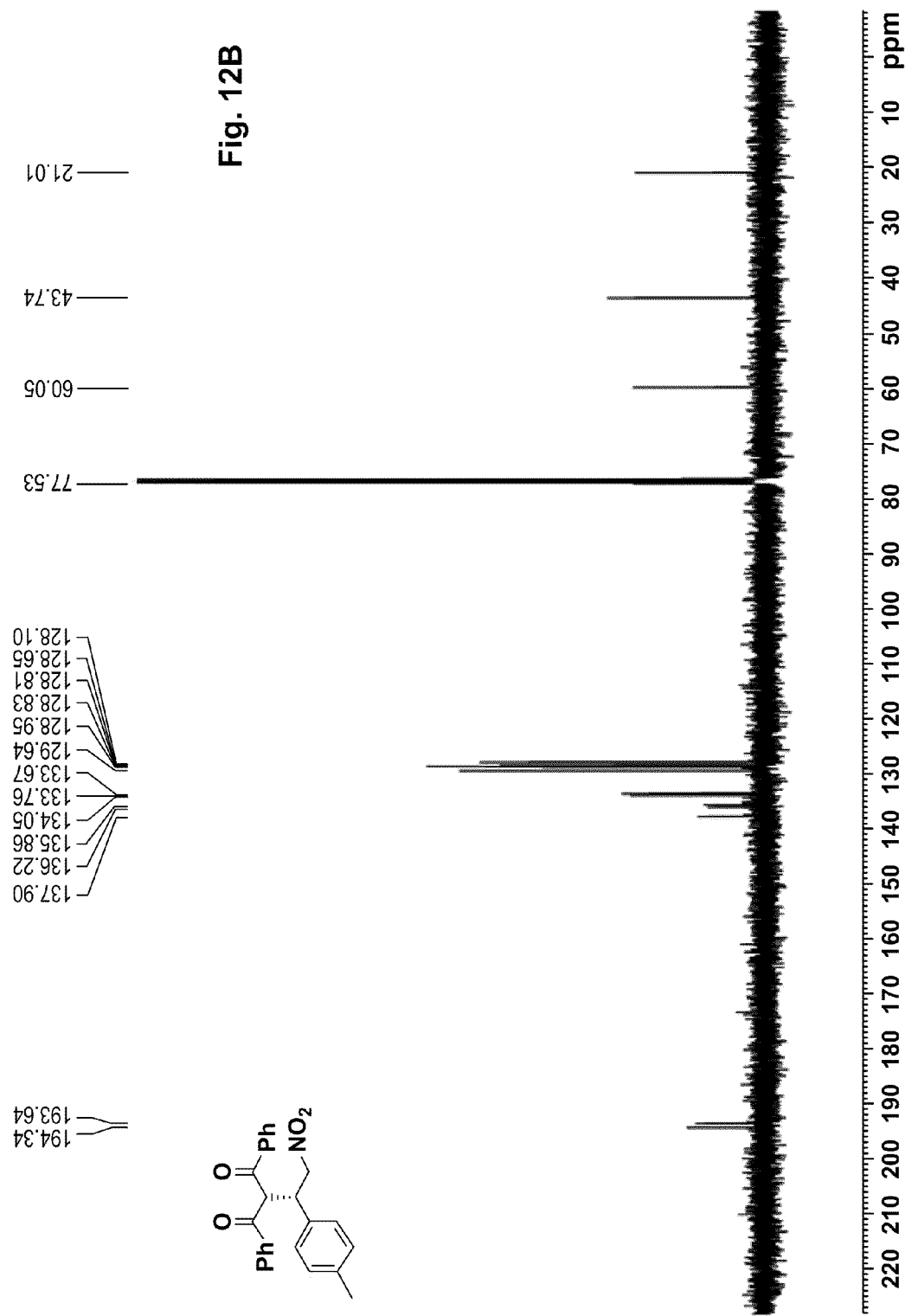
Figure 13A:
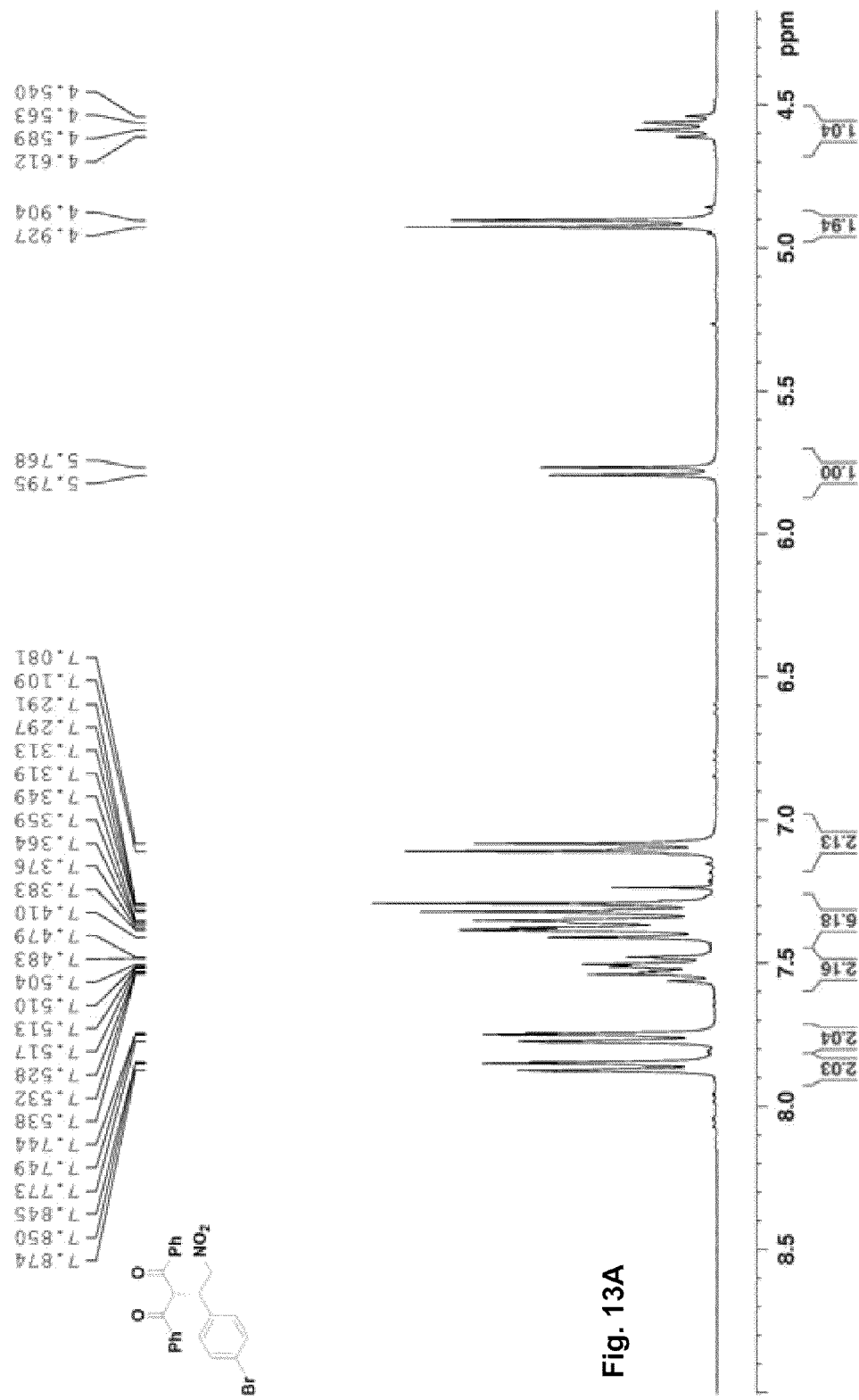
FIG. 13A depicts a $^1$H NMR spectrum and FIG. 13B a $^{13}$C NMR spectrum of compound 3f.
Figure 13B:
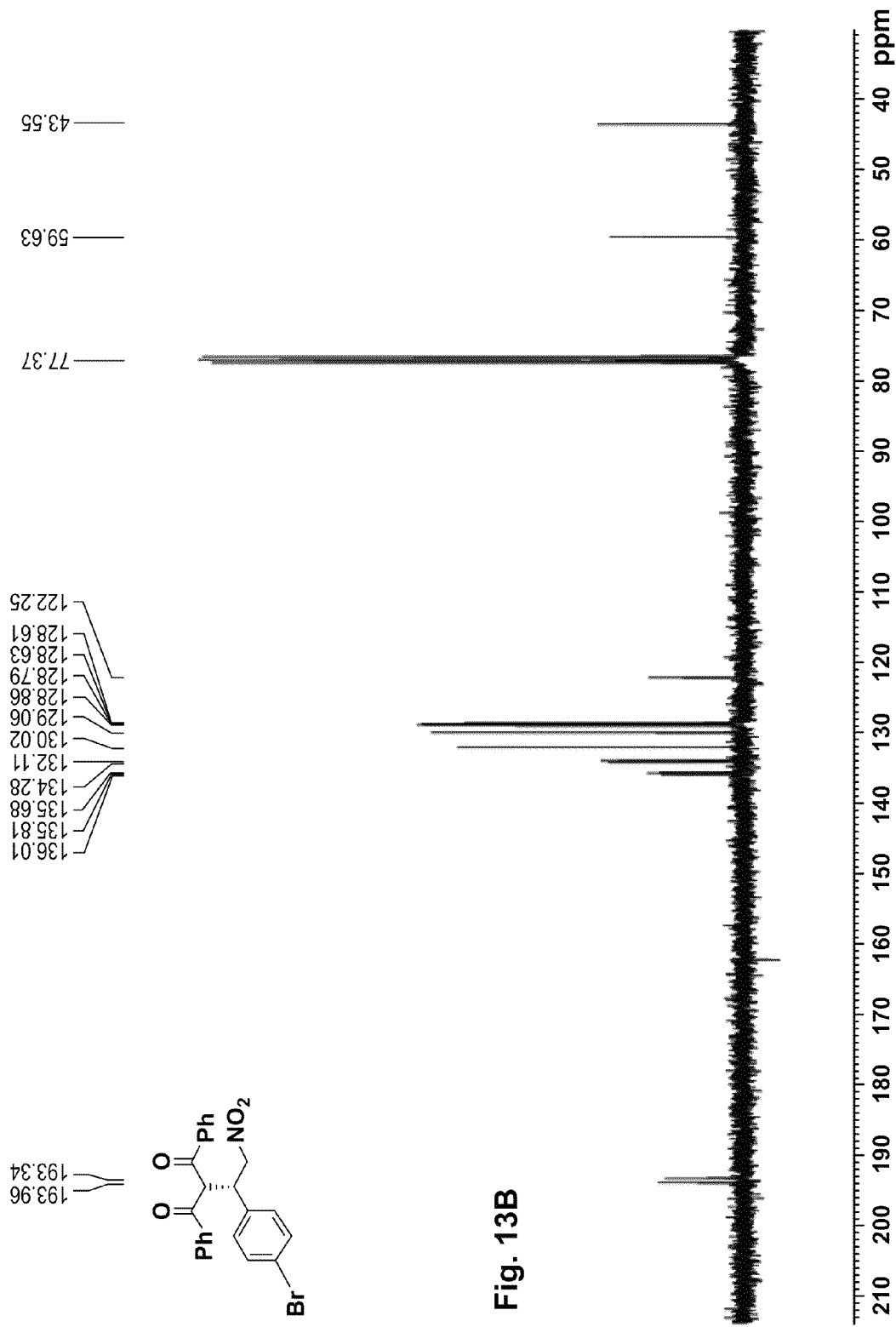
Figure 14A:
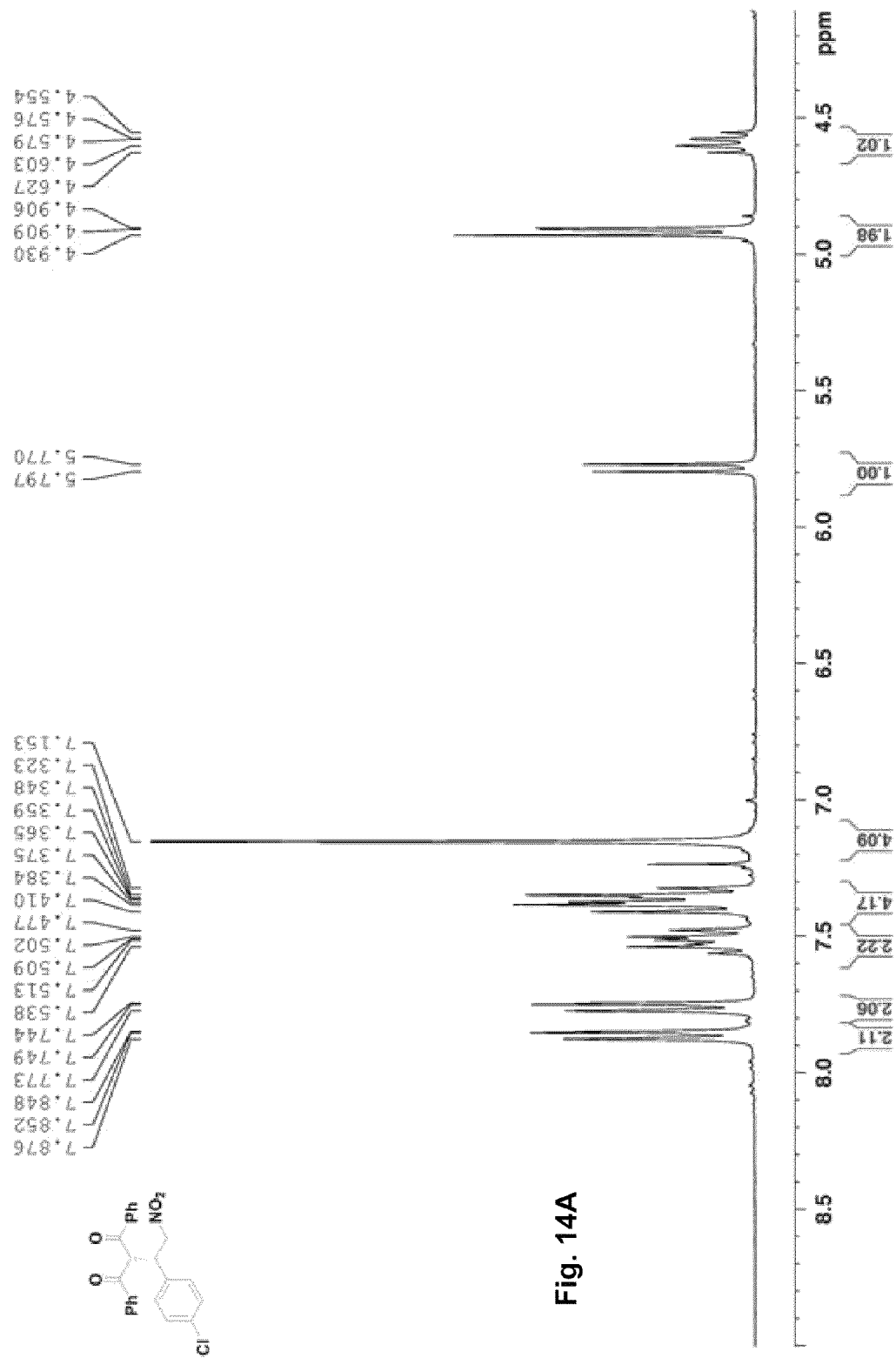
FIG. 14A depicts a $^1$H NMR spectrum and FIG. 14B a $^{13}$C NMR spectrum of compound 3g.
Figure 14B:
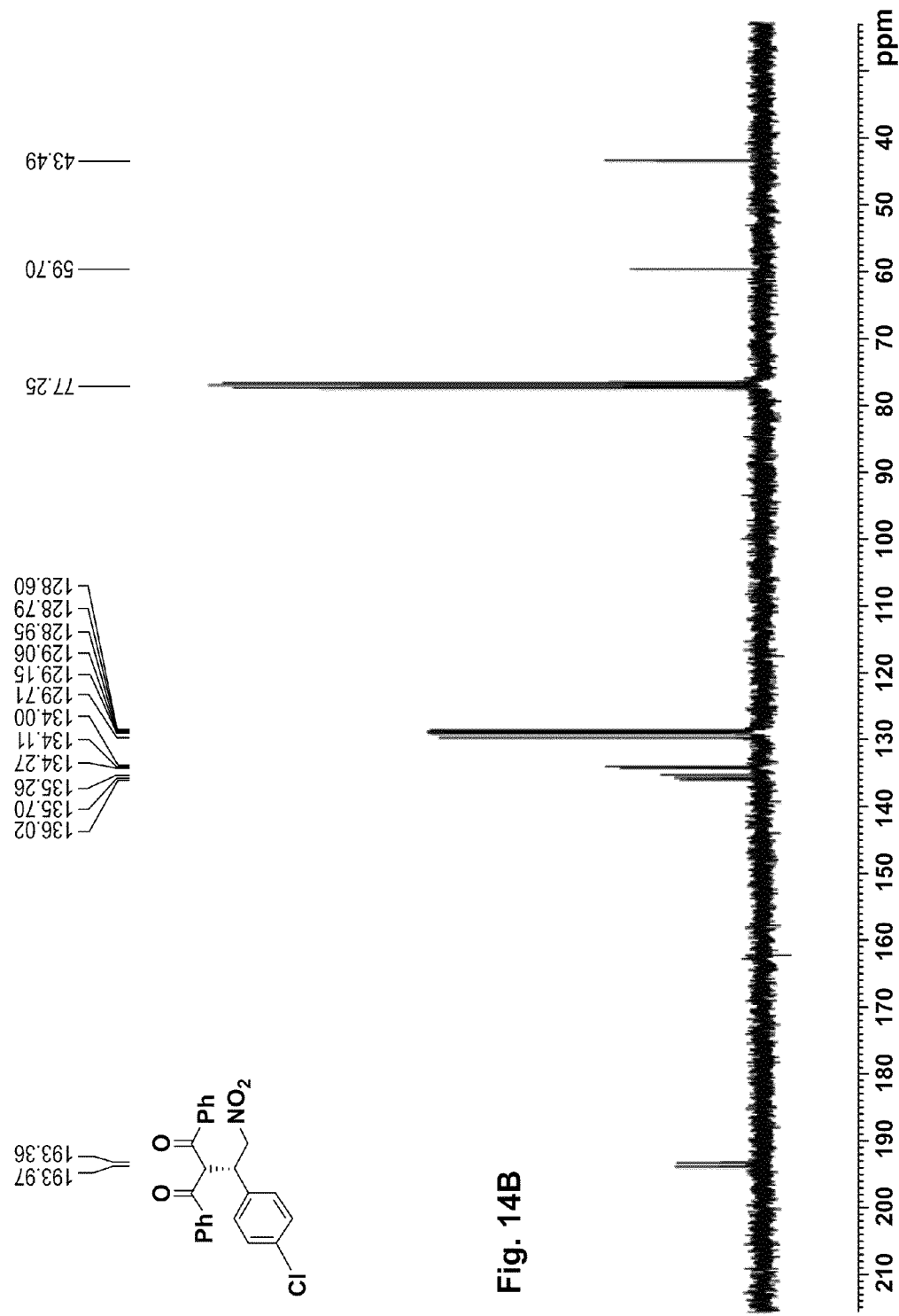
Figure 15A:
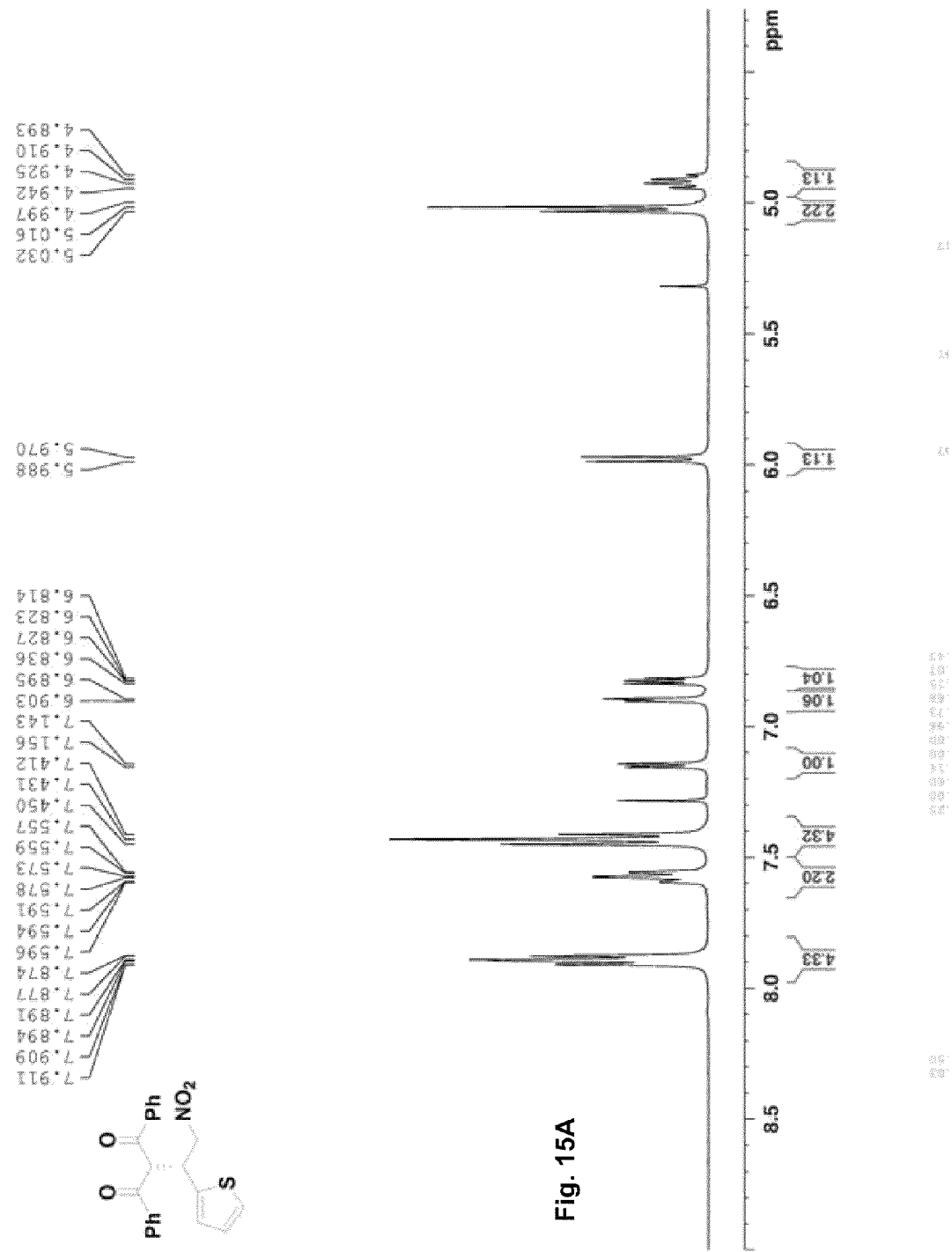
FIG. 15A depicts a $^1$H NMR spectrum and FIG. 15B a $^{13}$C NMR spectrum of compound 3h.
Figure 15B:
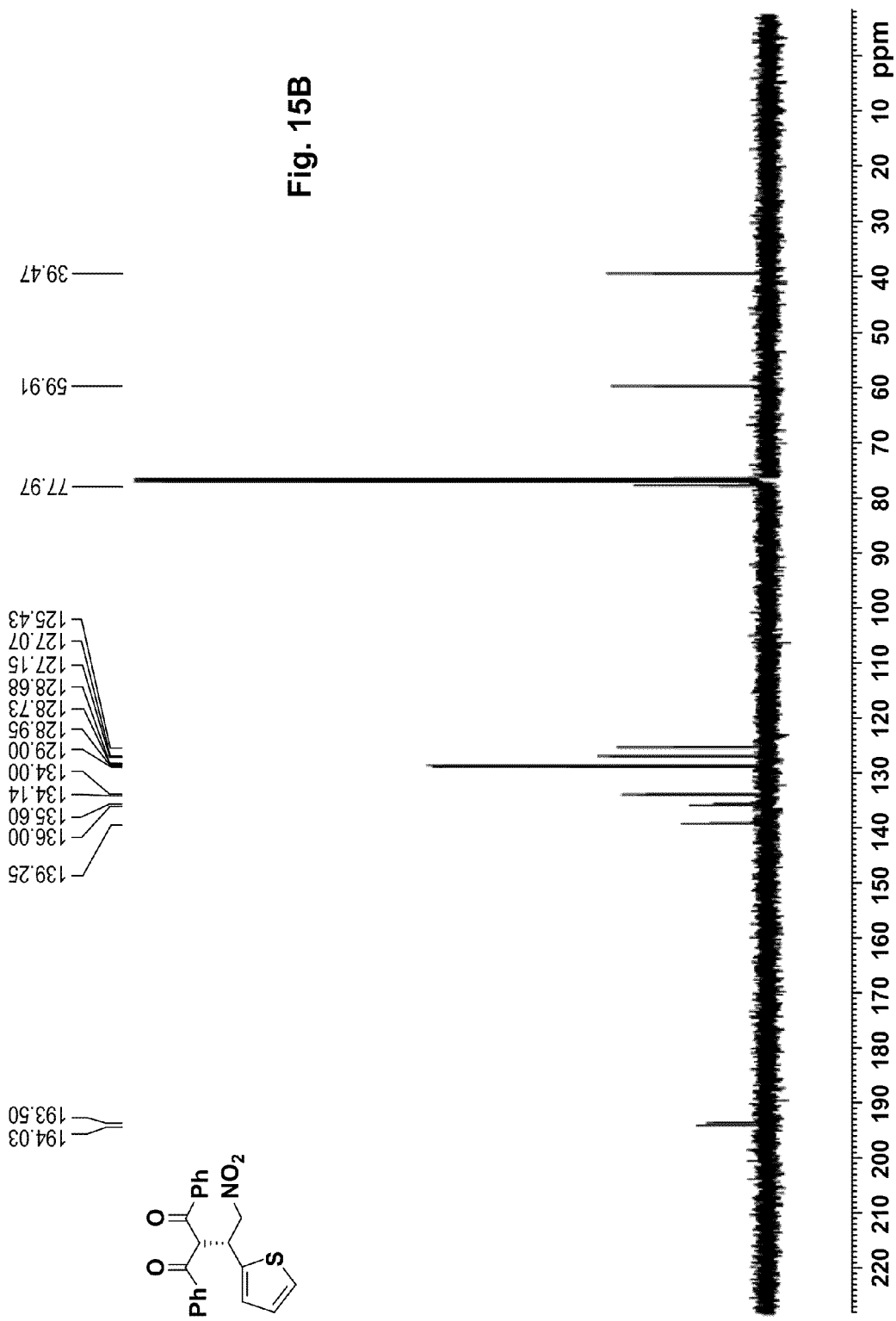
Figure 16A:
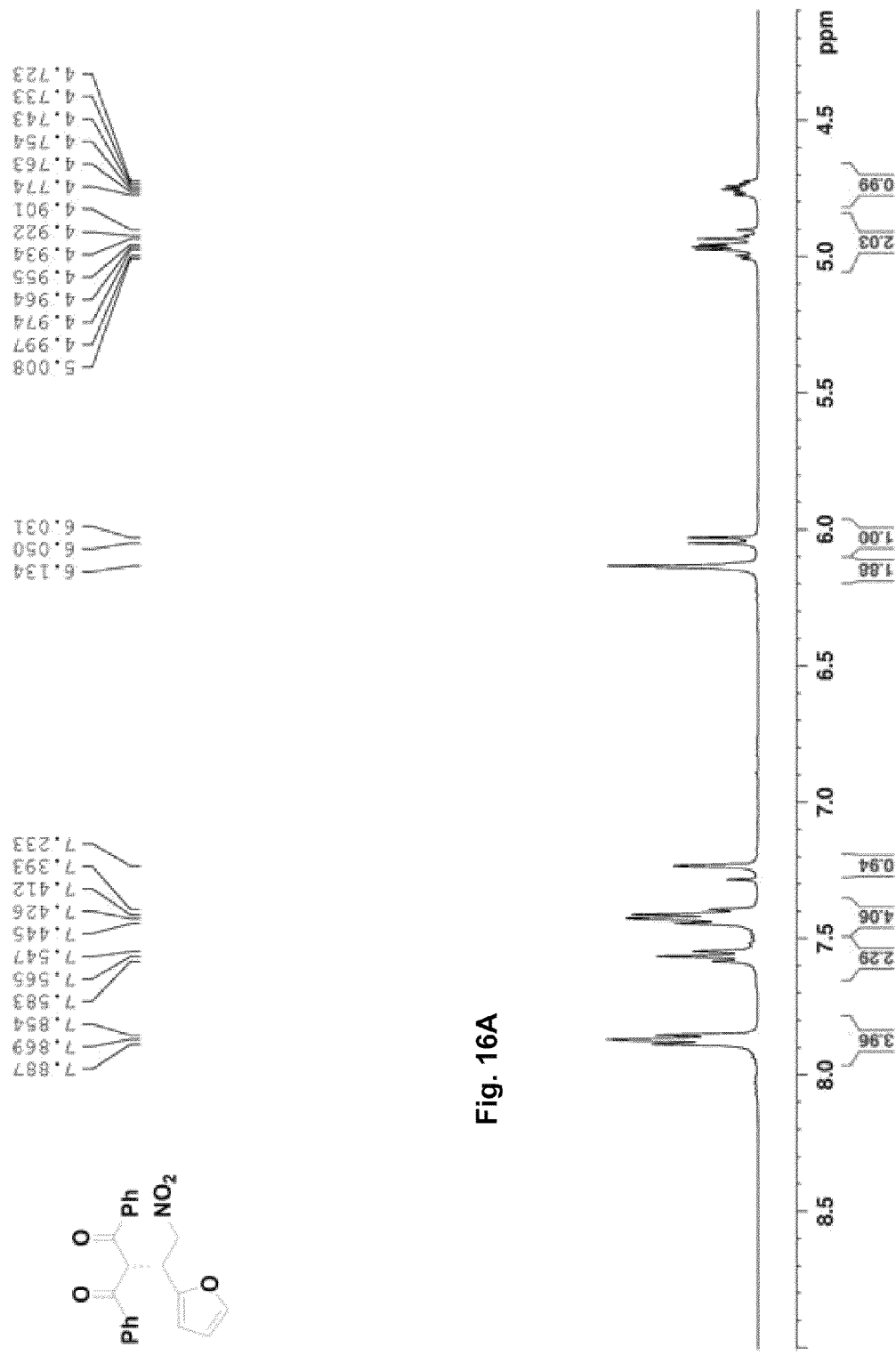
FIG. 16A depicts a $^1$H NMR spectrum and FIG. 16B a $^{13}$C NMR spectrum of compound 3i.
Figure 16B:
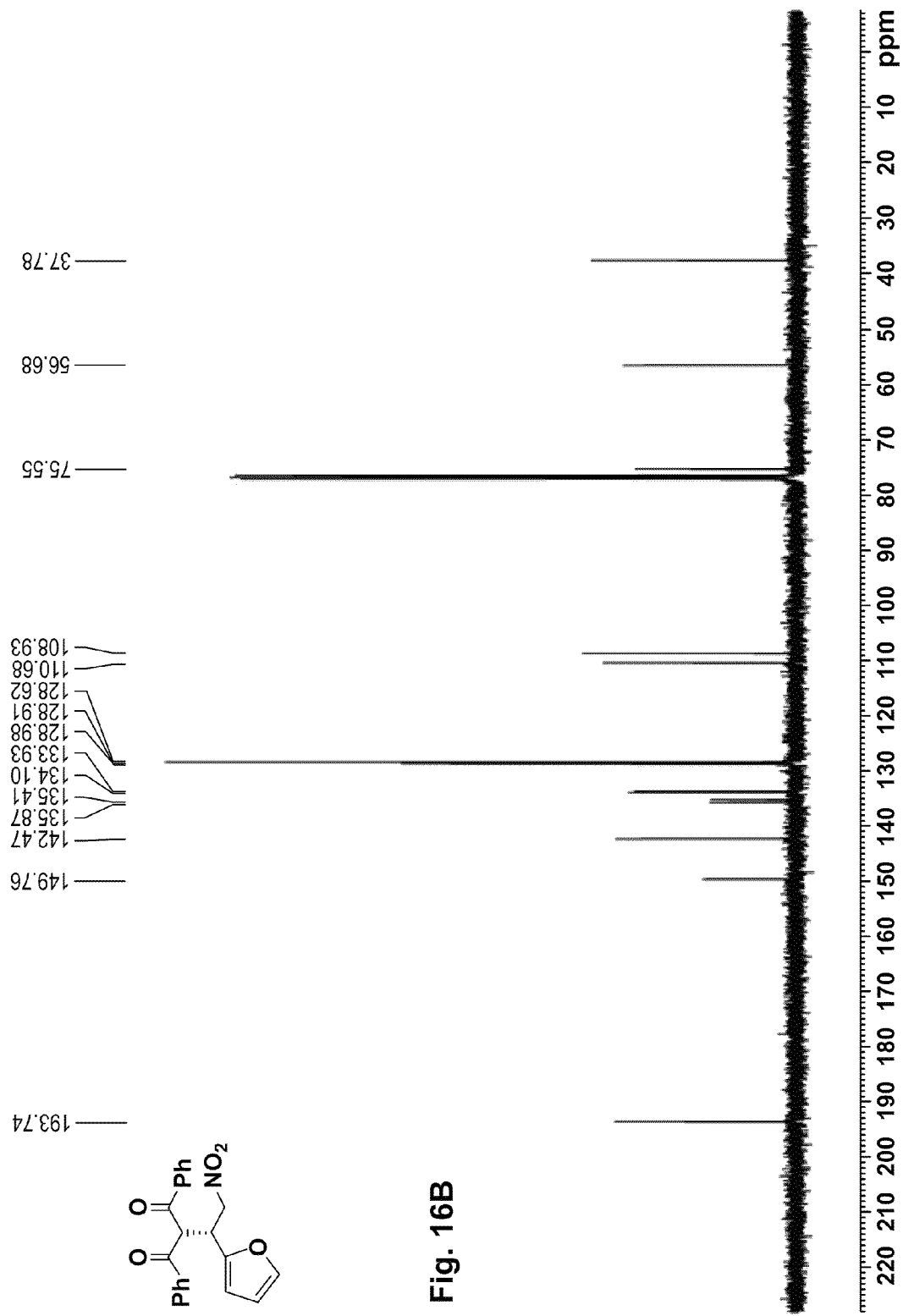
Figure 17A:
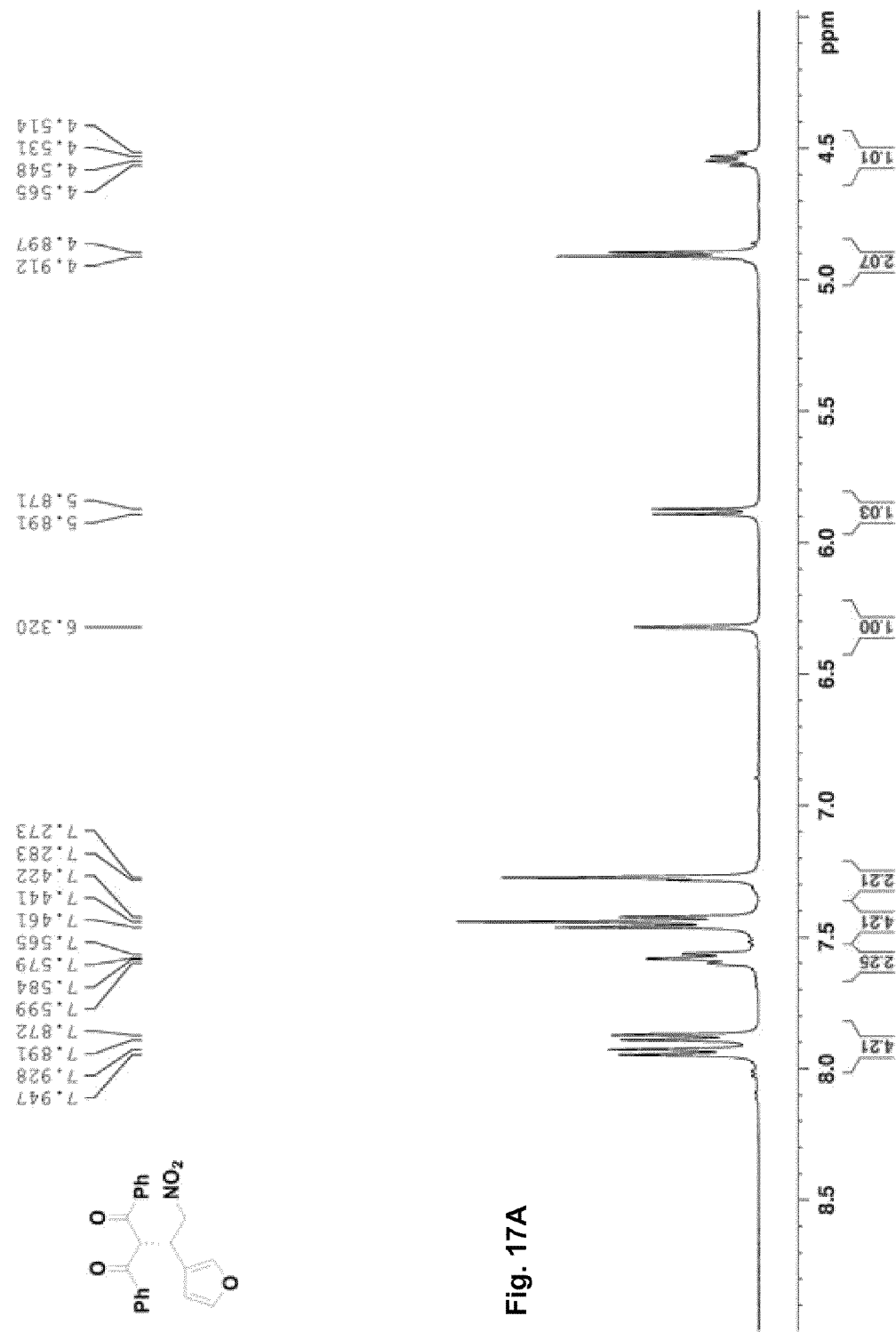
FIG. 17A depicts a $^1$H NMR spectrum and FIG. 17B a $^{13}$C NMR spectrum of compound 3j.
Figure 17B:
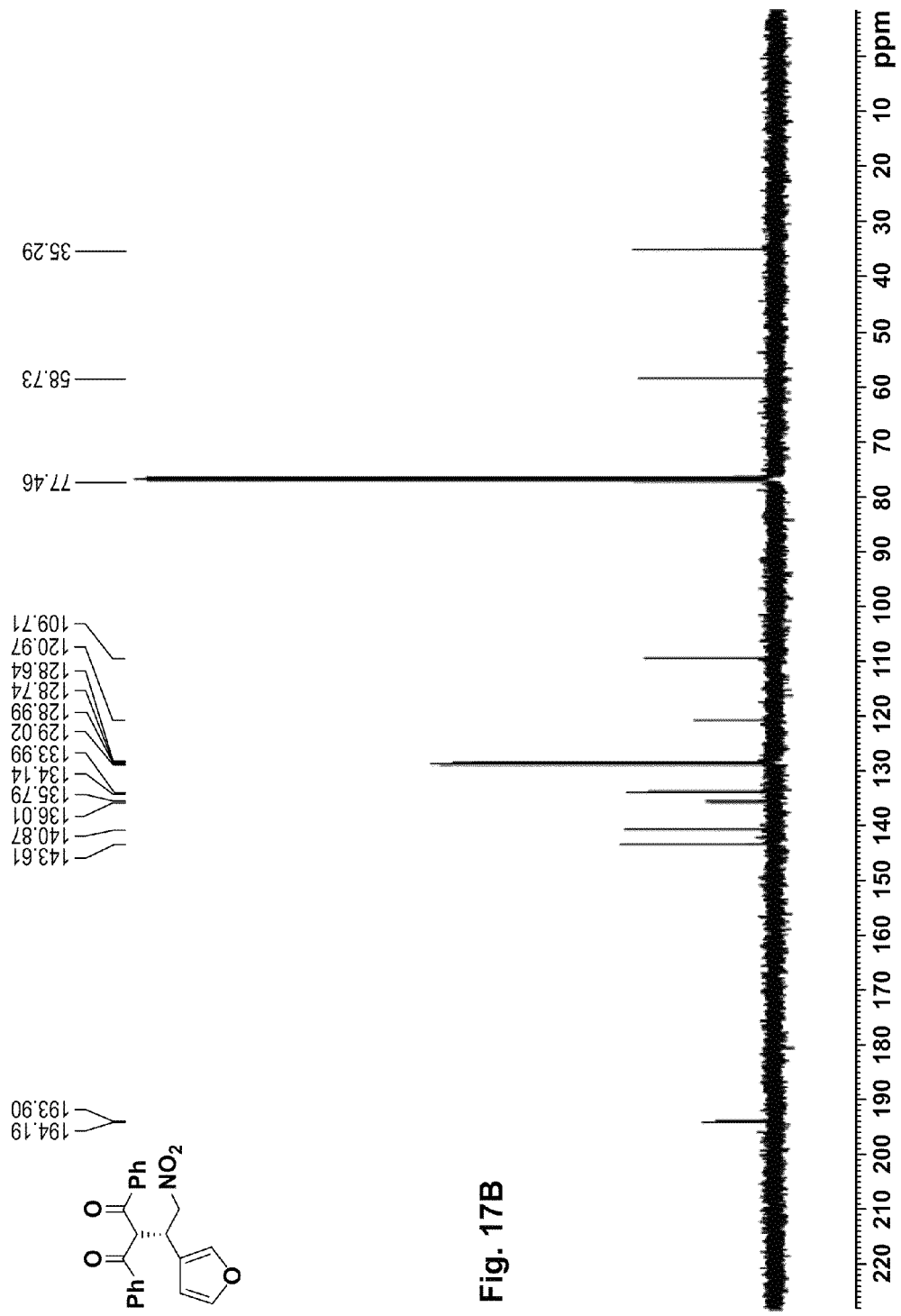
Figure 18A:
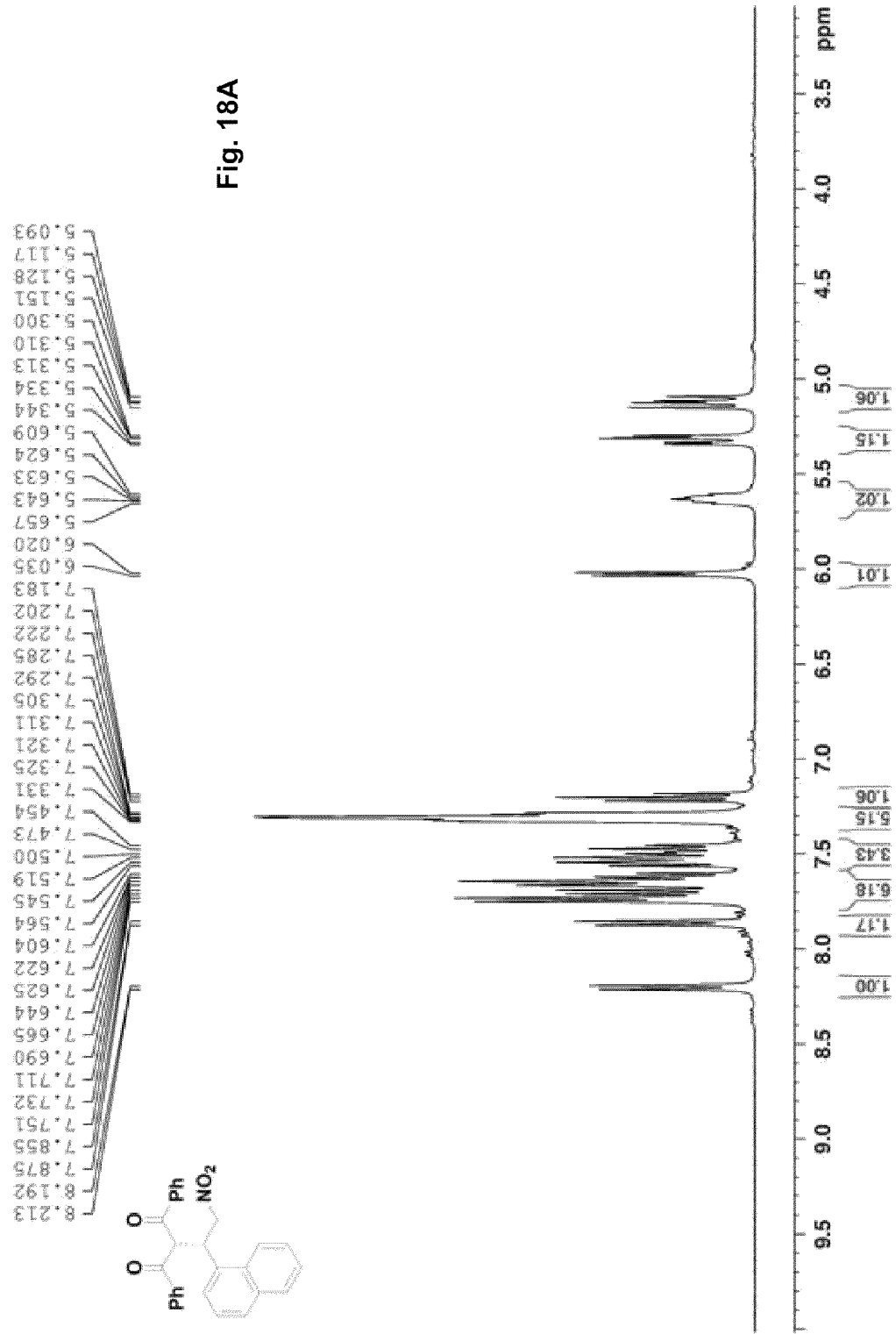
FIG. 18A depicts a $^1$H NMR spectrum and FIG. 18B a $^{13}$C NMR spectrum of compound 3k.
Figure 18B:
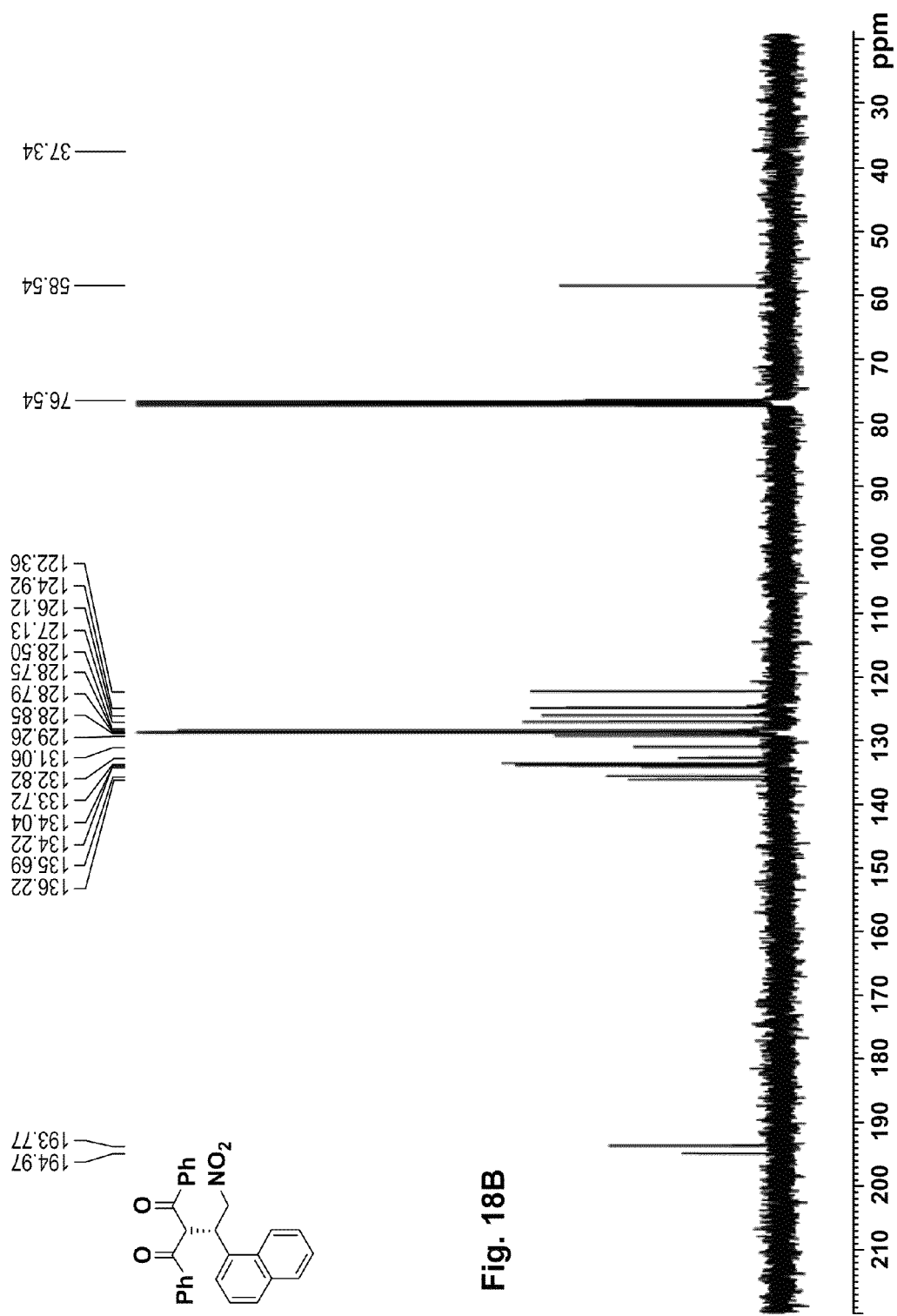
Figure 19A:
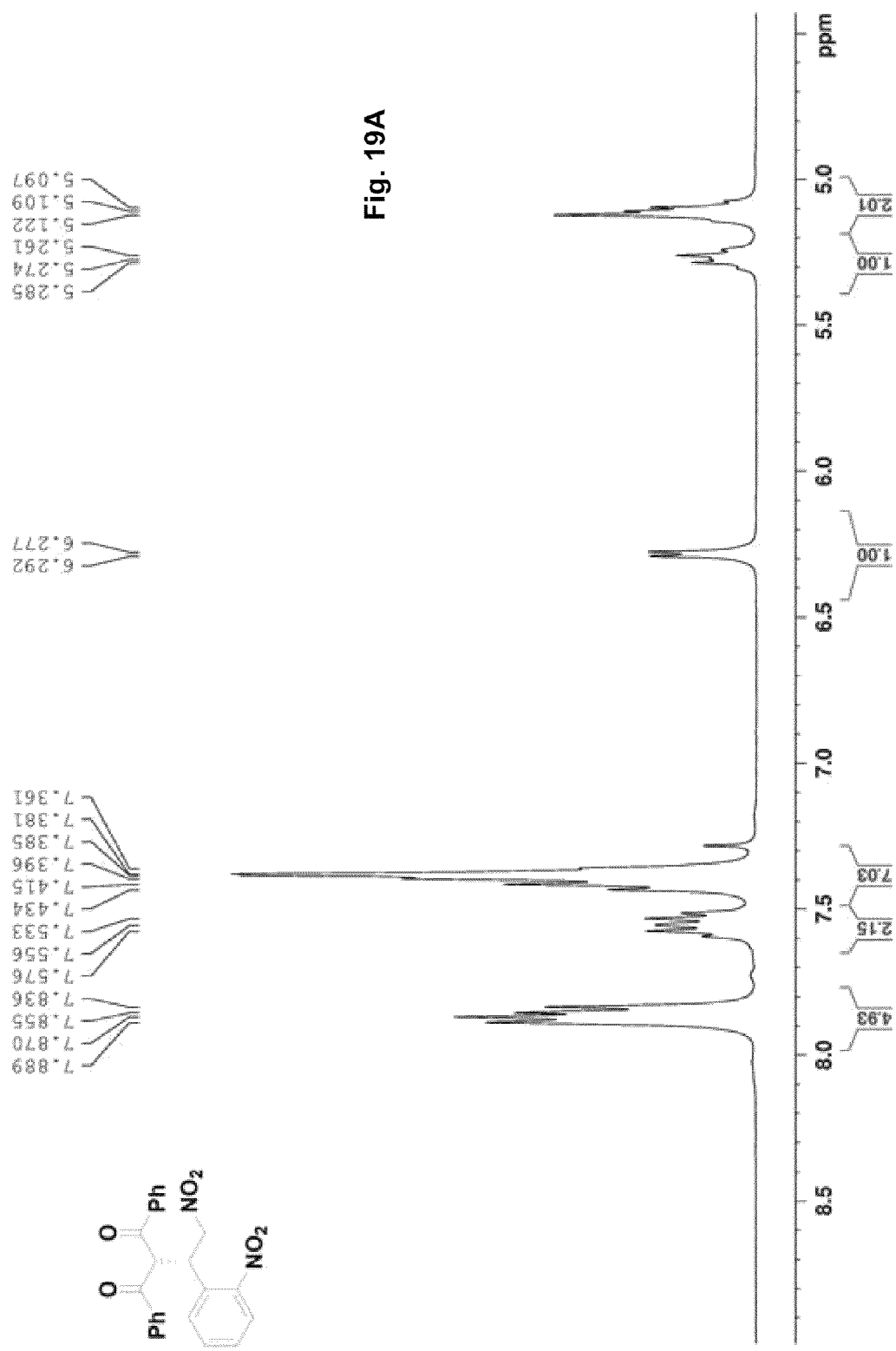
FIG. 19A depicts a $^1$H NMR spectrum and FIG. 19B a $^{13}$C NMR spectrum of compound 3l.
Figure 19B:
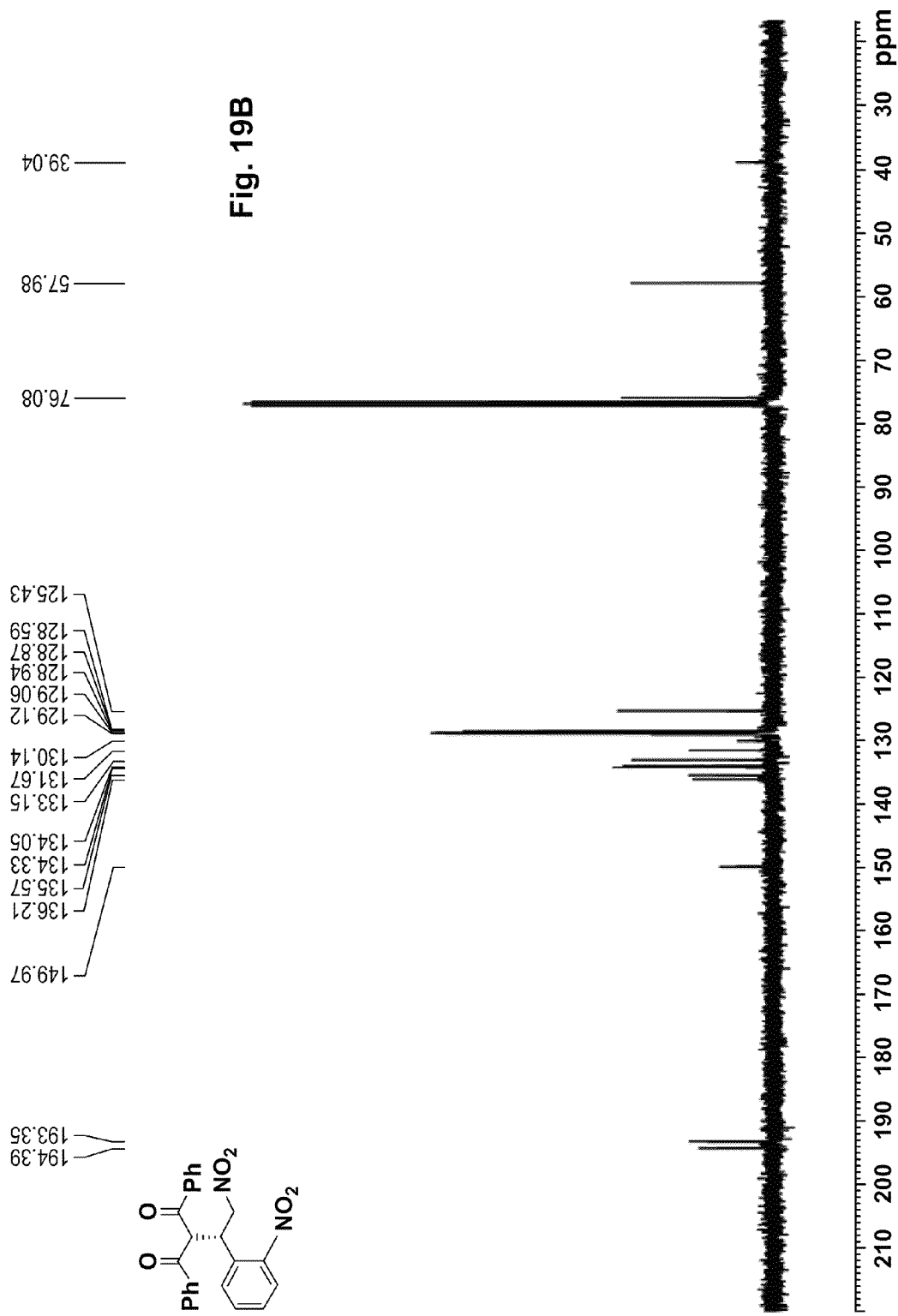
Figure 20A:
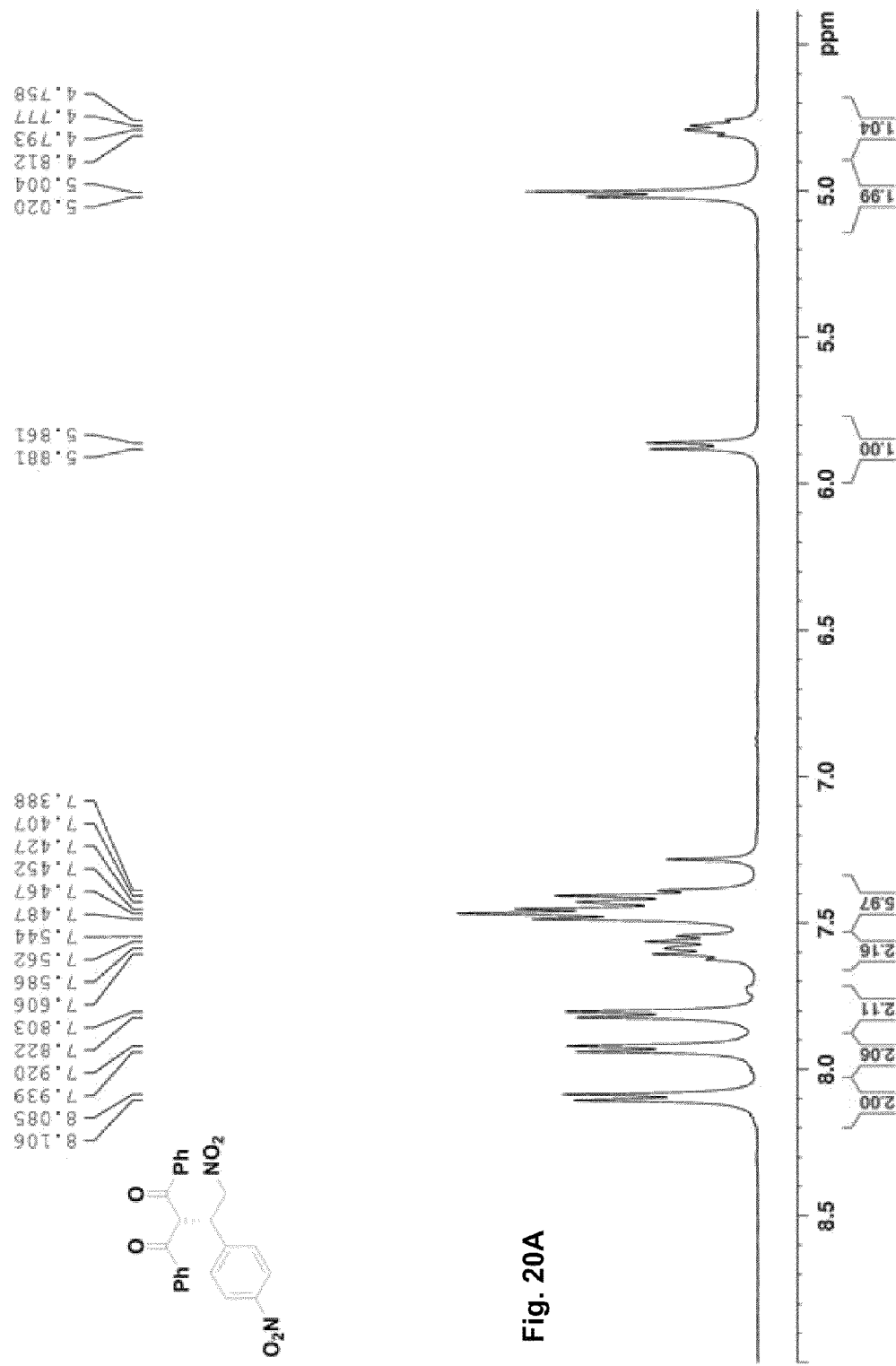
FIG. 20A depicts a $^1$H NMR spectrum and FIG. 20B a $^{13}$C NMR spectrum of compound 3m.
Figure 23A:
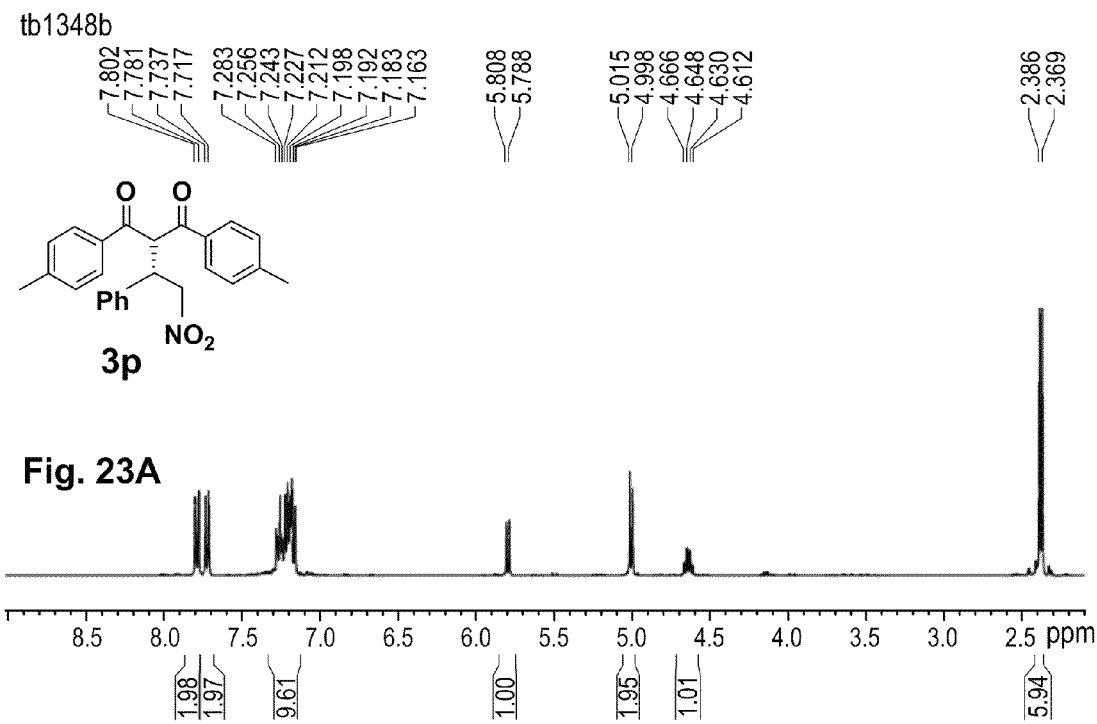
FIG. 23A depicts a $^1$H NMR spectrum and FIG. 23B a $^{13}$C NMR spectrum of compound 3p.
Figure 23B:
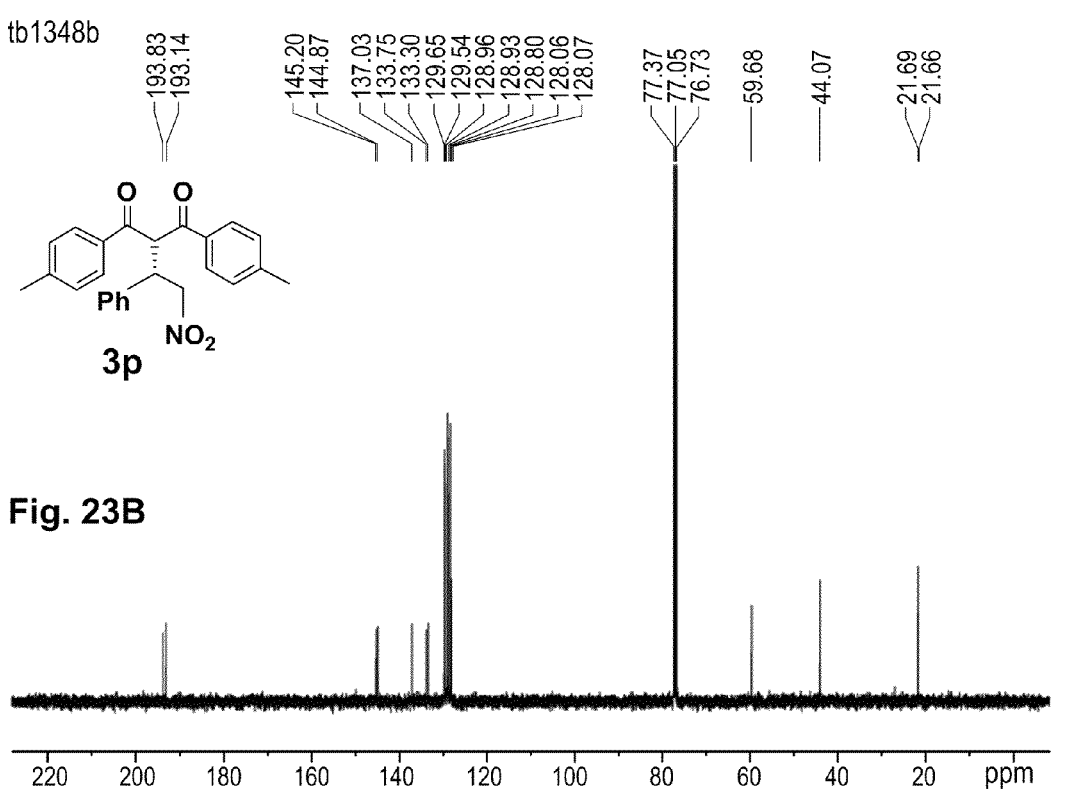
Figure 24A:
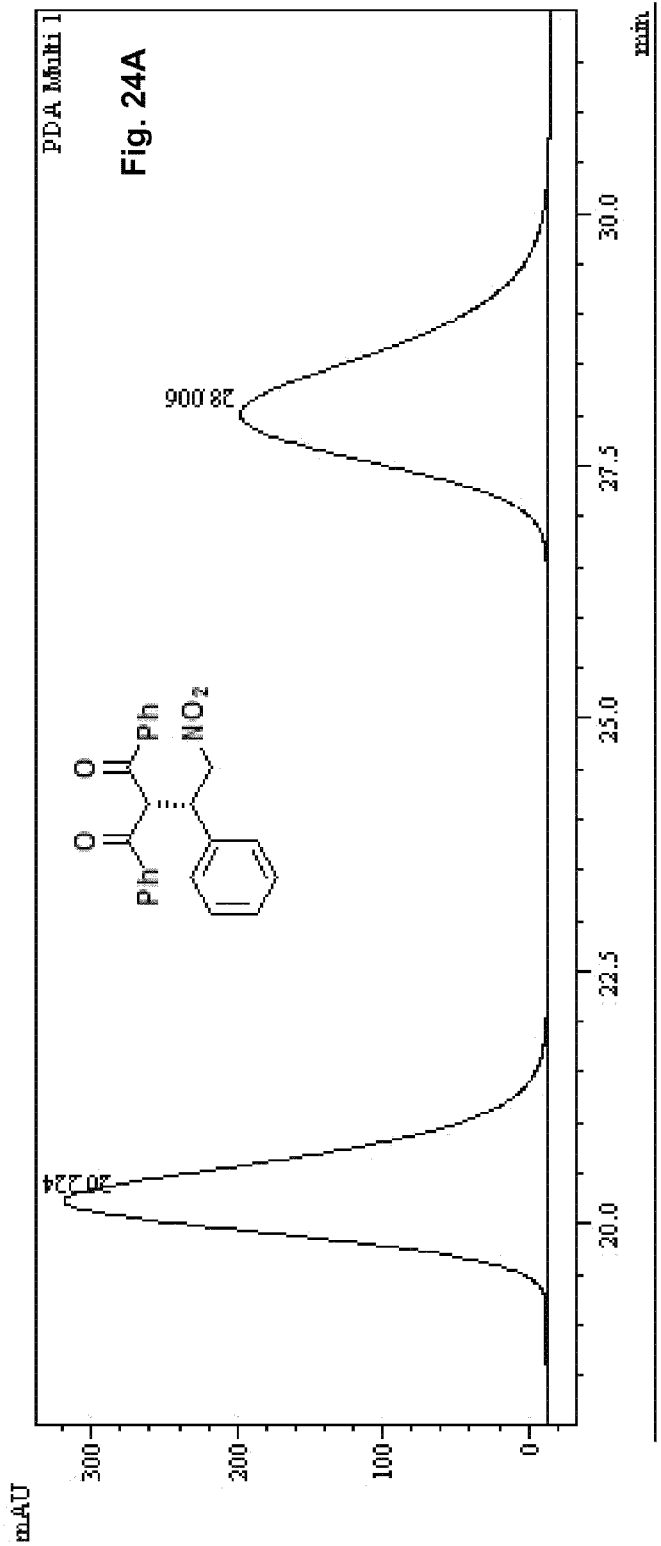
FIG. 24 depicts an HPLC spectrum of a racemic mixture of compound 3a (A) in comparison the obtained product 3a (B).
Figure 24B:
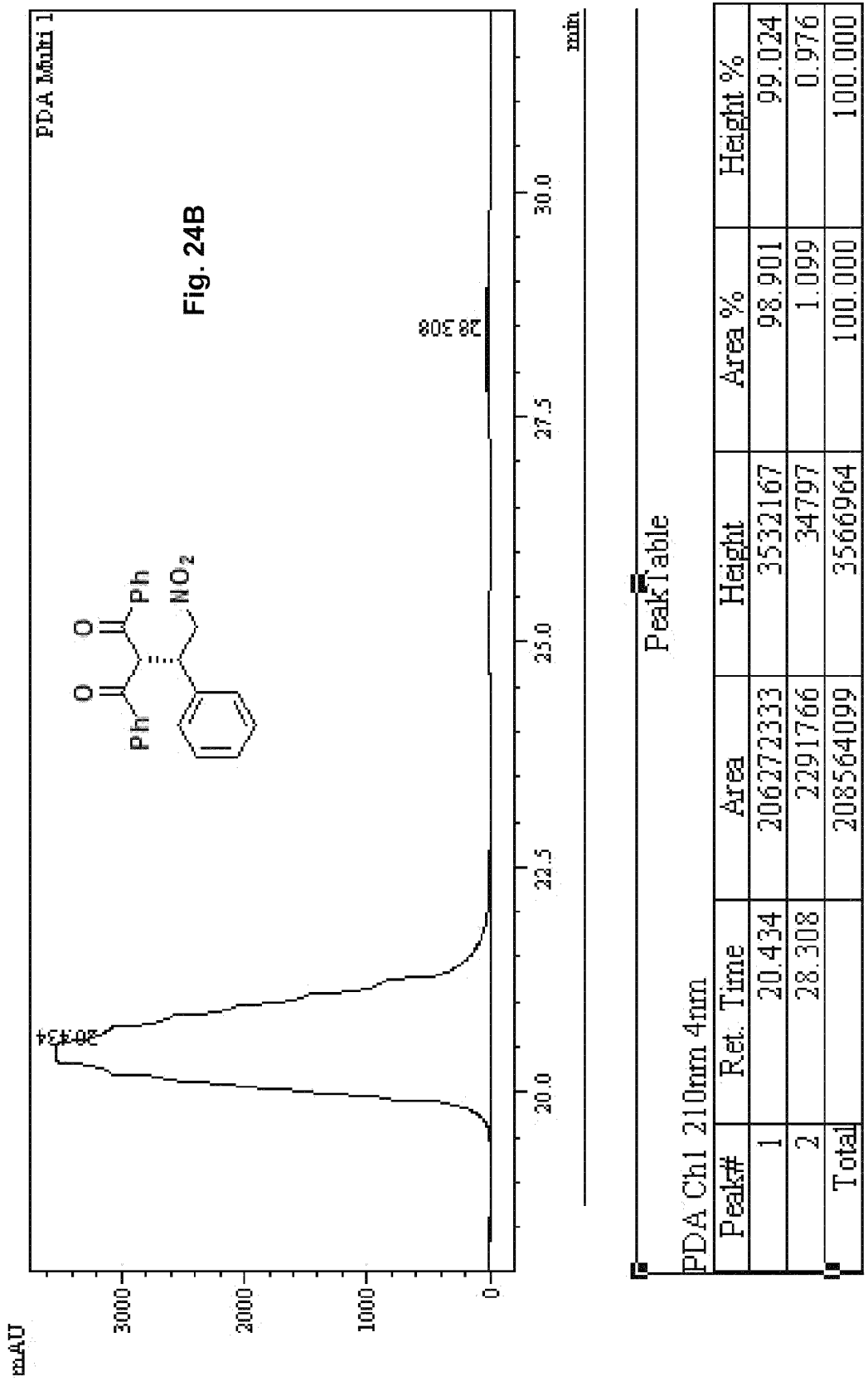
Figure 25A:
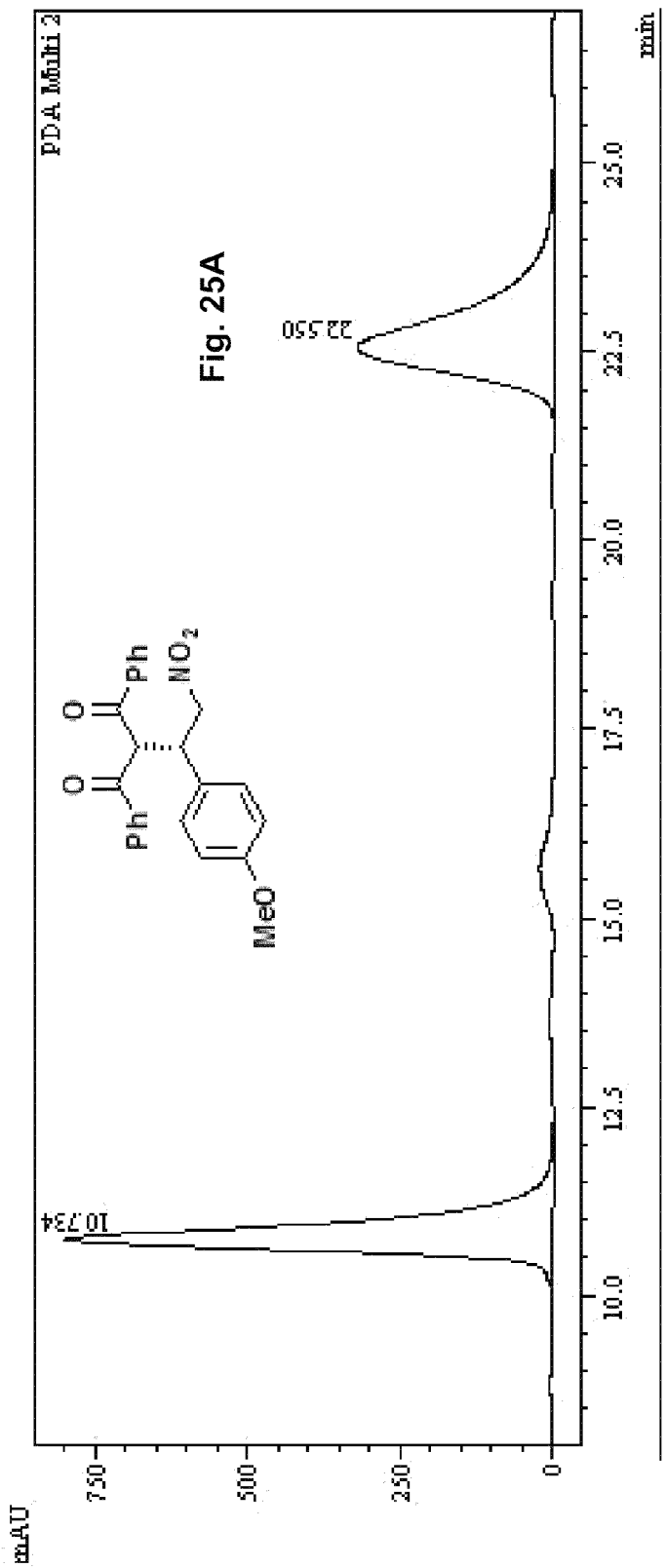
FIG. 25 depicts an HPLC spectrum of a racemic mixture of compound 3b (A) in comparison the obtained product 3b (B).
Figure 26A:
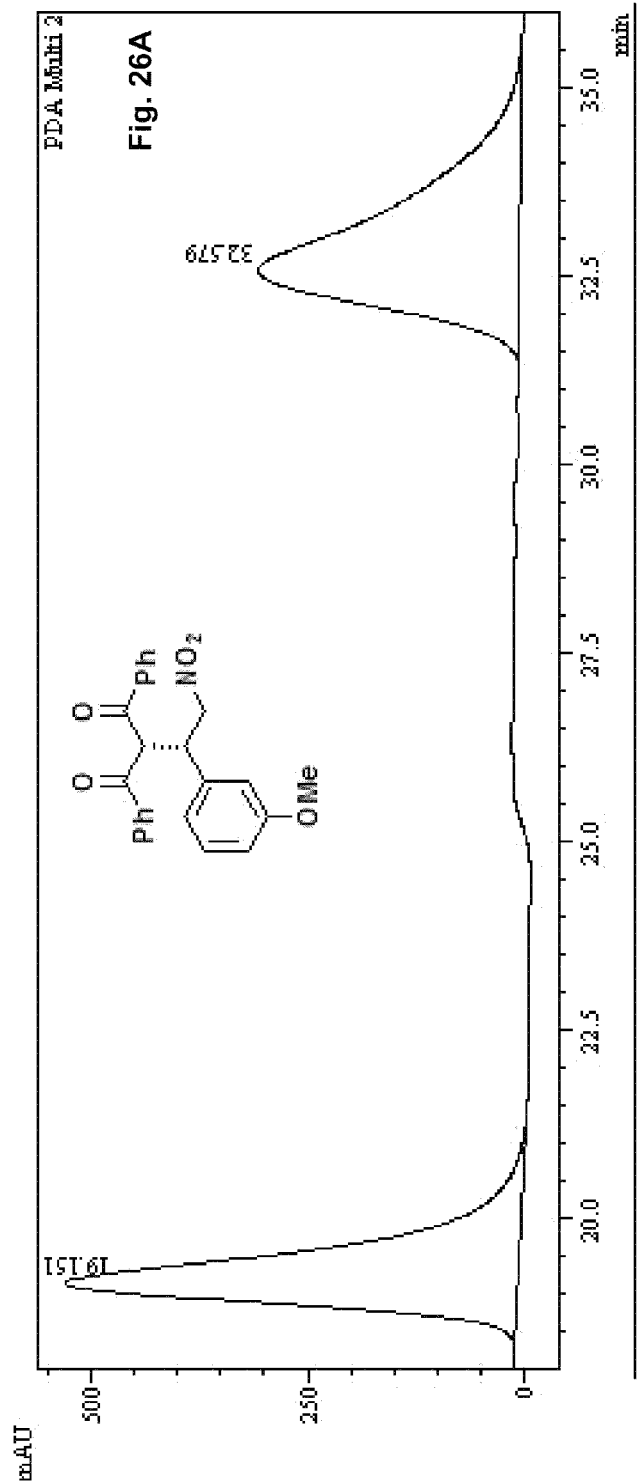
FIG. 26 depicts an HPLC spectrum of a racemic mixture of compound 3c (A) in comparison the obtained product 3c (B).
Figure 26B:
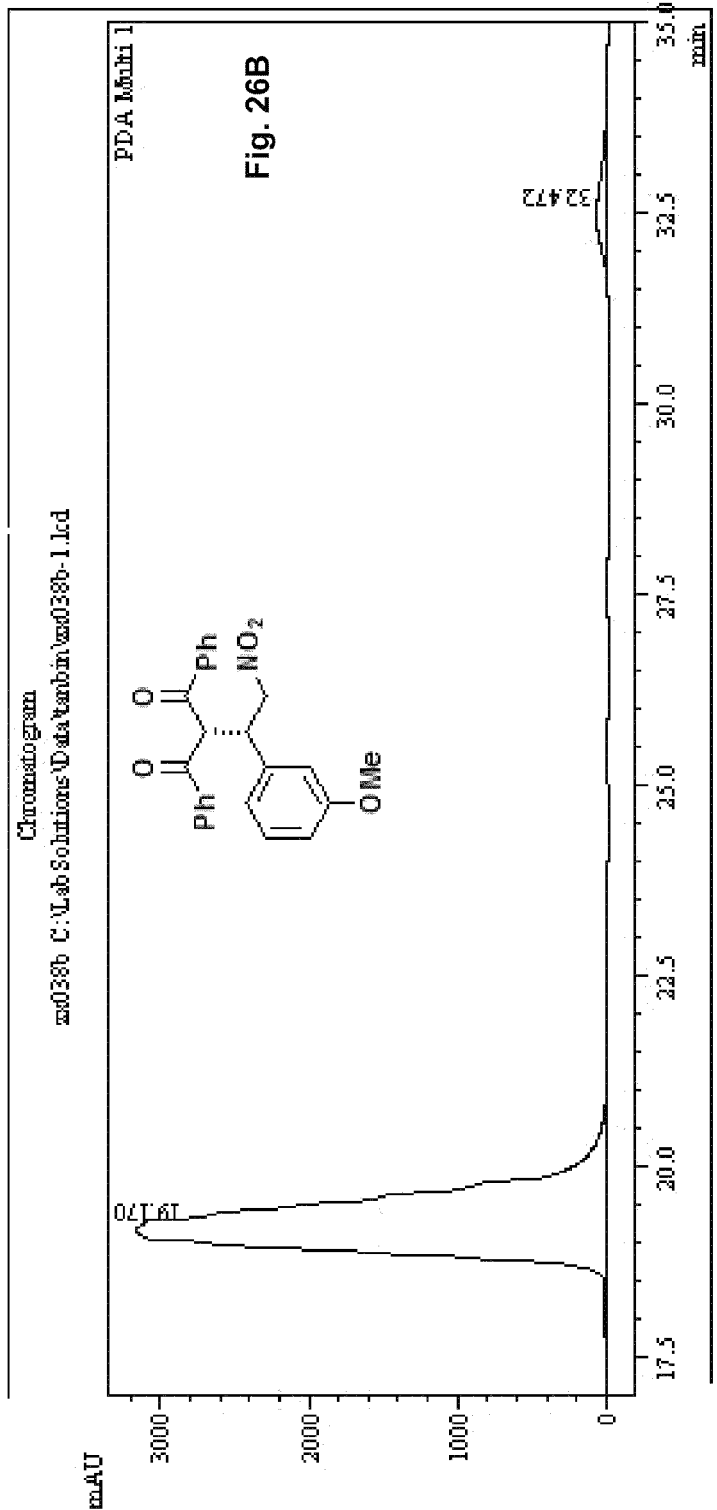
Figure 27A:
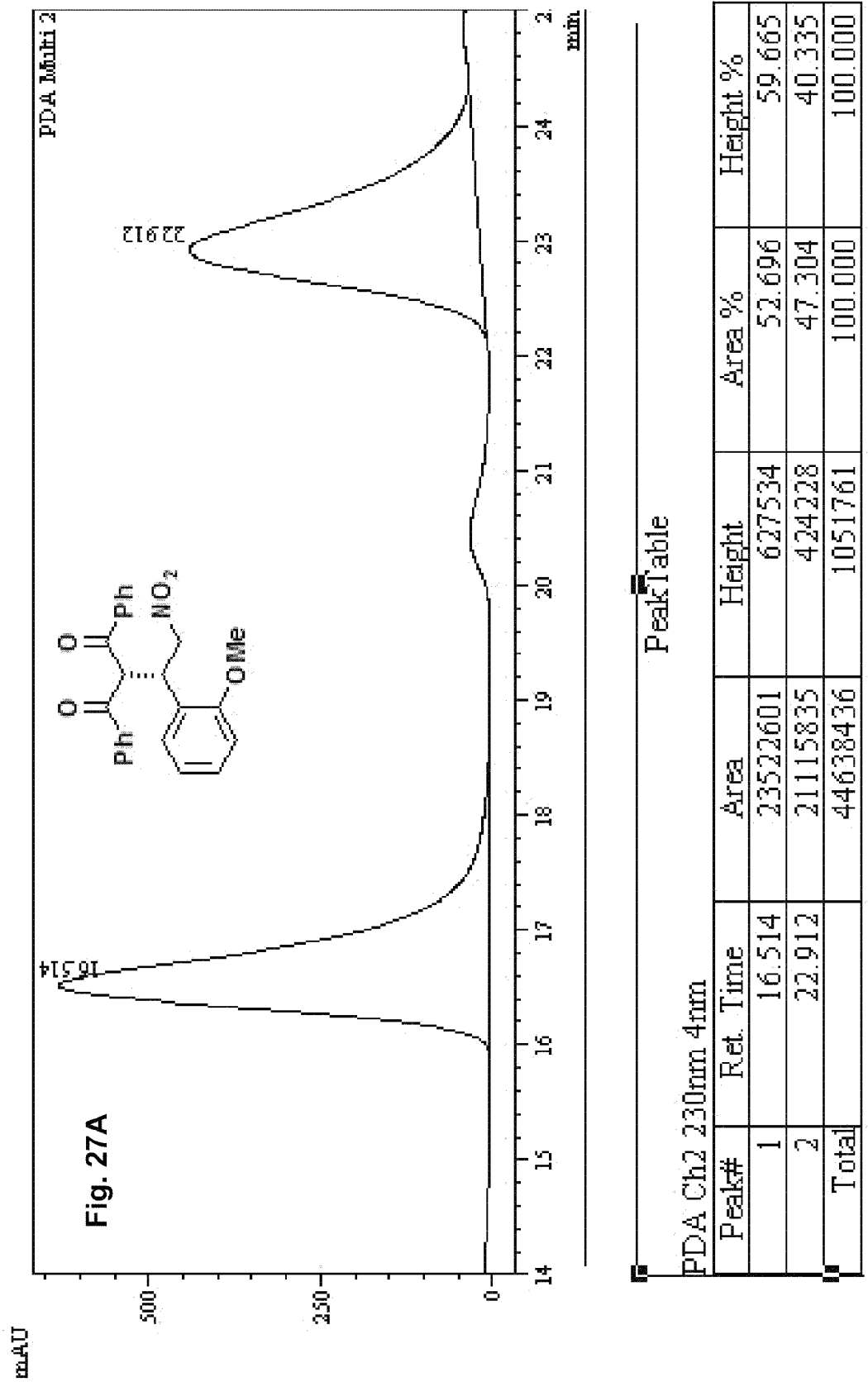
FIG. 27 depicts an HPLC spectrum of a racemic mixture of compound 3d (A) in comparison the obtained product 3d (B).
Figure 27B:
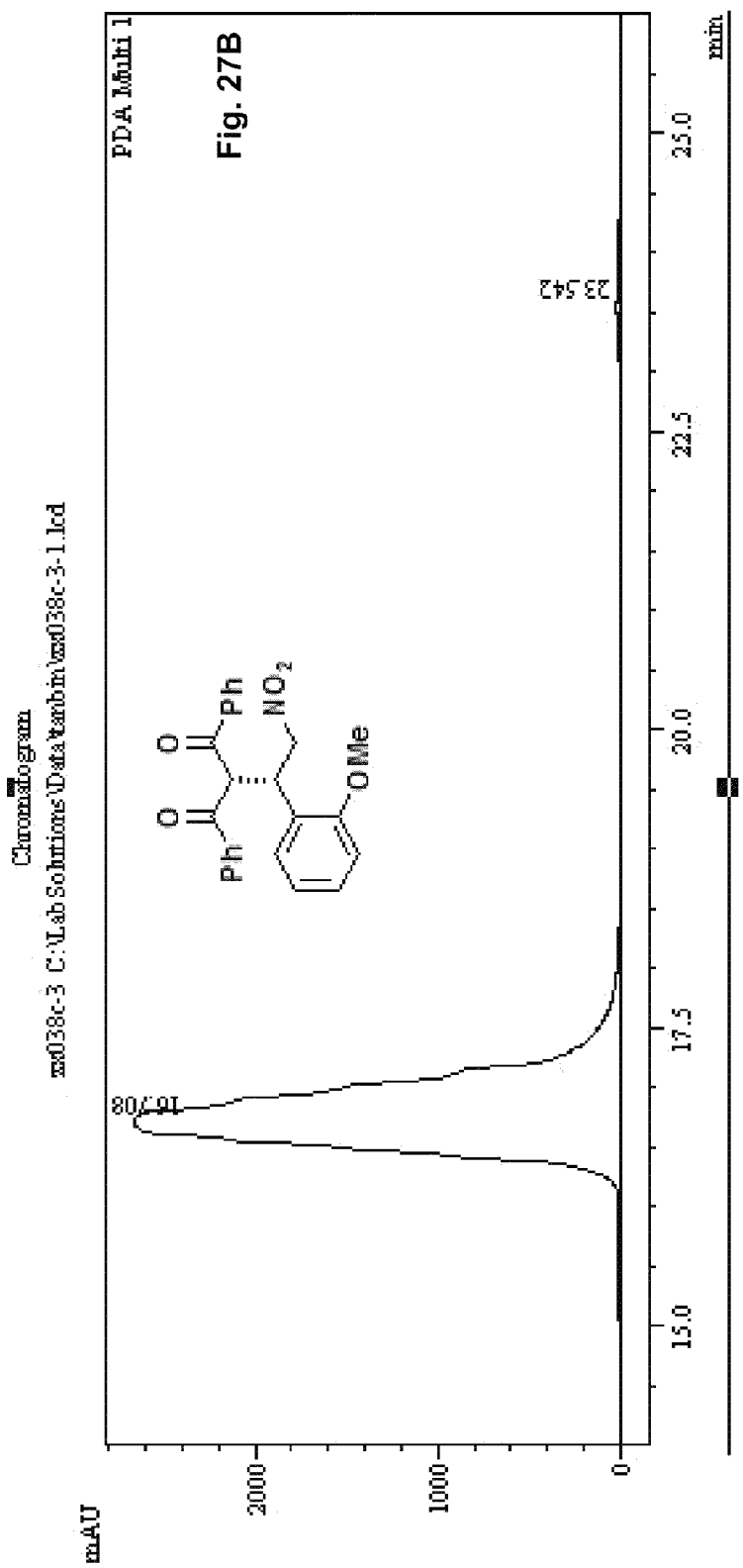
Figure 28A:
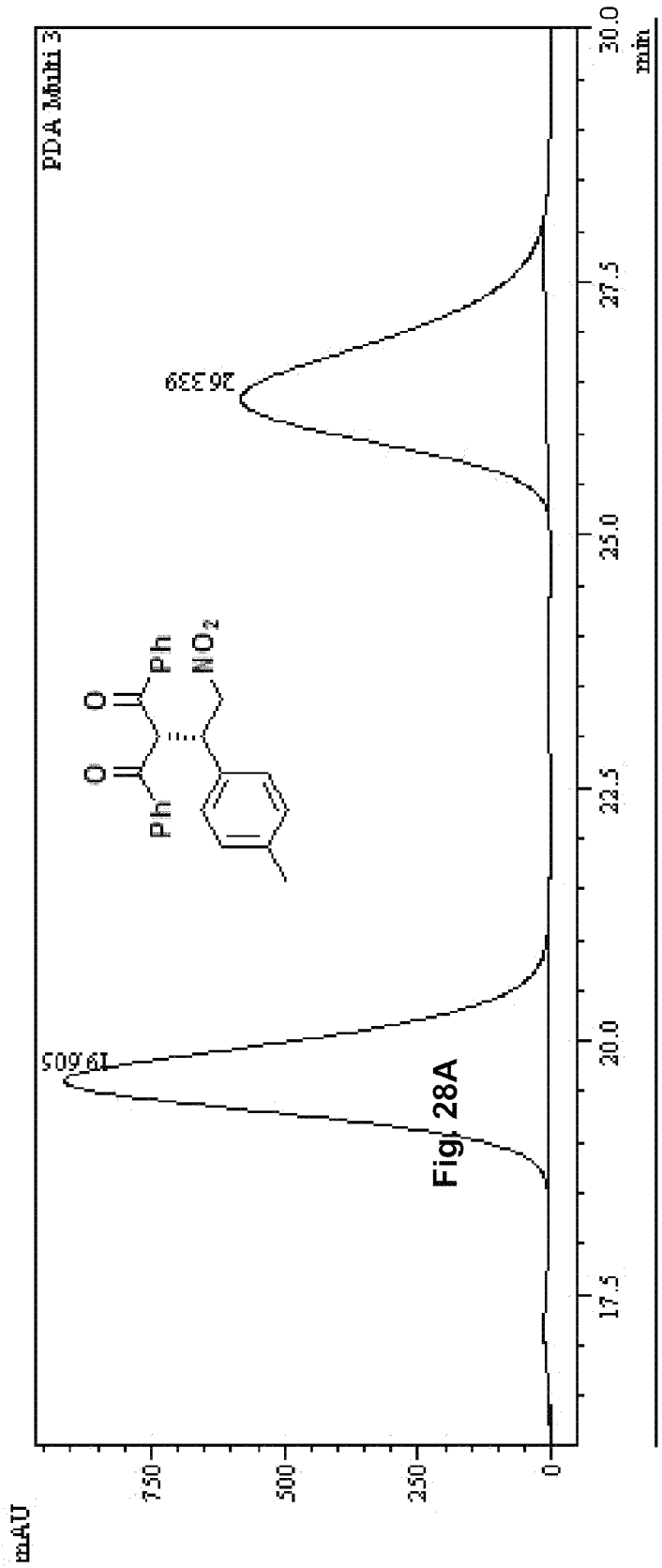
FIG. 28 depicts an HPLC spectrum of a racemic mixture of compound 3e (A) in comparison the obtained product 3e (B).
Figure 28B:
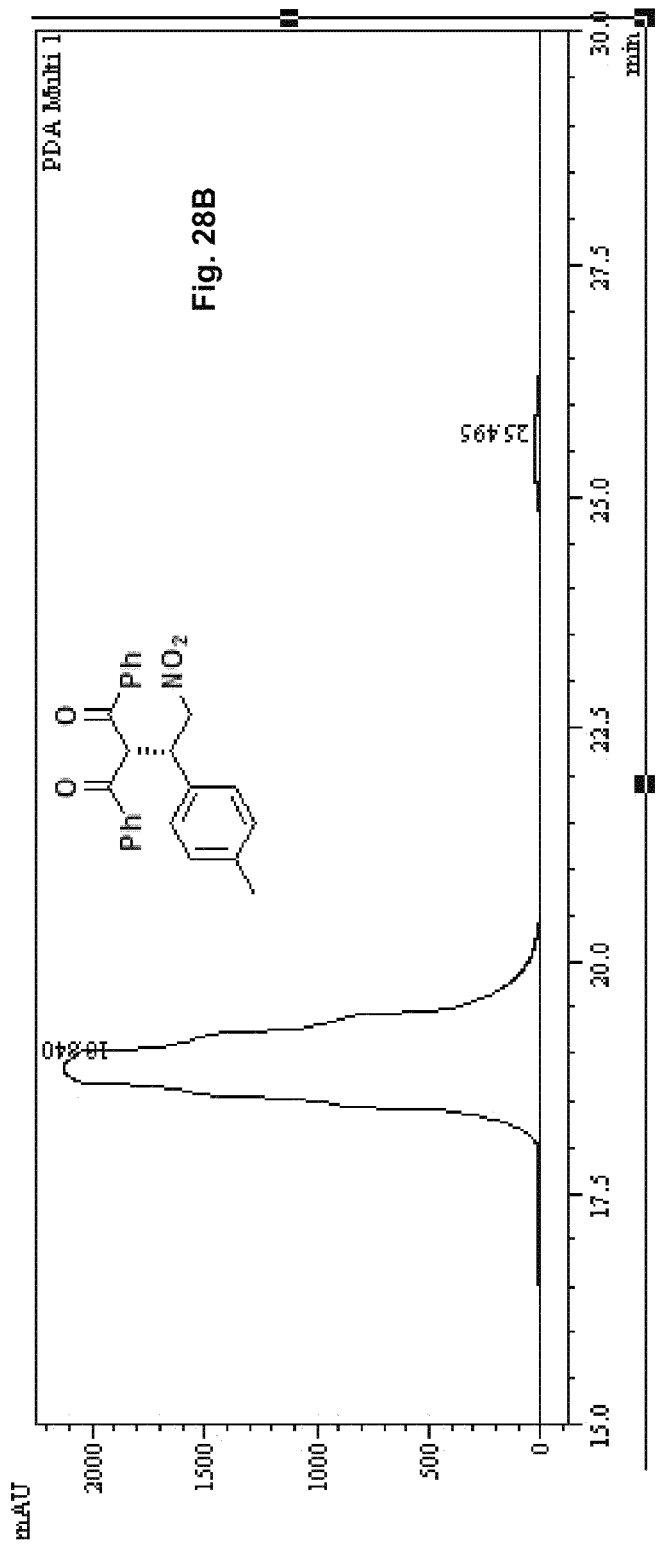
Figure 29A:
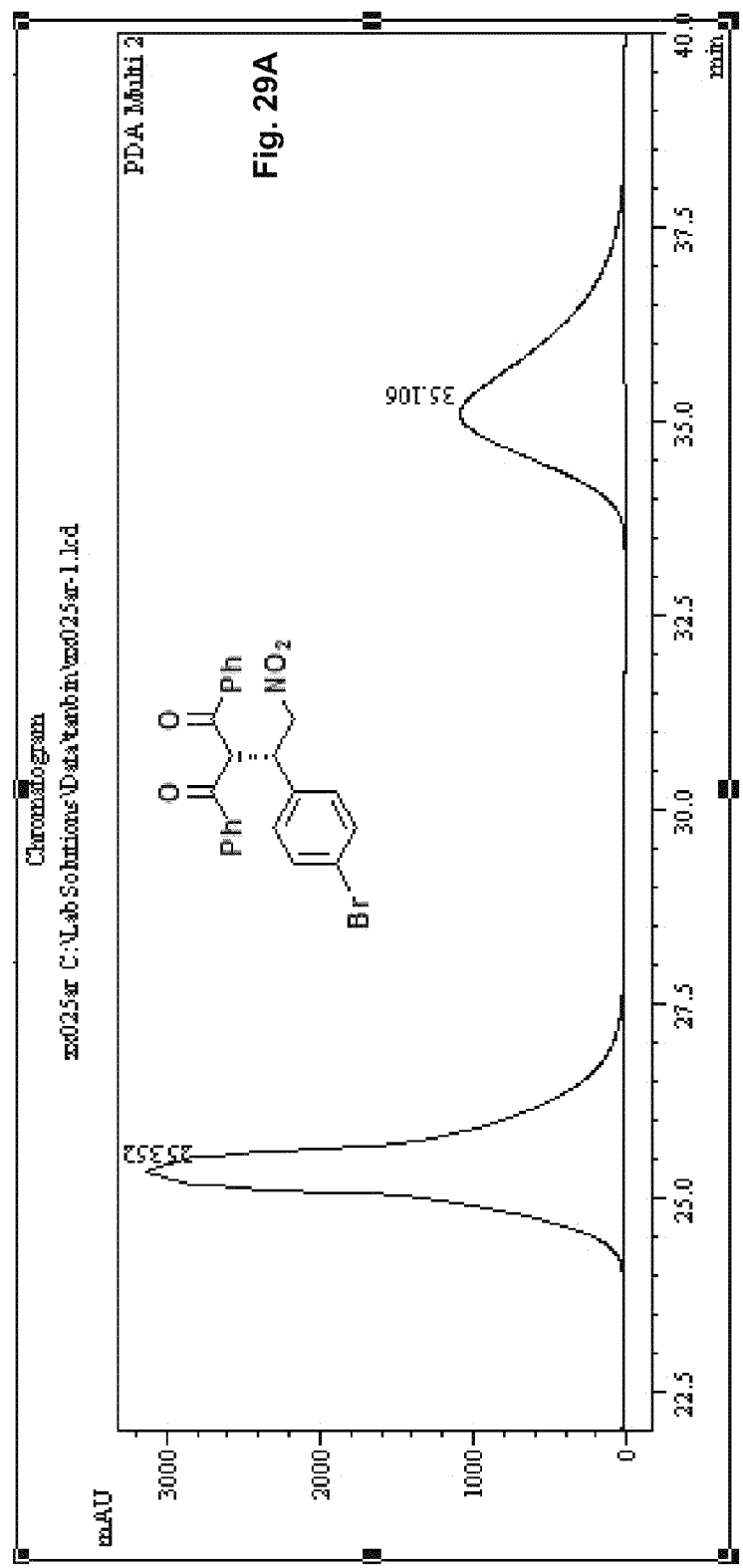
FIG. 29 depicts an HPLC spectrum of a racemic mixture of compound 3f (A) in comparison the obtained product 3f (B).
Figure 29B:
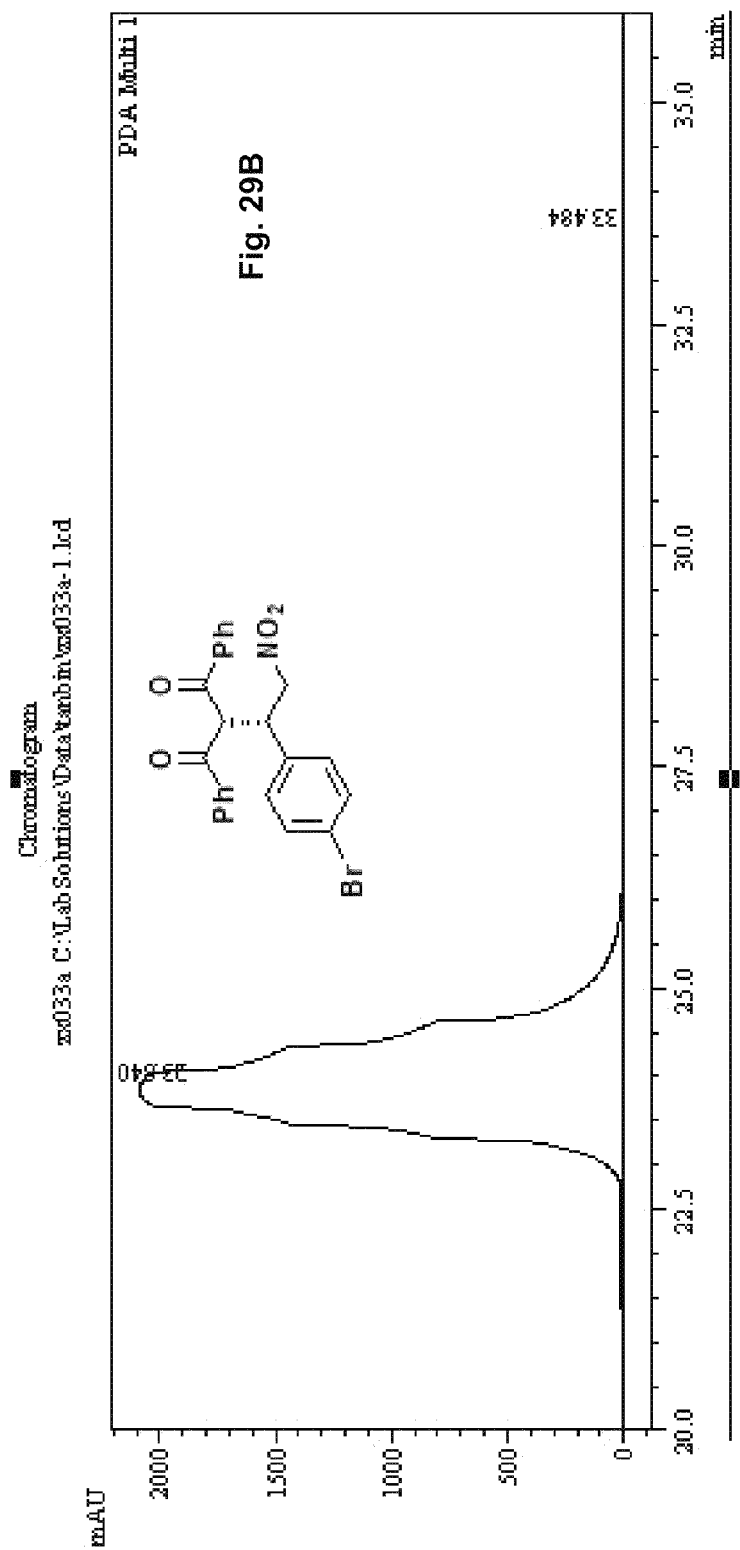
Figure 30A:
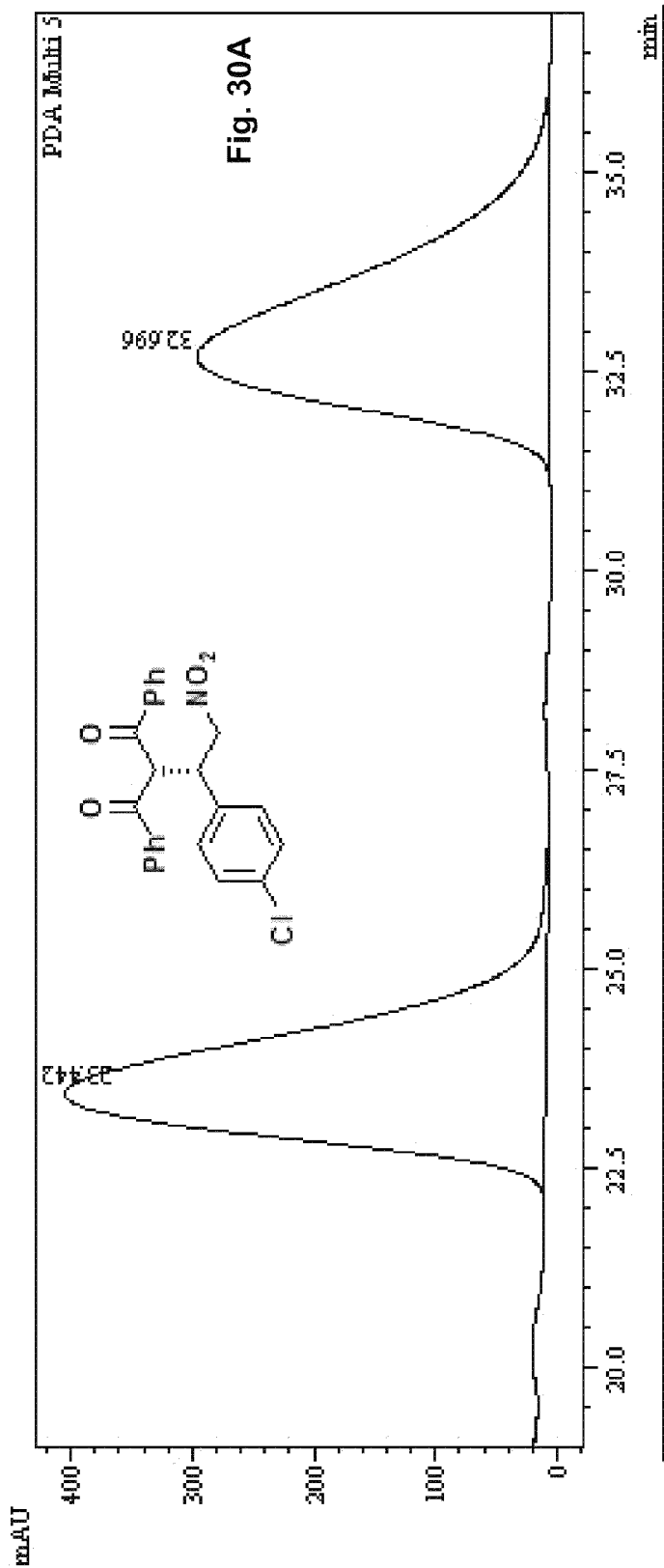
FIG. 30 depicts an HPLC spectrum of a racemic mixture of compound 3g (A) in comparison the obtained product 3g (B).
Figure 31A:
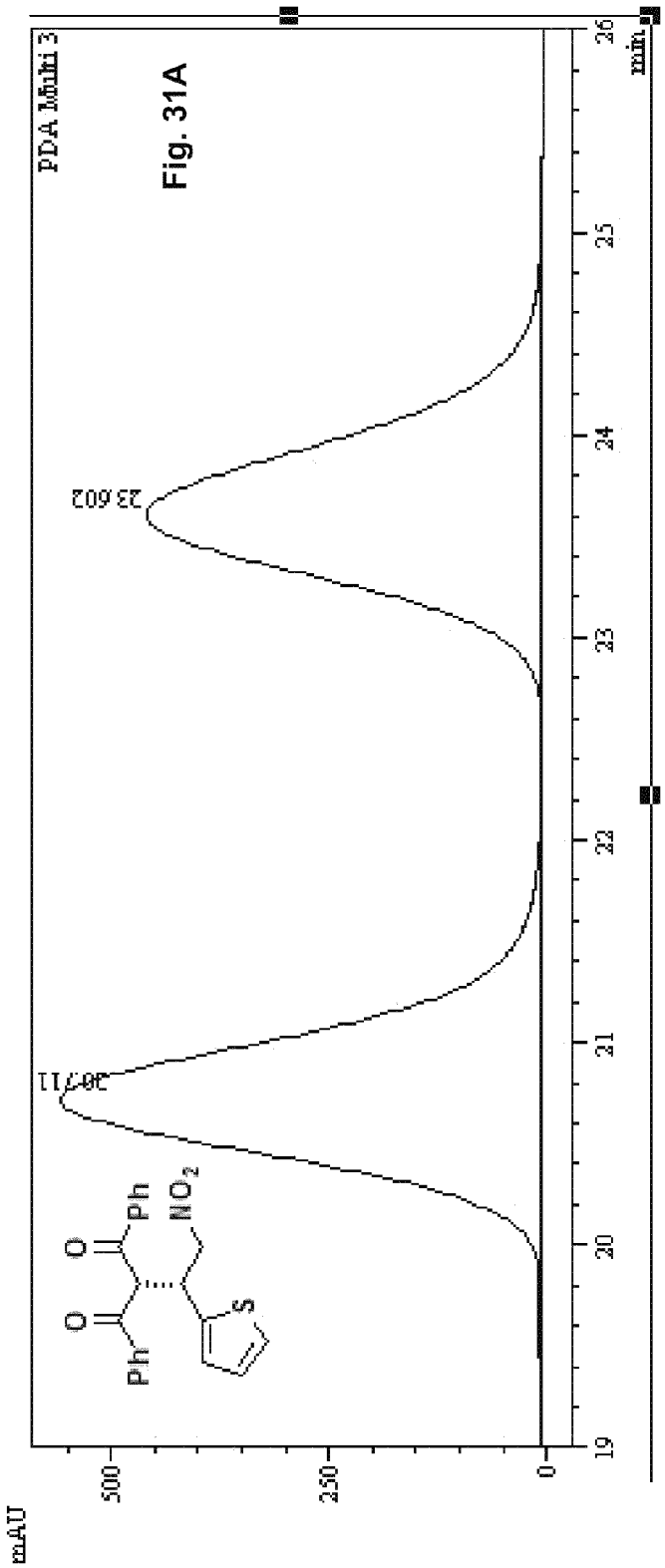
FIG. 31 depicts an HPLC spectrum of a racemic mixture of compound 3h (A) in comparison the obtained product 3h (B).
Figure 31B:
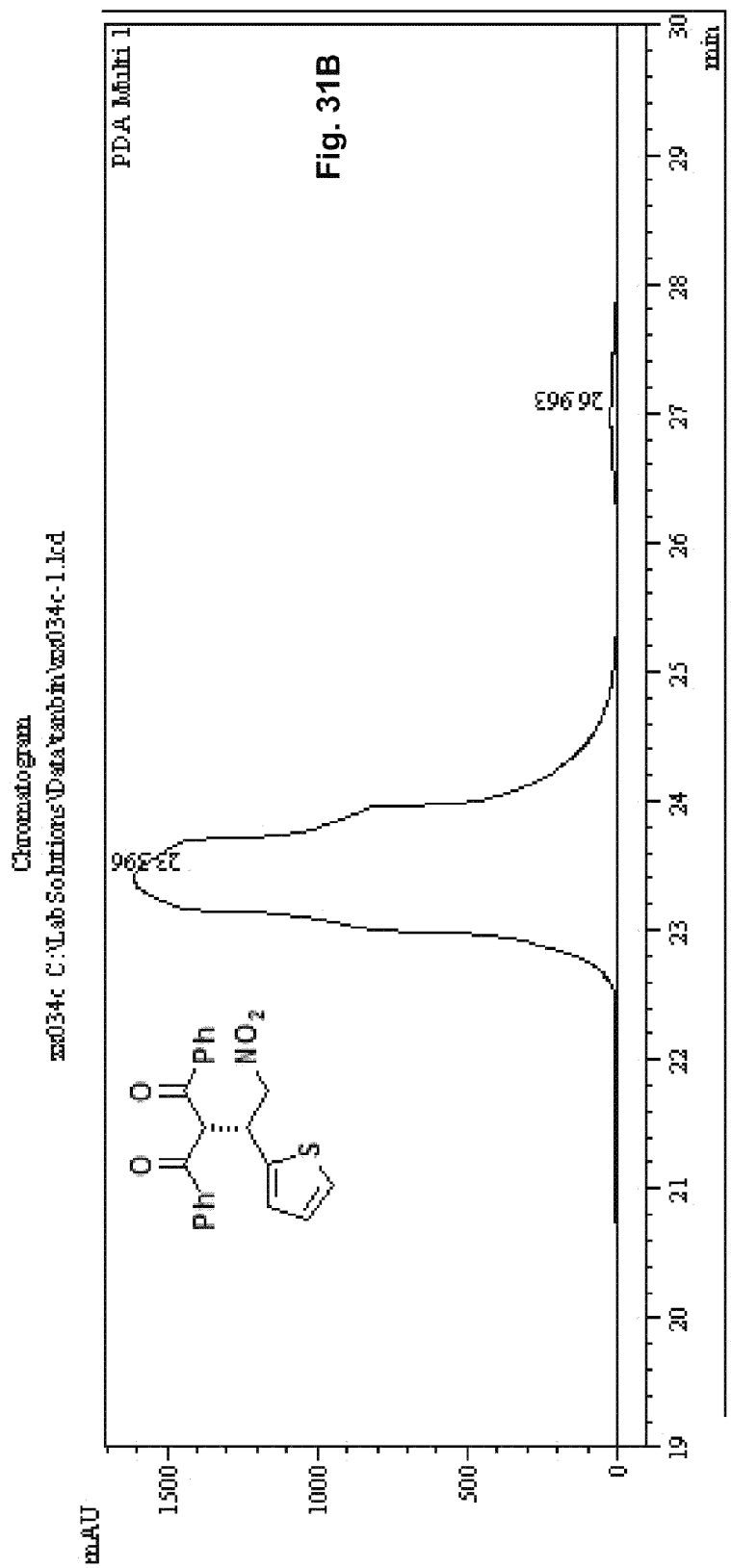
Figure 32B:
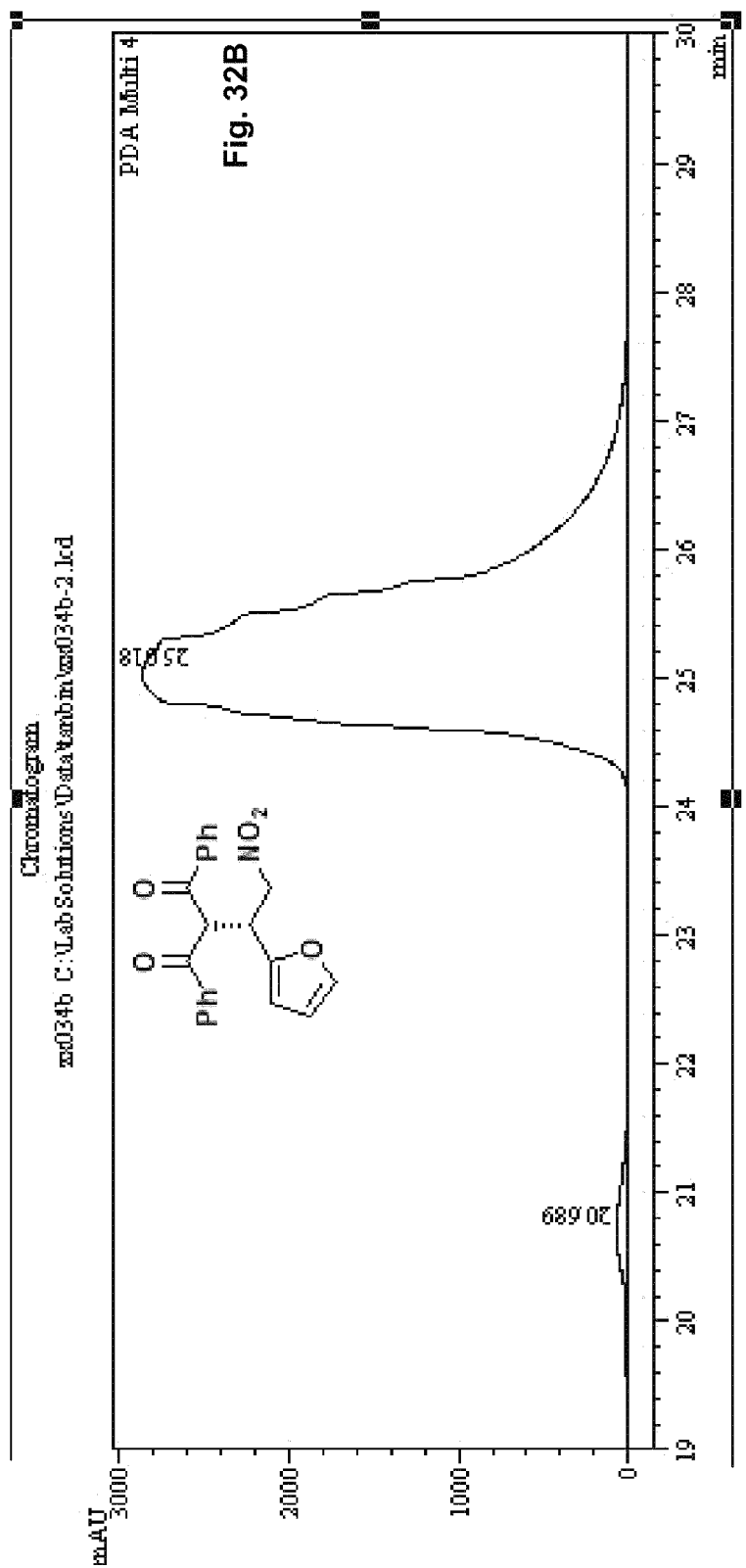
FIG. 32 depicts an HPLC spectrum of a racemic mixture of compound 3i (A) in comparison the obtained product 3i (B).
Figure 33B:
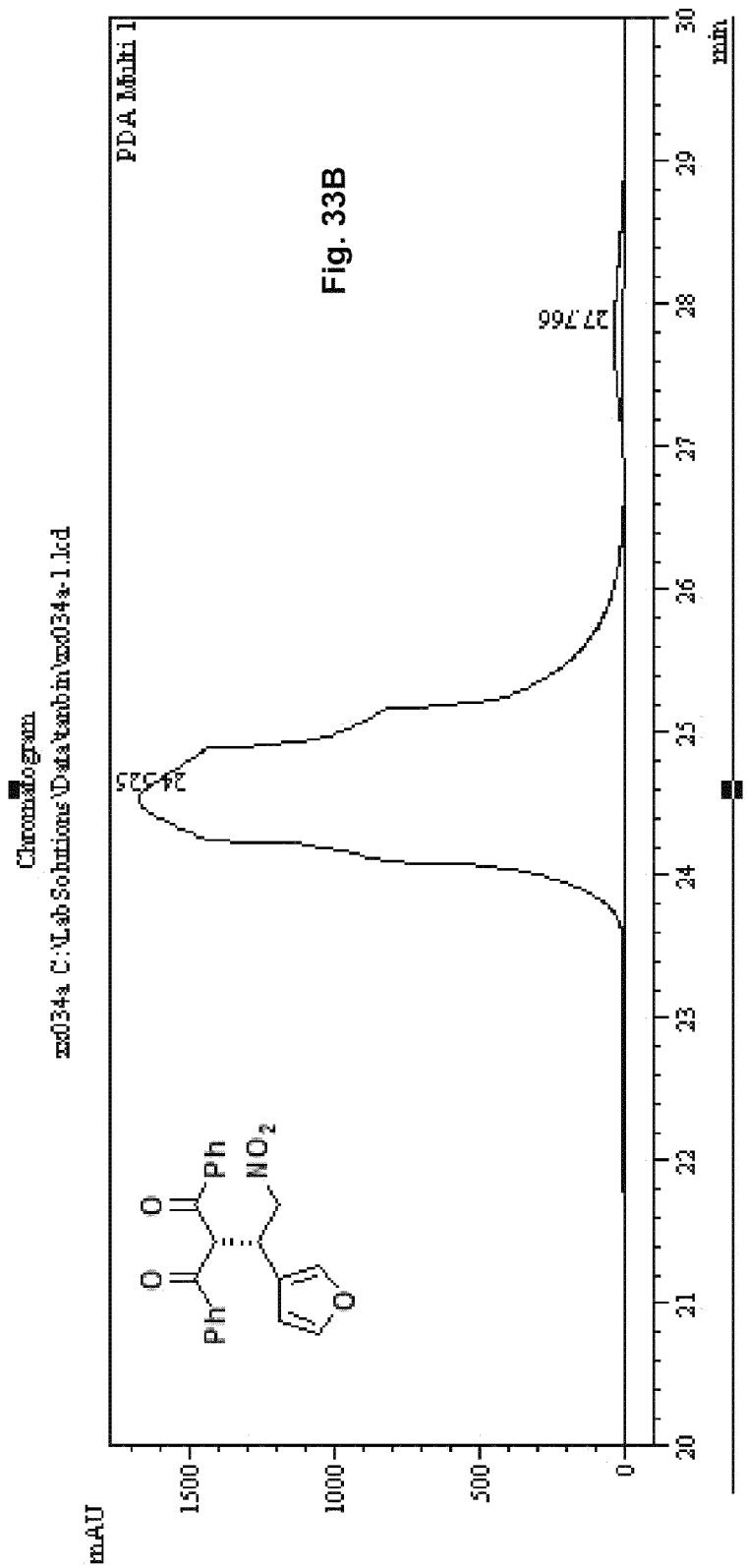
FIG. 33 depicts an HPLC spectrum of a racemic mixture of compound 3j (A) in comparison the obtained product 3j (B).
Figure 34B:
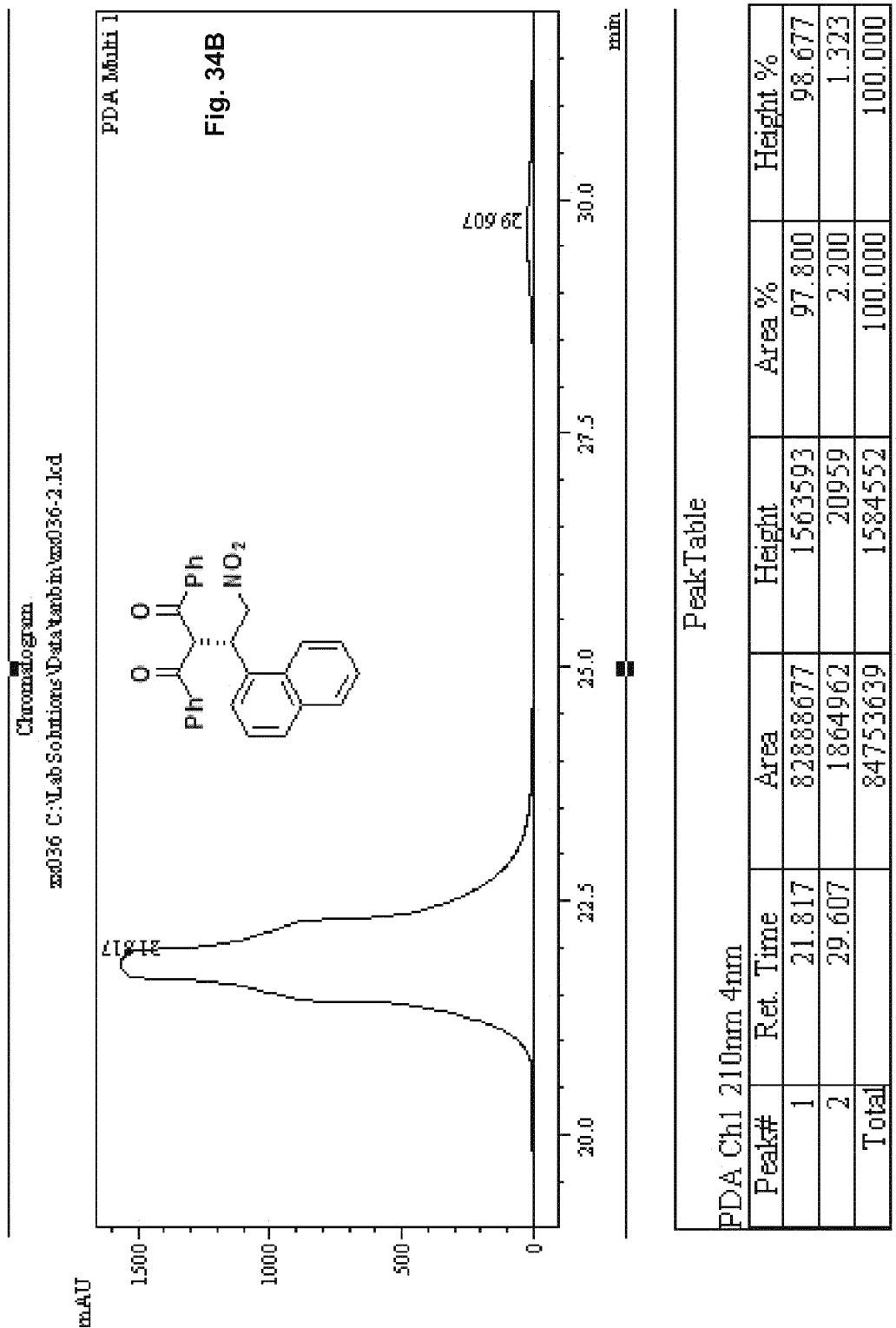
FIG. 34 depicts an HPLC spectrum of a racemic mixture of compound 3k (A) in comparison the obtained product 3k (B).
Figure 35A:
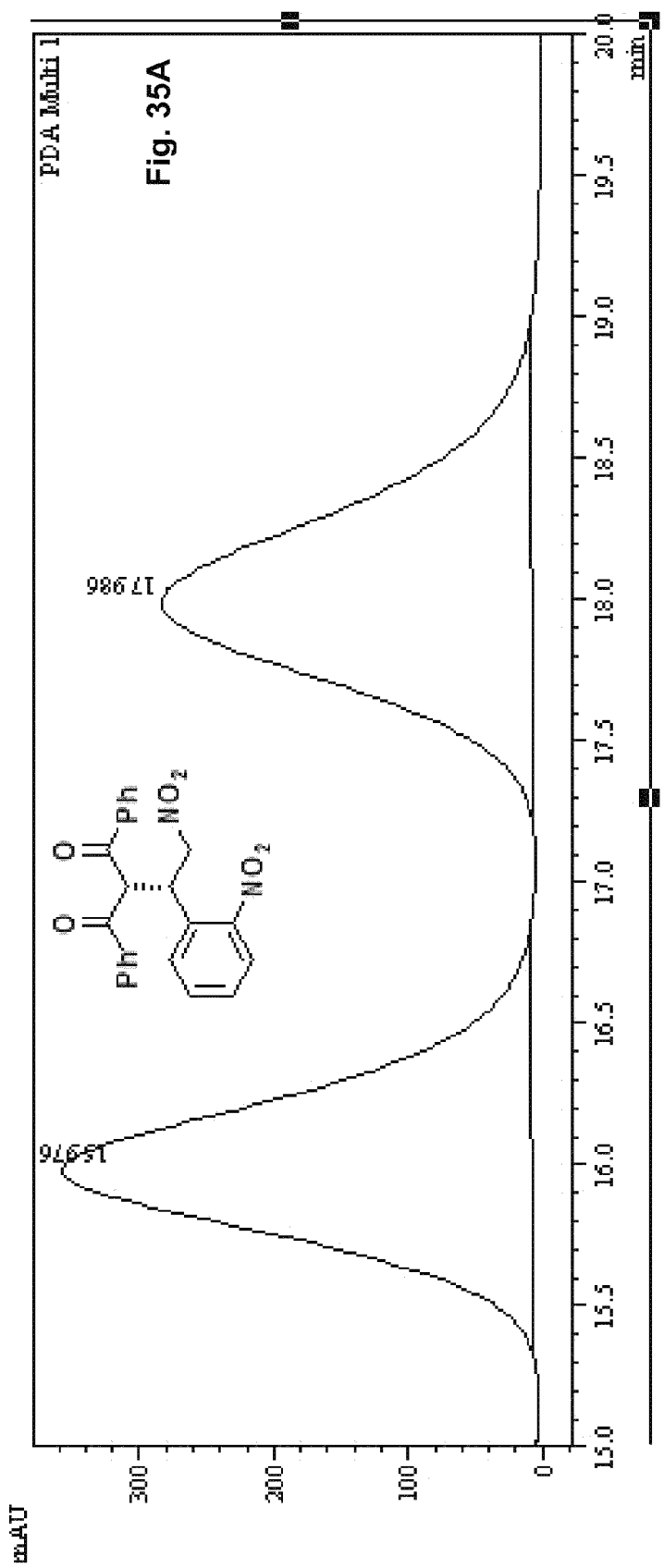
FIG. 35 depicts an HPLC spectrum of a racemic mixture of compound 3l (A) in comparison the obtained product 3l (B).
Figure 35B:
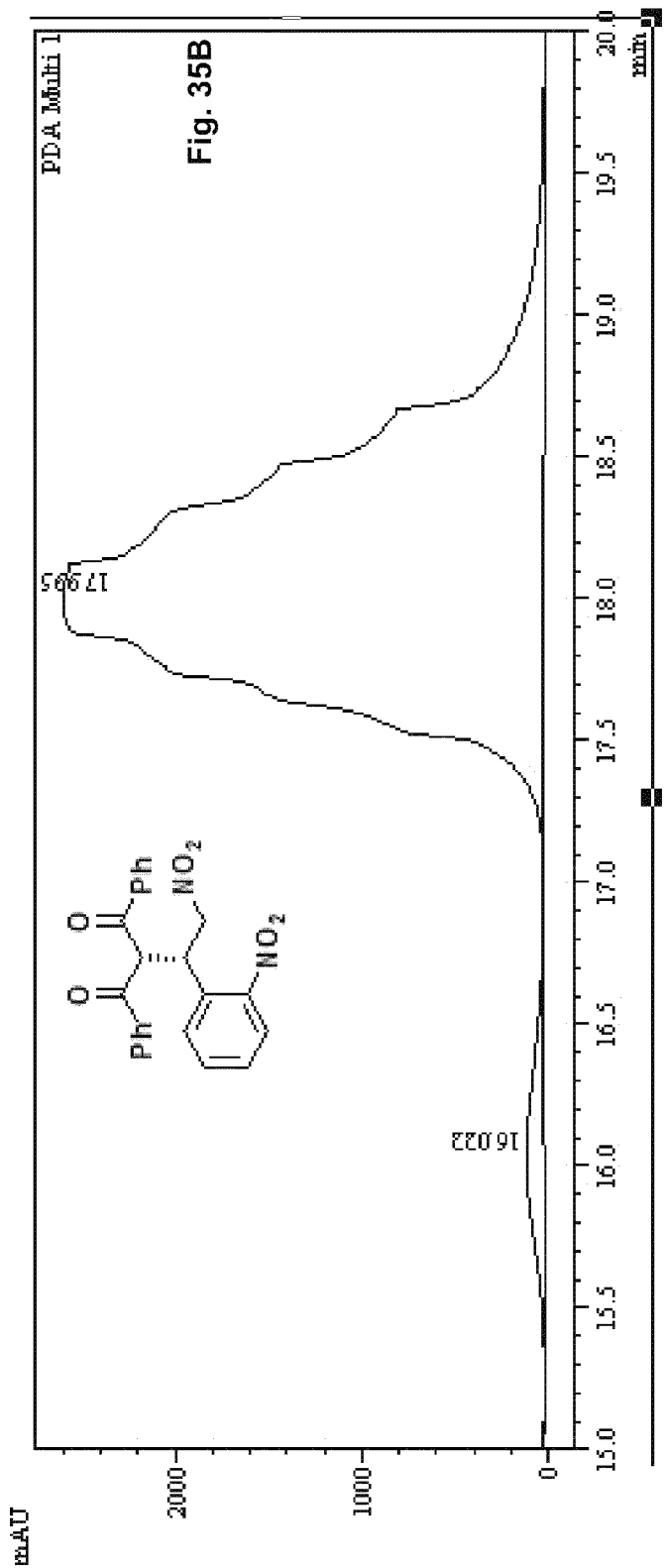
Figure 36A:
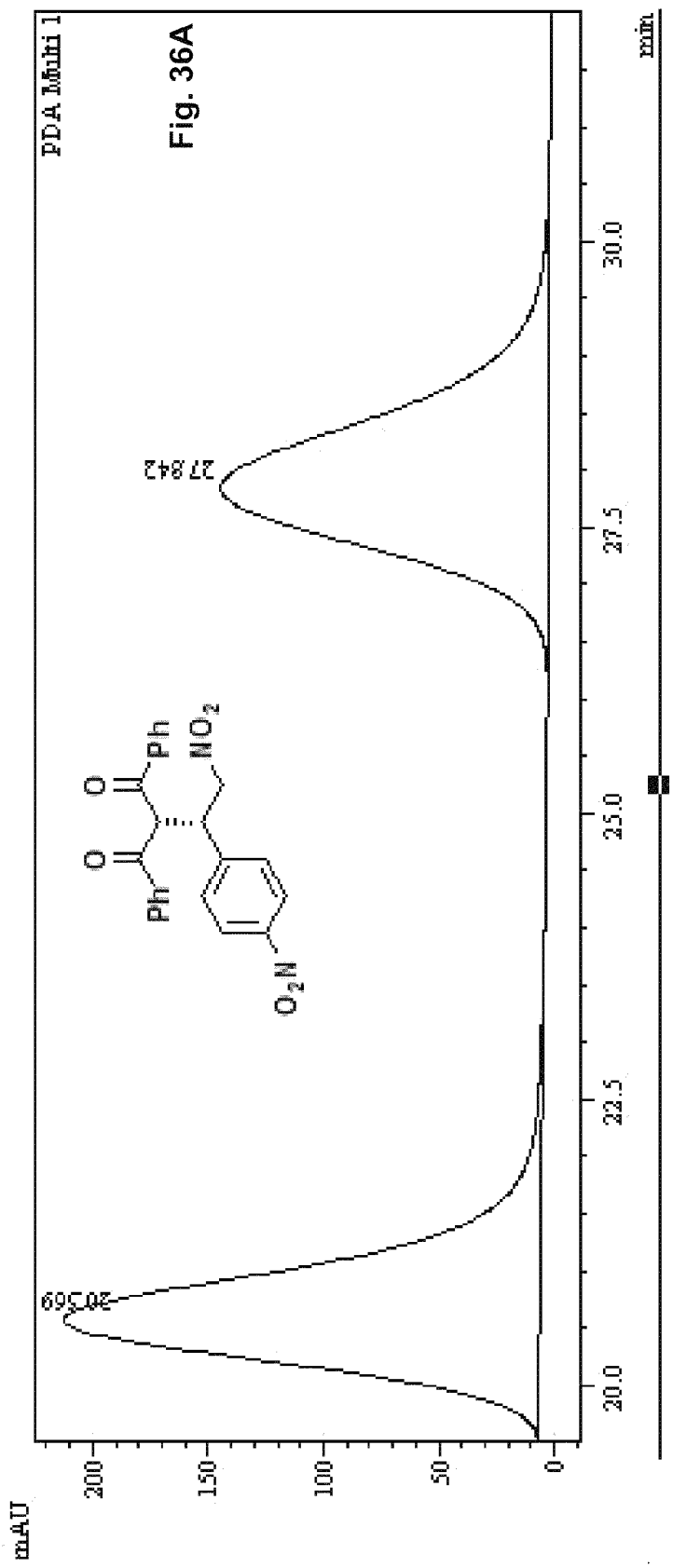
FIG. 36 depicts an HPLC spectrum of a racemic mixture of compound 3m (A) in comparison the obtained product 3m (B).
Figure 36B:
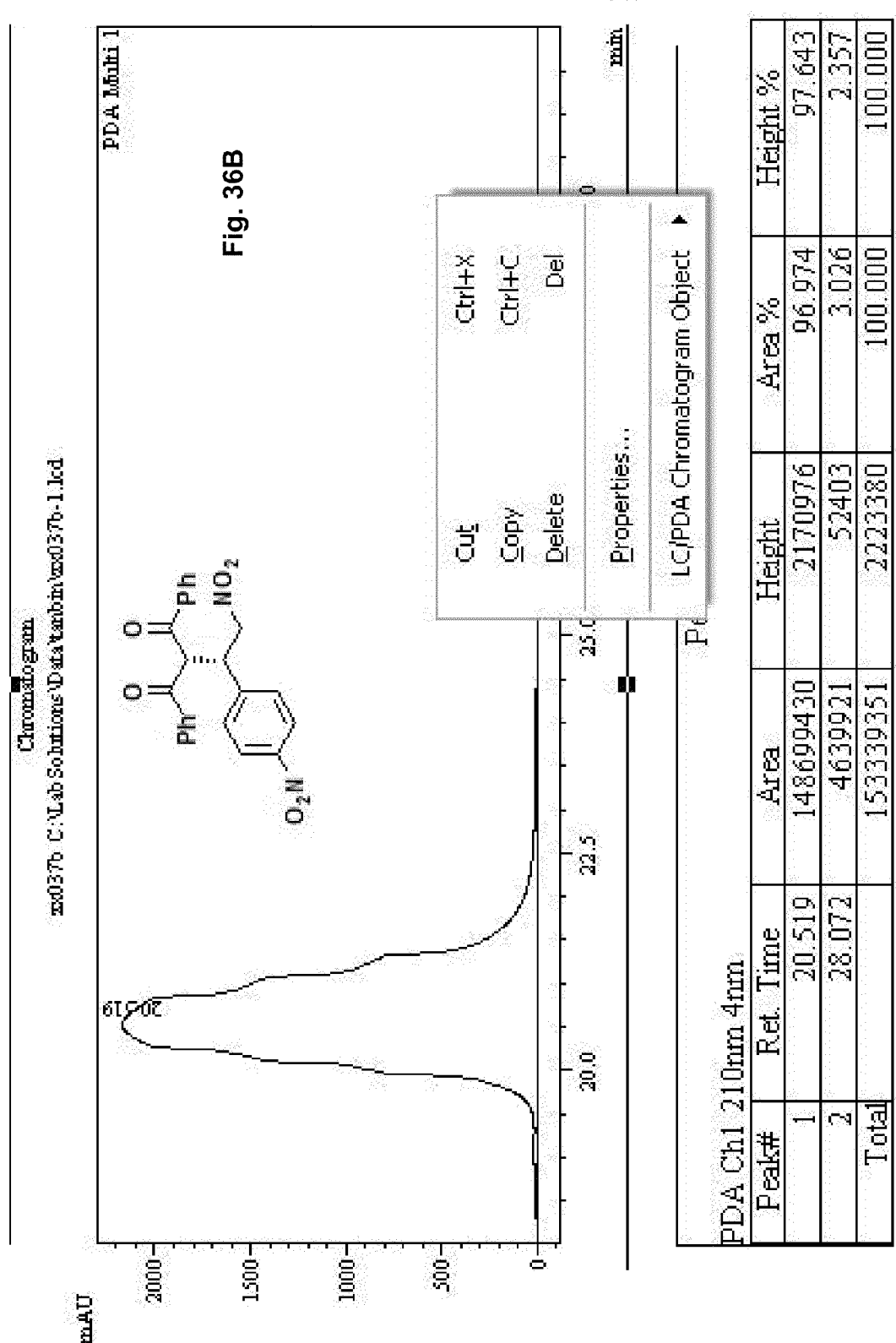
Figure 38A:
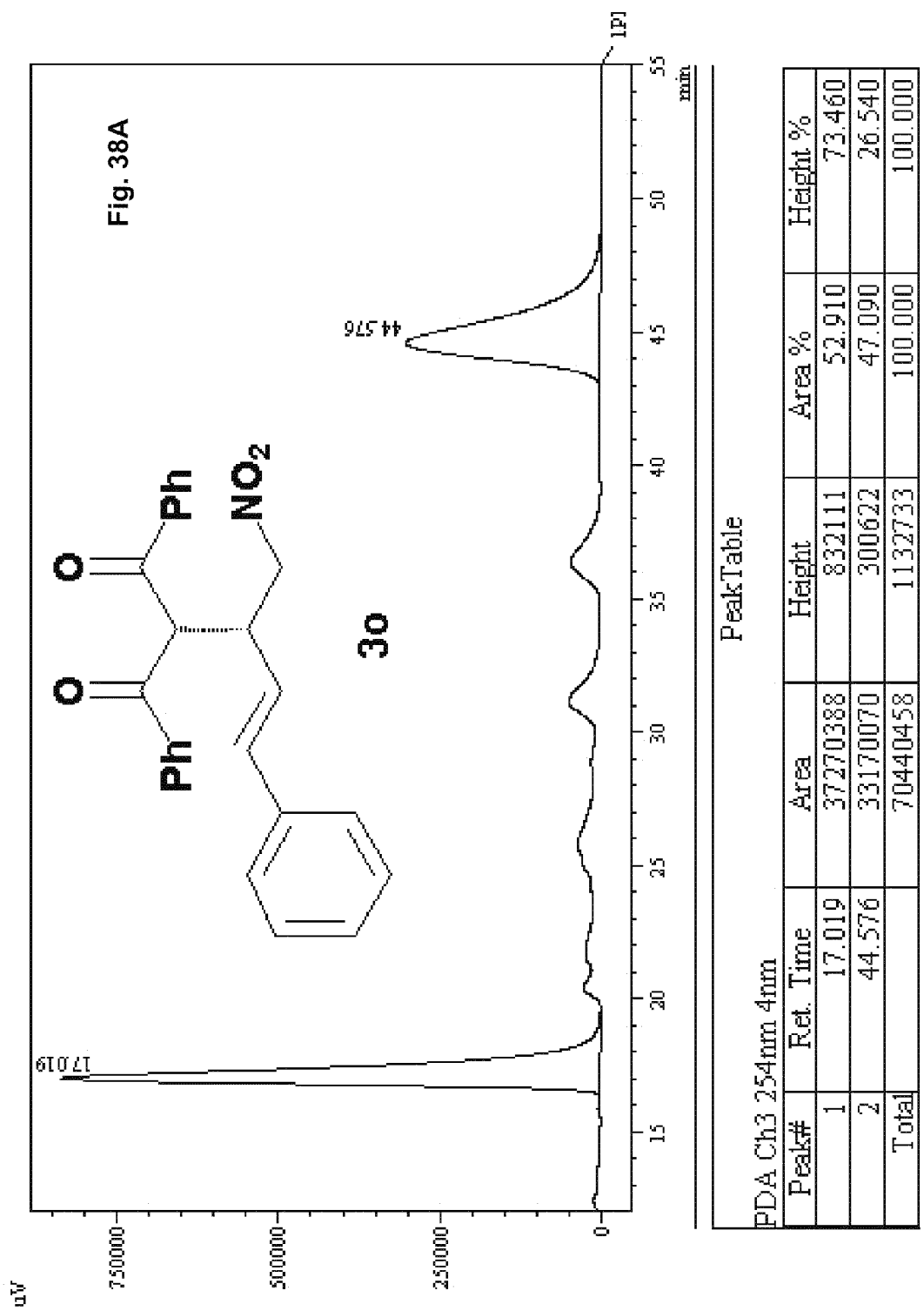
FIG. 38 depicts an HPLC spectrum of a racemic mixture of compound 3o (A) in comparison the obtained product 3o (B).
Figure 38B:
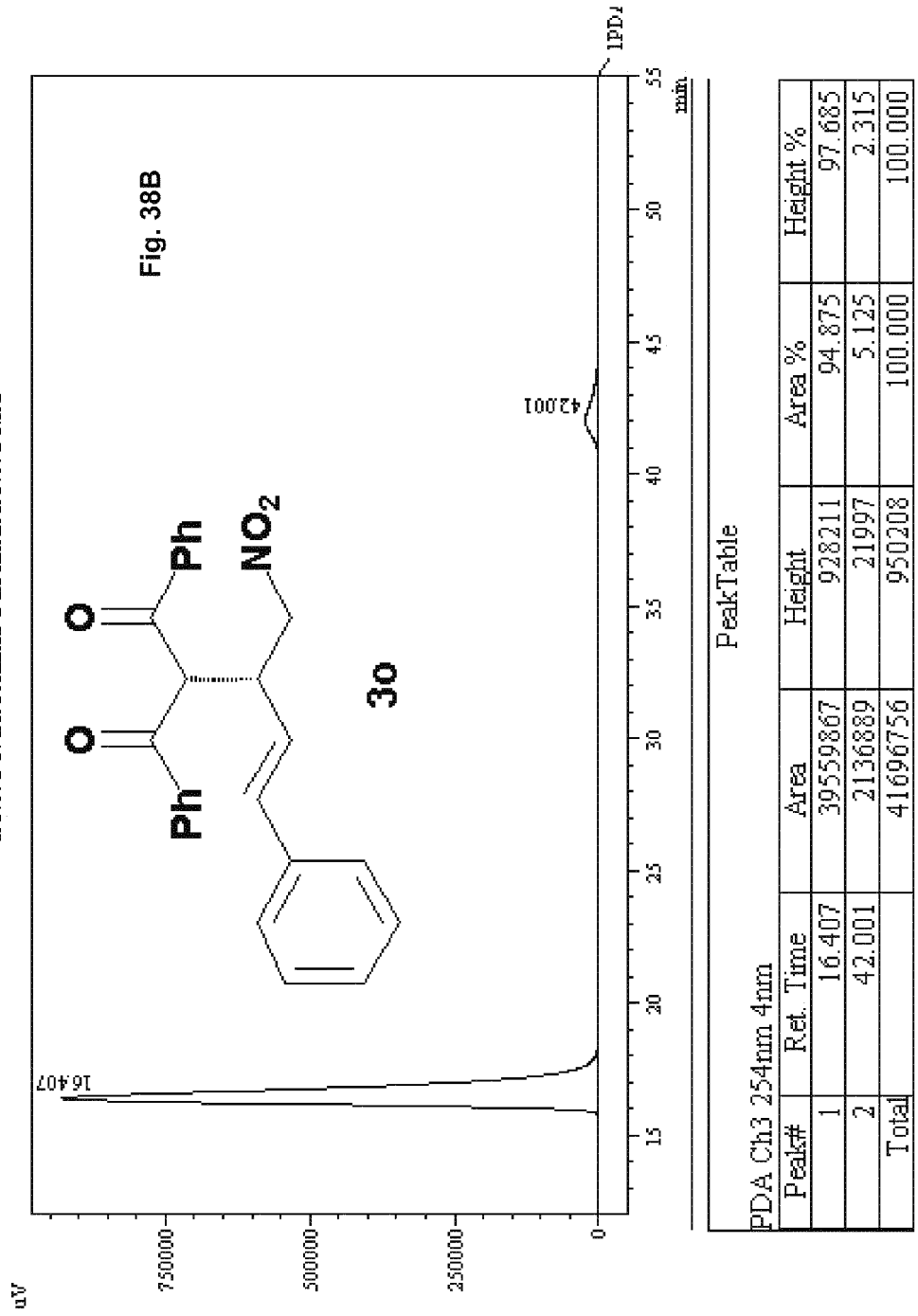
Figure 39A:
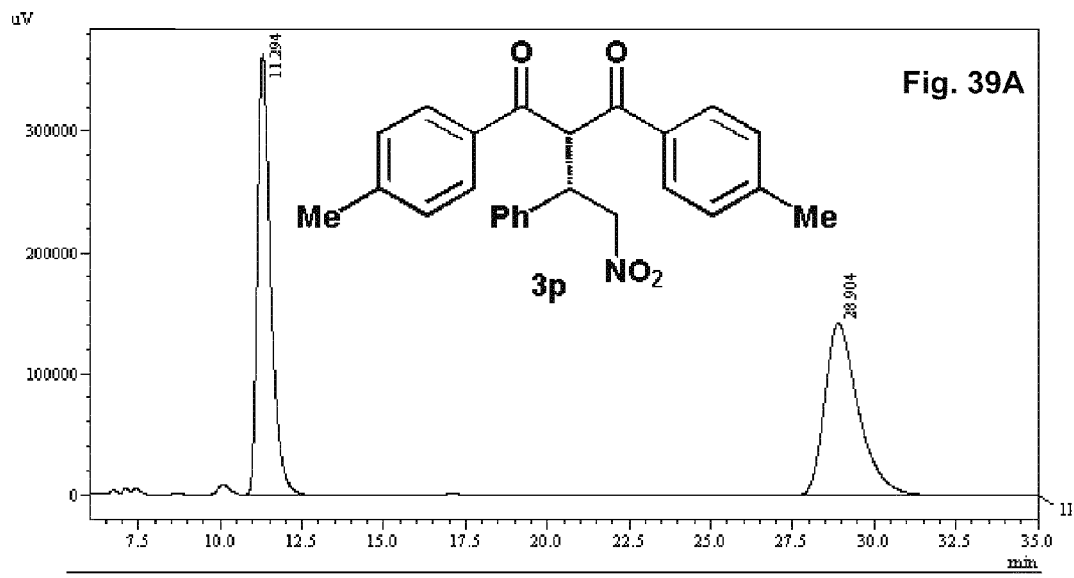
FIG. 39 depicts an HPLC spectrum of a racemic mixture of compound 3p (A) in comparison the obtained product 3p (B).
Figure 39B:
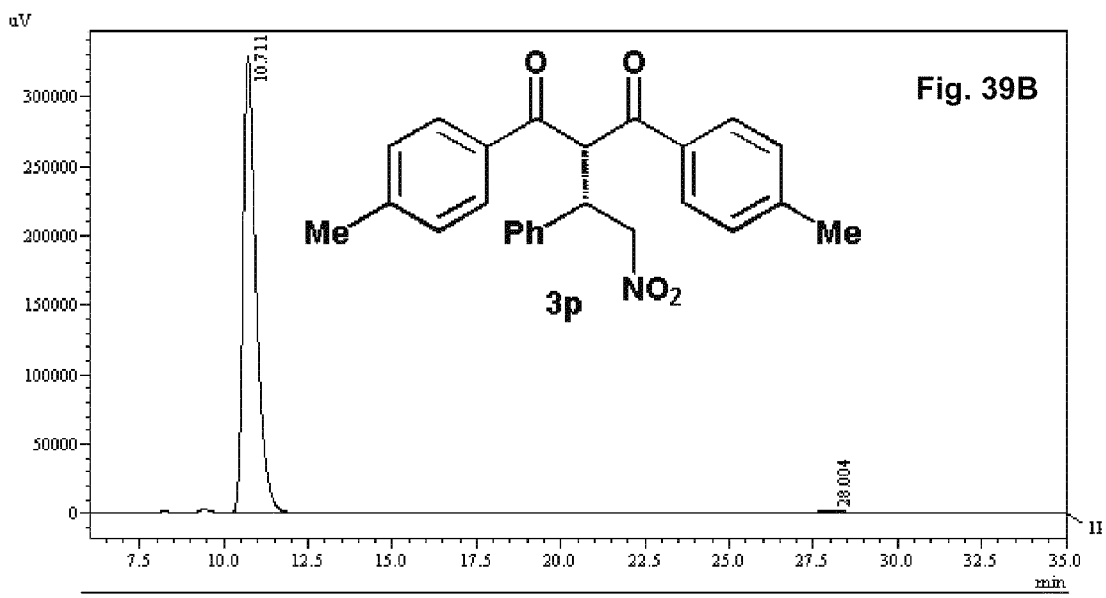

For a scheme and overview on the formation of (3a) and (3g) cf. FIG. 8.

To trans-β-nitrostyrene (2a)

To a solution of 1,3-diphenyl-1,3-propanedione (1a) (67.2 mg, 0.3 mmol, 3 eq) and trans-β-nitrostyrene (1a) (14.9 mg, 0.1 mmol, 1 eq) in diethyl ether (0.3 mL) was added catalyst VI (Q-NH$_2$) (0.015 mmol, 0.15 eq). The resulting mixture was stirred at room temperature (23° C.). After the reaction was complete (monitored by TLC), the product 3a was isolated and purified by centrifuge/washing with diethyl ether (0.5 mL). All the catalyst VI (0.15 eq) and 2 equivalents of the excess the dione 1a were retained in the filtrate. The combined ethereal filtrate was evaporated to 0.3 mL before the dione 1a (1 equiv) and nitrostryene 2a (1 eq) were added again to the solution for the next round of the Michael reaction. This was to ensure that the reaction condition for each cycle was almost the same as the previous one. The excellent yields (96% in average) and enantioselectivities (>99-95% ee) were achieved in seven cycles.

To 1-chloro-4-((E)-2-nitrovinyl)benzene (2g)

To a solution of 1,3-diphenyl-1,3-propanedione (1a) (0.3 mmol, 3 eq) and 1-chloro-4-((E)-2-nitrovinyl)benzene (2g) (0.1 mmol, 1 eq) in diethyl ether (0.3 mL) was added catalyst VI (Q-NH2) (0.015 mmol, 0.15 eq). The resulting mixture was stirred at room temperature (23° C.). After the reaction was complete (monitored by TLC), the product 3g was isolated and purified by centrifuge/washing with diethyl ether (0.3 mL). All the catalyst VI (0.15 equiv) and 2 equivalents of the excess the dione 1a were retained in the filtrate. The combined ethereal filtrate was evaporated to 0.3 mL before the dione 1a (1 eq) and 2g (1 eq) were added again to the solution for the next round of the Michael reaction. This was to ensure that the reaction condition for each cycle was almost the same as the previous one. The excellent yields (96% in average) and enantioselectivities (98-94% ee) were achieved in seven cycles.

Figure 7B:
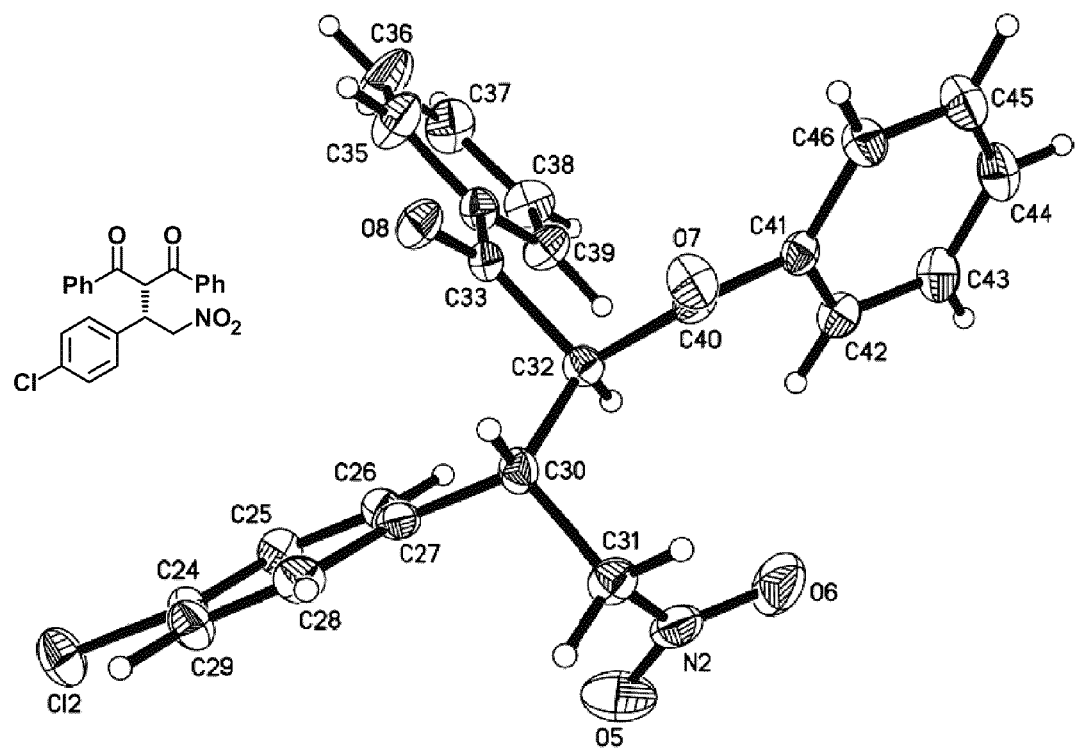
FIG. 7B depicts the X-ray structure of compound 3g (ORTEP).

The absolute configuration of one product 3g was determined by X-ray crystallography to be S(ORTEP, cf. FIG. 7B). For the X-ray crystallography data of the product 3g, see the CIF file (zgf21.cif) which was deposited at the Cambridge Crystallographic Data Centre (CCDC) and its deposition number is CCDC 658642.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of carrying out a Michael reaction with recovery of the catalyst, the process comprising:
providing a first compound of the general formula (1):

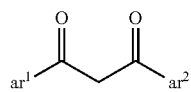
(1)

wherein $ar^1$ and $ar^2$ are independently from one another an aromatic moiety with 5 to 30 carbon atoms and 0 to 5 heteroatoms selected from the group consisting of N, O, S, Se and Si, and
providing a second compound of the general formula (2):

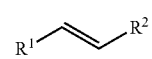
(2)

wherein $R^1$ is one of an aliphatic, an alicyclic, an aromatic and an arylaliphatic group with 3 to 30 carbon atoms and 0 to 5 heteroatoms selected from the group consisting of N, O, S, Se and Si, and
$R^2$ is one of CN, CO—$R^5$, COOH, CHO, $NO_2$, and $SO_2$—$R^5$, wherein $R^5$ is one of an aliphatic, an alicyclic, an aromatic and an arylaliphatic group with 1 to 30 carbon atoms and 0 to 5 heteroatoms selected from the group consisting of N, O, S, Se and Si;
providing a catalyst of the general formula (4):

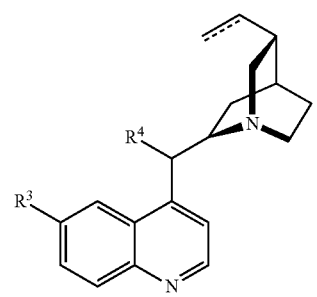
(4)

wherein $R^3$ is one of H, OMe, OH, OTf, SH, and $NH_2$;
$R^4$ is one of OH and $N(R^8)H$;
wherein $R^8$ is one of H, a carbamoyl group, and a thiocarbamoyl group, and
===== represents one of a single and a double bond;
contacting in an aliphatic ether solvent the first compound of formula (1), the second compound of formula (2) and the catalyst of formula (4), thereby forming a reaction mixture,
allowing the first and the second compound to undergo a Michael reaction, thereby allowing the formation of an adduct between the first compound and the catalyst of the general formula (4); and
collecting the adduct between the first compound and the catalyst of the general formula (4), wherein the adduct is precipitated and collected.

2. The process of claim 1, wherein the first compound is provided in excess to the second compound.

3. The process of claim 1, wherein collecting the adduct between the first compound and the catalyst comprises at least one of filtration and centrifugation.

4. The process of claim 1, wherein allowing the first and the second compound to undergo a Michael reaction is carried out at a temperature selected in the range from −20° C. to 30° C.

5. The process of claim 1, wherein the process is a process of carrying out an asymmetric Michael reaction, wherein the catalyst of the general formula (4) is of one of formulas (4A) and (4B):

(4A)

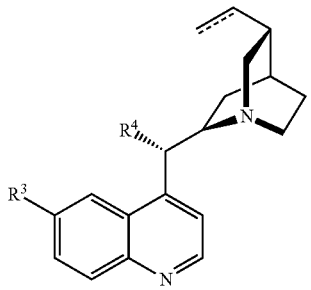

(4B)

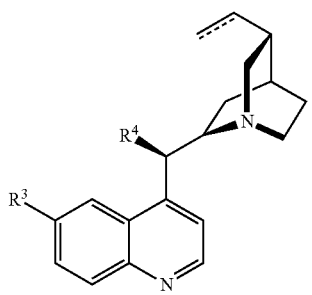

wherein $R^3$ is one of H, OMe, OH, OTf, SH, and NH$_2$,
$R^4$ is one of OH and —N(R$^8$)H, wherein
$R^8$ is one of H, a carbamoyl group, and a thiocarbamoyl group, and
¢ represents one of a single and a double bond.

6. The process of claim 5, wherein allowing the first and the second compound to undergo a Michael reaction yields at least one of product (3A) and product (3B):

(3A)

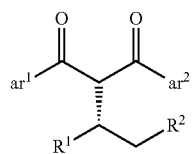

(3B)

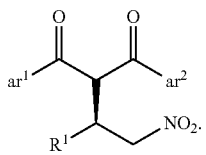

7. The process of claim 1, wherein the first compound is provided in a two-fold amount compared to the amount of the second compound.

8. The process of claim 1, wherein the compound of the general formula (2) is a compound of formula (2A):

(2A)

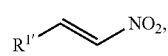

wherein $R^{1'}$ is an aromatic or a heteroaromatic moiety with 3 to 30 carbon atoms and 0 to 5 heteroatoms selected from the group consisting of N, O, S, Se and Si.

9. The process of claim 1, wherein allowing the first and the second compound to undergo a Michael reaction yields the product (3)

(3)

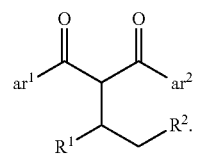

* * * * *